US006664053B1

(12) United States Patent
Kovacs et al.

(10) Patent No.: US 6,664,053 B1
(45) Date of Patent: Dec. 16, 2003

(54) **IDENTIFICATION OF A REGION OF THE MAJOR SURFACE GLYCOPROTEIN (MSG) GENE OF HUMAN *PNEUMOCYSTIS CARINII***

(75) Inventors: Joseph A. Kovacs, Potomac, MD (US); Shengning Huang, N. Potomac, MD (US); Henry Masur, Bethesda, MD (US); Steven H. Fischer, Rockville, MD (US); Vee J. Gill, Potomac, MD (US); Qin Mei, North Wales, PA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/762,724

(22) PCT Filed: Aug. 17, 1999

(86) PCT No.: PCT/US99/18750

§ 371 (c)(1), (2), (4) Date: Feb. 9, 2001

(87) PCT Pub. No.: WO00/09760

PCT Pub. Date: Feb. 24, 2000

Related U.S. Application Data

(60) Provisional application No. 60/096,805, filed on Aug. 17, 1998.

(51) Int. Cl.[7] .......................... C07H 21/04; C12Q 1/68

(52) U.S. Cl. .............................. 435/6; 435/91.2; 435/5; 435/91.1; 536/23.1

(58) Field of Search .............................. 435/6, 5, 91.1, 435/91.2; 536/23.1

(56) References Cited

U.S. PATENT DOCUMENTS

| | | | | | |
|---|---|---|---|---|---|
| 4,683,195 | A | * | 7/1987 | Mullis et al. | 435/6 |
| 5,164,490 | A | | 11/1992 | Santi et al. | |
| 5,442,050 | A | | 8/1995 | Fishman | |
| 5,501,947 | A | | 3/1996 | Emery et al. | |
| 5,519,127 | A | | 5/1996 | Shah et al. | |
| 5,593,836 | A | | 1/1997 | Niemiec et al. | |
| 5,595,874 | A | * | 1/1997 | Hogan et al. | 435/6 |
| 5,702,901 | A | | 12/1997 | Cummins et al. | |
| 5,776,680 | A | | 7/1998 | Leibowitz et al. | |

FOREIGN PATENT DOCUMENTS

| | | |
|---|---|---|
| WO | PCT/GB91/00869 | 5/1991 |
| WO | PCT/US93/09635 | 8/1993 |

OTHER PUBLICATIONS

Wright et al. "Cloning and characterization of a conserved region of human and Rhesus macaque Pneumocystis carinii gpA". Gene. vol. 167, No. 1–2, pp. 185–189, 1995.*

Stringer et al. "Genes encoding antigenic surface glycoproteins in Pneumocystis from Humans" J. Euk. Microbiol. Vo. 40, No. 6, pp. 821–826, 1993.*

Leigh et al., "Quantitative and qualitative comparison of DNA amplification by PCR with immunofluorescence staining for diagnosis of *Pneumocystis carinii* pneumonia," *J. Clin. Pathol.*, 46:140–144, 1993.

Moonens et al., "Rapid Simple and Nested Polymerase Chain Reaction for the Diagnosis of *Pneumocystis carinii* pneumonia," *Scand. J. Infect. Dis.*, 27:358–362, 1995.

Schluger and Rom, "The Polymerase Chain Reaction in the Diagnosis and Evaluation of Pulmonary Infections," *Am. J. Respir. Crit. Care Med.*, 152:11–16, 1995.

Baughman and Liming, "Diagnostic strategies in *Pneumocystis carinii* pneumonia," *Front. Biosci.*, 3:e1–12, Jan. 1, 1998.

Tanabe et al., "Glycoproteins Composed of Major Surface Immunodeterminants of *Pneumocystis carinii*, " *Infect. Immun.*, 57(5):1363–1368, May 1989.

Theus et al., "Cytokine responses to the native and recombinant forms of the major surface glycoprotein of *Pneumocystis carinii*," *Clin. Exp. Immunol.*, 109:255–260, 1997.

Haidaris et al., GenBank Accession No. AF043102, Jun. 6, 1998.

Wada et al., GenBank Accession No. D31920, Sep. 22, 1997.

Wada et al., GenBank Accession No. D31914, Sep. 22, 1997.

Kovacs et al., GenBank Accession No. U39660, Nov. 29, 1995.

Edman et al., GenBank Accession No. U53921, Dec. 24, 1996.

Mei et al., "Characterization of major surface glycoprotein genes of human *Pneumocystis carinii* and high–level expression of a conserved region," *Infect. Immun.*, 66(9):4268–4273, Sep. 1998.

Caliendo et al., "Performance of a PCR assay for detection of *Pneumocystis carinii* from respiratory specimens," *J. Clin. Microbiol.*, 36(4):979–982, Apr. 1998.

Tang et al., "Determination of copy number of rRNA genes in *Pneumocystis carinii* f. sp. hominis,"*J. Clin. Microbiol.*, 36(9):2491–2494, Sep. 1998.

(List continued on next page.)

*Primary Examiner*—Gary Benzion
*Assistant Examiner*—Jeanine Goldberg
(74) *Attorney, Agent, or Firm*—Klarquist Sparkman, LLP

(57) ABSTRACT

Particularly sensitive techniques for the detection of *P. carinii* in clinical samples are disclosed. These techniques relate to the PCR amplification and/or detection of human-*P. carinii* major surface glycoprotein (MSG) gene sequences. Also disclosed are seven novel genes encoding human-*P. carinii* MSG, and the proteins encoded for by these genes. These genes provide proof that human-*P. carinii* MSG is encoded for by a highly conserved gene family, and that the conesponding proteins have a very highly conserved region of about 100 amino acids near their C-terminal end. This highly conserved carboxy-terminal region has a significantly different sequence than that found in rat-derived MSG.

14 Claims, 13 Drawing Sheets

OTHER PUBLICATIONS

Lopez et al., "Europium(III) trisbipyridine cryptate label for time–resolved fluorescence detection of polymerase chain reaction products fixed on a solid support," *Clin. Chem.*, 39(2):196–201, Feb. 1993 (abstract only).

Hierholzer et al., "Detection of adenovirus in clinical specimens by polymerase chain reaction and liquid–phase hybridization quantitated by time–resolved fluorometry," *J. Clin. Microbiol.,* 31(7):1886–1891, Jul. 1993 (abstract only).

Eskola et al., "Detection of Philadelphia chromosome using PCR and europium–labeled DNA probes," *Clin. Biochem.,* 27(5):373–379, Oct. 1994 (abstract only).

Chan et al., "Quantification of polymerase chain reaction products in agarose gels with a fluorscent europium chelate as label and time–resolved fluorescence spectroscopy," *Anal. Chem.,* 65(2):158–163, Jan. 15, 1993 (abstract only).

Dahlen et al., "Detection of human immunodeficiency virus type 1 by using the polymerase chain reaction and a time–resolved fluorescence–based hybridization assay," *J. Clin. Microbiol.*, 29(4):798–804, Apr. 1991 (abstract only).

Dahlen et al., "The use of europium (Eu3+) labelled primers in PCR amplification of specific target DNA," *Mol. Cell. Probes*, 5(2):143–149, Apr. 1991 (abstract only).

Guadiz et al. GenBank Accession No. AF035226, Jan. 2, 1998.

Garbe and Stringer, "Molecular Characterizaton of Clustered Variants of Genes Encoding Major Surface Antigens of Human *Pneumocystis carinii,*" *Infect. Immun.,* 62(8):3092–3101, Aug. 1994.

Theus et al., "Immunization with the major surface glycoprotein of *Pneumocystis carinii* elicits a protective response," *Vaccine*, 16:(11/12):1149–1157, 1998.

Kovacs et al., "Multiple Genes Encode the Major Surface Glycoprotein of *Pneumocystis carinii,*" *J. Biol. Chem.,* 268(8):6034–6040, Mar. 15, 1993.

Chary–Reddy and Graves, "Identification of Extrapulmonary *Pneumocystis carinii* in Immunocompromised Rats by PCR," *J. Clin. Microbiol.,* 34(7):1660–1665, Jul. 1996.

Mei et al., "Characterization of Major Surface Glycoprotein Genes of Human *Pneumocystis carinii* and High–Level Expression of a Conserved Region," *Infect. Immun.,* 66(9):4268–4273, Sep. 1998.

Schluger et al., "Application of DNA Amplification to Pneumocystosis: Presence of Serum *Pneumocystis carinii* DNA During Human and Experimentally Induced *Pneumocystis carinii* Pneumonia," *J. Exp. Med.,* 176:1327–1333, Nov. 1992.

Ortona et al., "Non specific PCR products using rat–derived *Pneumocystis carinii* dihydrofolate reductase gene–specific primers in DNA amplification of human respiratory samples," *Mol. Cell. Probes*, 10:187–190, 1996.

Helweg–Larsen et al., "Diagnostic use of PCR for detection of *Pneumocystis carinii* in oral wash samples," *J. Clin. Microbiol.,* 36(7):2068–2072, Jul. 1998.

De la Viuda et al., "Use of AmpliWax to optimize amplicon sterilization by isopsoralen," *J. Clin. Microbiol.,* 34(12):3115–3119, Dec. 1996 (abstract only).

Rys and Persing, "Preventing false positives: quantitative evaluation of three protocols for inactivation of polymerase chain reaction amplification products," *J. Clin. Microbiol.,* 31(9):2356–2360, Sep. 1993 (abstract only).

Cimino et al., "Post–PCR sterilization: a method to control carryover contamination for the polymerase chain reaction," *Nucleic Acids Res.,* 19(1):99–107, Jan. 11, 1991 (abstract only).

Isaacs et al., "Post–PCR sterilization: development and application to an HIV–1 diagnostic assay," *Nucleic Acids Res.,* 19(1):109–116, Jan. 11, 1991 (abstract only).

Kovacs et al., "Diagnosis of *Pneumocystis carinii* pneumonia: improved detection in sputum with use of monoclonal antibodies," *New England J. Med.,* 318(10):589–593, Mar. 10, 1988.

Lipschik et al., "Improved diagnosis of *Pneumocystis carinii* infection by polymerase chain reaction on induced sputum and blood," *Lancet*, 340:203–206, Jul. 25, 1992.

Wakefield et al., "Detection of *Pneumocystis carinii* with DNA amplification," *Lancet*, 336:451–453, Aug. 25, 1990.

Ognibene et al., "The Diagnosis of *Pneumocystis carinii* Pneumonia in Patients with the Acquired Immunodeficiency Syndrome Using Subsegmental Bronchoalveolar Lavage," *Am. Rev. Respir. Dis.,* 129(6):929–932, Jun. 1984.

Bigby et al., "The Usefulness of Induced Sputum in the Diagnosis of *Pneumocystis carinii* Pneumonia in Patients with the Acquired Immunodeficiency Sydrome," *Am. Rev. Respir. Dis.,* 133(4):515–518, Apr. 1986.

Wakefield et al., "Amplification of mitochondrial ribosomal RNA sequences from *Pneumocystis carinii* DNA of rat and human origin," *Mol. Biochem. Parasitol.,* 43:69–76, 1990.

Santos et al., "Use of the polymerase chain reaction in the diagnosis of leprosy," *J. Med. Microbiol.,* 46:170–172, 1997.

Wada et al., "cDNA Sequence Diversity and Genomic Clusters of Major Surface Glycoprotein Genes of *Pneumocystis carinii,*" *J. Infect. Dis.,* 168:979–985, 1993.

Nakamura et al., "Structure of Major Surface Determinants and DNA Diagnosis of *Pneumocystis carinii,*" *J. Protozool.,* 36(1):58S–60S, Jan.–Feb. 1989.

Line and Walzer, "Analysis of a surface antigen of *Pneumocystis carinii,*" *J. Protozool.,* 36(1):60S–61S, Jan.–Feb. 1989 (abstract only).

* cited by examiner

```
RMSGGP3  M A R P V K R Q A V Q G A - - Q D E I D E K H L L A F I V K D K   30
HMSGp1   V A R A V K R Q V T G A S - - G V D E E E V R L L A L I L K E D   30
HMSGp3   V A R A V K R R A A A Q N - - - - S V E E E Y L L A L I L E N E   28
HMSG11   - A R A V K R R A K G A Q - - N S I D E E H - V L A L I L K K N   28
HMSG14   - A R A V K R Q A K G A Q - - N S I D E E H - V L A L I L K K N   28
HMSG32   - A R A V K R Q A A K A S G A S V Y D G E E I L L A L I A G K K   31
HMSG33   - A R A V K R Q V T G A S - - G Q Y D D E V N I L A L I L Q E D   29
HMSG35   - A R A V K R Q A A G T Q - - N S I D E E H - V L A L I L K E D   28
GBHMSG   V A R A V K R Q V A G V K - - N N E A E E R - L F A L I M R A D   29

RMSGGP3  Y K E E Q K C K E E L E K Y C K E L K E A D K N L E N V D D K V   62
HMSGp1   S K D D K K C E E K L E K H C K E L S E A N L T P E Q V H E K L   62
HMSGp3   Y E N N D K C K K R L K E Y C E V L K N V T K E P K K L E E K L   60
HMSG11   G L E D T K C K T K L E E Y C K T L T N A G L N P E K V H E K L   60
HMSG14   G L E D T K C K T K L E E Y C K T L T N A G L N P E K V H E K L   60
HMSG32   Y N - D N E C K K E L E K Y C K T L T D A E L K P E K V H K K L   62
HMSG33   A M E D T K C K K S L E K Y C E E L K K A S L D M E K V H K M L   61
HMSG35   G L S E Q E C K K K L K K Y C Q E L T E A K L N I E Q V H R K L   60
GBHMSG   Y K D E S K C K N K I K E Y C D G L K N A S L T S E E V H K E L   61

RMSGGP3  K G L C D D K - - - K R D E K C K D V K K K V E D E L K D F E E   91
HMSGp1   K D F C D S K - - - K R D K K C K E L K K N V E K K C G D F K T   91
HMSGp3   D G I C K D D K - - T I E A K C K E S E T K V K A K C T S F Q T   90
HMSG11   K D F C D N G - - - K R N E K C Q D L K N K V N Q K C I K F Q G   89
HMSG14   K D F C D N G - - - K R N E K C Q D L K N K V N Q K C I K F Q G   89
HMSG32   K E F C E N K - - - K A D S K C K E L K E K L T Q K C T A I K G   91
HMSG33   K D F C G N G K A S K A N T K C Q G L Q A K V T G K C T N F K -   92
HMSG35   K G F C E D G - - - K A D T K C K E L K A N I E K K C T T I K G   89
GBHMSG   K D F C K D G - - - S Q G K K C E E L K K N V E A K C N N F K T   90
```

FIGURE 1A

```
RMSGGP3  E L Q K V L N - - - - N I K D E N C E K Y E E K C I L L E E T D  119
HMSGp1   E L E E L V K K E A S N L K N D E C T K N E Q Q C L F L E E A C  123
HMSGp3   E L D K A V K K G A S T L E D N D C K K N E R Q C L F L E G A C  122
HMSG11   K L Q T A A G K K I S E L T D E D C K K N E Q Q C L F L E G A C  121
HMSG14   K L Q T A A R K K I S E L T D E D C K K N E Q Q C L F L E G A C  121
HMSG32   K L T E A I K K K N S D L T D E D C K E N E Q Q C L F L E G A C  123
HMSG33   - - T Q K L G P A L T N P S D D N C K E S E R Q C L F L E G A C  122
HMSG35   K L K E A I K K K I Q I I T D K D C K E N E Q Q C L F L E G V C  121
GBHMSG   K L E G L V K K D A S G L T N D D C K E N E R Q C L F L E G A C  122

RMSGGP3  Y D V I K D N C I E L R E G C Y K L K R E K V A E E L L L R A L  151
HMSGp1   - S D L T K N C N D L R N K C Y Q N K R D K V A K E V L L R I I  154
HMSGp3   P T E L K D K C N E L R N K C Y Q K K R D D V A E K A L L R V L  154
HMSG11   P T E L K D D C N K L R N N C Y Q K E R N N V A E E V L L R A L  153
HMSG14   P T E L K D D C N K L R N N C Y Q K E R N N V A E E V L L R A L  153
HMSG32   P A E L K D D C N T L R N K C Y Q K K R D K V A E E A L L R A V  155
HMSG33   - H N L V E D C N K L R N L C Y Q K K R D G V A E E V L L R A L  153
HMSG35   S K E L K D D C N T L R N K C Y Q K K R D K V A E E V L L R A L  153
GBHMSG   - P D L V E D C S K L R N L C Y Q K K R E G V A E E V L L R A L  153

RMSGGP3  G G - D A K E E A K C K G K M N T V C P V L S R E S D E L M S F  182
HMSGp1   K G K N F K D K N S C E N K L E V Y C Q E L S Q M S D E L M K L  186
HMSGp3   R G - N L K D K N T C K N K L K G V C Q E F N K E S D E L I K L  185
HMSG11   R G - D L N E T K T C E K K L K E V C P K L E R E S D E L T E L  184
HMSG14   R G - D L N E T K T C E K K L K E V C P K L E R E S D E L T E L  184
HMSG32   R G - G L I N E T T C E G K L K E V C I E L S Q E S D E L T K L  186
HMSG33   R S - D L N K T E T H E K K L K E I C P V L Q R E S N E L T D L  184
HMSG35   R S - D L N G S V I C E K K L K E I C P V M G R E S D E L T N L  184
GBHMSG   R G - D L G N K T E C E K K I K D V C P K I G Q E S D E L T L L  184
```

FIGURE 1B

```
RMSGGP3  C L D S A K T C G D L K K K L G T V C E P L K - - - - K E L K D   210
HMSGp1   C F D Q K N T C D N L V K E T Q Q K C E S F K N L K T E I K T I   218
HMSGp3   C L D E E K T C G D L V S K K E Y K C K P L K E G I D L V L G K   217
HMSG11   C L Y Q K T T C V S L V T K G K S K C D T L E K E V E E A L K K   216
HMSG14   C L Y Q K T T C V S L V T K G K S K C D T L E K E V E E A L K K   216
HMSG32   C L Y Q K M T C K T F V L E K Q K K C N A L K Q D V N A A L E K   218
HMSG33   C L N Q K K T C E N I I K E K D K K C T T L K A N V A T A L G -   215
HMSG35   C L N Q K E T C K N I L I E K D K K C G T L K T D V S A A L G -   215
GBHMSG   C L D Q K K T C T N L M T A R D K K C N T L E E D V K K A L E N   215

RMSGGP3  - - - N E L A E K C H E R L E K C H F Y G E A C D D A K - - - -   235
HMSGp1   K E D E Q L K K K C P L L Y E E C I F Y D E S C G N D S - - - -   246
HMSGp3   E - - D L L K E K C L L F L E E C Y F Y G S N C E T D Q - - - -   243
HMSG11   - - - N E L R E K C L L L L E Q C Y F H R G N C E G D K S K C N   245
HMSG14   - - - N E L R E K C L L L L E Q C Y F H R G N C E G D K S K C N   245
HMSG32   K - - D E L R G K C L P L L E R C Y F Y R G N C E D I S K C N K   248
HMSG33   - - - S F K K E I C L E L L E Q C Y F Y I G N C G D D D - - - -   240
HMSG35   - - - S F K K E T C L E L L E Q C Y F Y I G N C G D D D - - - -   240
GBHMSG   K - - N N L L G K C L P L L E H A T F T E G T A K K A S Q C T P   245

RMSGGP3  - - - - - - - - - - - - - C K K F E E Q C K G K N I I Y K A P E   254
HMSGp1   - - - - - - - - - - - L K C S E L E K K C Q E K N I T Y T L S Y   267
HMSGp3   - - - - - - - - - - - P - K C K E F A S K C Q K E N L V Y A A P G   264
HMSG11   K P N N K D C K E Y V P E C D E L A E K C G K E N I V Y M H P G   277
HMSG14   K P N N K D C K E Y V P E C D E L A E K C G K E N I V Y M H P G   277
HMSG32   - - S S E D C Y E Y L P V C D T L A V K C E E N K I I Y T H P G   278
HMSG33   - - - - - - - - - - I I K C I E L G G K C Q E Q N I V Y I P P G   262
HMSG35   - - - - - - - - - - I I K C I E L G G K C Q E Q N I A Y M P P G   262
GBHMSG   - - - N K D C E D Y L P K C D E L A E E C G K K G I I Y I H P G   274
```

FIGURE 1C

```
RMSGGP3  S D L S P V K P R A S L L R S I G L D D V Y K N A E K H G I I   286
HMSGp1   S G F D P I E P E I T L A E E V D L E G I Y R K A A E E G T L V   299
HMSGp3   S H F D P T K L K I R L A E E I D L E K L Y V E A V K K G I H I   296
HMSG11   S D F D P T K P E P T L A E D I G L E E L Y K R A E E D G I F V   309
HMSG14   S D F D P T K P E P T L A E D I G L E E L Y K R A E E D G I F V   309
HMSG32   S D F N P T K S K P T V A E D I G L E E L Y K K A A E E G V H I   310
HMSG33   P D F D P T R P E A T L A E D I D L D E L Y K K A E E D G V F I   294
HMSG35   P D F D P T R P E A T I A E D I G L E E F Y K K V E E D G V F I   294
GBHMSG   P D F D P T K P E P T V A E D I G L E E L Y K K A A E D G V H I   306

RMSGGP3  G K S G V D L P R K S G T K F L Q D L L L L L S R D E D - - - K   315
HMSGp1   G K - - - - - P L - - - P A D A T A L V A F L I Q D P S L T T Q   323
HMSGp3   G R - - - - - P S - - - I K D E V A L L A L L S K S D - - - A Q   317
HMSG11   G R - - - - - Q H - - - V R D A T A L L A L L L K - - - - - - K   327
HMSG14   G R - - - - - Q H - - - V R D A T A L L A L L L K - - - - - - K   327
HMSG32   G K - - - - - P P - - - V R D A T A L L A L L I Q N L D P - - K   332
HMSG33   G K - - - - - H H - - - L R D A T A L L T L L V K K D D T G K N   318
HMSG35   G K - - - - - N H - - - L R D A T A L L A L L I Q - D S S L K K   317
GBHMSG   G K - - - - - P P - - - V R D A T A L L A L L I Q N P D P K I Q   330

RMSGGP3  K E P D K K C T K A L E K C D A S K Y L N T E L E K L C K D G -   346
HMSGp1   R T N K E K C K K I L E D K C K N L K E H D I I K G L C E D Y N   355
HMSGp3   N T F K D Q C E D V I K K K C G N F K E H I I L K D L C S N K T   349
HMSG11   T L K K E E C I K A L K K N C E N P H E H E A L E N L C K E N K   359
HMSG14   T L K K E E C I K A L K K N C E N P H E H E A L E N L C K E N K   359
HMSG32   S Q V G K E C E K V L K D N C K E L K S H E I L G D F C N Q N V   364
HMSG33   N N I G E K C N K I L E D K C K N S Q Q H E A L K N L C N N N S   350
HMSG35   K D D K E K C E E A L Q K S C K N P H E H E A L E S L C K K N G   349
GBHMSG   A N E K E K C K K V L E N K C K E L K K H E V L G D L C N Q N A   362
```

FIGURE 1D

```
RMSGGP3  - - - N K N E K C K K I L - D V K E R C T N L K L K L Y L K G L   374
HMSGp1   A N K D K D K K C E E L S T D I E E T C K F F I S K T L M I H F   387
HMSGp3   I T D N P K E K C E E L N K E L T T R I L T V S K R I E K Y F A   381
HMSG11   P S S D G T K K C D E L E K D V N K T C T S L T S T I L K N R L   391
HMSG14   P S S D G T K K C D E L E K D V N K T C T S L T S T I L K N R L   391
HMSG32   A G Q N E I E K C K E L E K E L A N S T K I L F E K I K N K H L   396
HMSG33   P N A Y G K E K C K E L E E D I K K T C T N L K P T I L K N H L   382
HMSG35   L S N D G T K K C E E L Q N D I N K T C K I F T S K V T N N R L   381
GBHMSG   A S Q S G T K K C E E L E K E L A N S T K I L S E K I K N K H L   394

RMSGGP3  S T E Y D D Q E S D P L S W G Q L P T F F I K G E C A E L E S E   406
HMSGp1   F G D G N - K N D G I I K W G N L S T F L S N K D C T K L E S Y   418
HMSGp3   P A N - - - - V K E I I G W H M L H T F L G E R E C T K L L S D   409
HMSG11   Y I S - - - - P D G I A E W G K L P T F L S D E D C A K L E S Y   419
HMSG14   Y I S - - - - P D G I A E W G K L P T F L S D E D C A K L E S Y   419
HMSG32   S G S - - - - - G E V I P W Y K L T T F L S D N D C T R L E S D   423
HMSG33   Y D P - - - - N D K I V E W R K L P T F L T N E D C A R L E S Y   410
HMSG35   F D P T K - G N N E I V G W E G L P T F L S N E D C A K L E S Y   412
GBHMSG   S G S - - - - - G E T I P W Y K L S T F L S D S D C A R L E S D   421

RMSGGP3  C F Y L E K A C K D N N I D K A C Q N A R A A C Y K K G Q D R M   438
HMSGp1   C L Y F E K S C R - - - S E T A C K N I R A A C Y K R G L D T L   447
HMSGp3   C F Y L K S Q A P - - - L E K P C N N L K A A C Y K K G L E A V   438
HMSG11   C F Y Y K E T C P D - - V K E A C M N V R A A C Y K R G L D A R   449
HMSG14   C F Y Y K E T C P D - - V K E A C M N V R A A C Y K R G L D A R   449
HMSG32   C F Y L K S Q A P - - - L D K E C N N L K A A C Y K R G L E A Q   452
HMSG33   C F Y Y E K A C P N - - A K E E C M N L R A A C Y K R G L D G R   440
HMSG35   C F Y F E K K C P D - - G E N A C K N I R A T C Y K R G L D A R   442
GBHMSG   C F Y F A Q D K D P - - L K K E C K N V K A A C Y K R G L D A R   451
```

FIGURE 1E

| | | |
|---|---|---|
| RMSGGP3 | L N K F F Q K E L K G K L G H V R F Y S D P K D C K K Y V V E N | 470 |
| HMSGp1 | A N E V L Q K E M R G M L H G S - N K T W L S G F Q K K L I E V | 478 |
| HMSGp3 | A N E A L Q D K L R G K L Q G S - N R T W L E T L Q K N L V K V | 469 |
| HMSG11 | A N S V L Q K N M R G L L H G S - N K D W L K K F Q Q E L A K V | 480 |
| HMSG14 | A N S V L Q K N M R G L L R G S - N Q S W L K E F Q Q R L V K V | 480 |
| HMSG32 | A N E A L Q K K M Y G L E Y G S [illegible] C K E W F K K D L E K L M E E | 483 |
| HMSG33 | A N K V L Q E N M R G L L R G S - N Q S W L K E F Q Q R L V K V | 471 |
| HMSG35 | A N K V L Q E N M R G M L H G S - N K S W L E K F Q Q E L V K V | 473 |
| GBHMSG | A N K V L Q E N M R G L L R G S - N Q S W L K K F Q Q E L V K V | 482 |

| | | |
|---|---|---|
| RMSGGP3 | C T K L D - - - - - - - - - K - K Y L P R C L Y P K E L C Y G L S | 493 |
| HMSGp1 | C K K V K K E N K G V F P S N E L F V L C V Q P S K A A R L L S | 510 |
| HMSGp3 | C E K T K - - - - - - G E S D E L F V L C M N P I K T A L T V S | 495 |
| HMSG11 | C E K L K - G N K G S F S N D E L F V L C T Q P A K A A R L L T | 511 |
| HMSG14 | C K E L K - E N K G S F P N D E I F V L C V Q P A K A A R L L T | 511 |
| HMSG32 | C S E L K - - - - - - T T S D E L F L L C I D P L K A V R I L A | 509 |
| HMSG33 | C K E L K - E N K G S F P N D E I F V L C V Q P A K A A R L L T | 502 |
| HMSG35 | C E K L K K E N K G S F S N D E L F I L C V Q P A K A A R L L T | 505 |
| GBHMSG | C E K L K E E N K G S F S N D E L F V L C V Q P A K A A R L L T | 514 |

| | | |
|---|---|---|
| RMSGGP3 | N D T F L Q S K E L S A L L D D Q R D F P L K K D C V E L K E K | 525 |
| HMSGp1 | H D L R M K T I F L Q D D L N R K R D F P V K E D C E E L L K K | 542 |
| HMSGp3 | T D L R M R A V A L Q E H L N E K R D F P T E K D C K E L E K K | 527 |
| HMSG11 | H H H Q M R V I F L R Q Q L D Q K R D F P T D K D C K E L G R K | 543 |
| HMSG14 | H D H Q M R V T F L R Q Q L D Q K R D F P T D K D C K E L G K K | 543 |
| HMSG32 | A D I Q A R A V F L R K Q L D Q K R D F P T D K D C K E L G R K | 541 |
| HMSG33 | H D H Q M R V I F L R Q Q L D Q K R D F P T D K D C K E L G K K | 534 |
| HMSG35 | H D L R M K T I F L R Q Q L D Q K R D F P T D K N C K E L G R K | 538 |
| GBHMSG | H D L R M T T I F L R Q Q L D Q K R D F P T V K T A K G I R E K | 546 |

FIGURE 1F

RMSGGP3 C D E L S S - D S L L N L E K C I T L K R R C E Y F R V S E G F 556
HMSGp1 C E A L R K - D S K K I E W P C H T L S Q N C D Q L R N A K E L 573
HMSGp3 C E V L G K - D S R E I K W S C Y T L K Q H C N R L K S I E H L 558
HMSG11 C Q D L G K - D S K E I T W P C H T L E Q Q C N R L G I T E I L 574
HMSG14 C Q D L G K - D S K E I T W P C H T L E Q Q C N R L G T T E I L 574
HMSG32 C E A L G K - D S N Q I K W P C H T L K Q Q C D R L G T T E I L 572
HMSG33 C Q D L G K - D S K E I T W P C H T L E Q Q C N R L G T T E I L 565
HMSG35 C Q D L G E - D S K E I T W P C H T L E Q Q C N R L G T T E I L 568
GBHMSG C Q D L G K G F Q K E I T W P C H T L E Q Q C N R L G T T E I L 578

RMSGGP3 R N V F L E K K D D S L M T Q D N C T K A L H E K C H Q L Y R R 588
HMSGp1 K E L L L N E H K D I L K N Q E N C G M Y L K E K C N E W S R R 605
HMSGp3 E E E L L K E N K G Y L K D E N S C K E E A K K R C E K W F R R 590
HMSG11 K Q I L L D E H K D T L K S H E N C A K Y L K R K C H K W S R R 606
HMSG14 K Q V L L D E H K D T L K D Q E S C V K Y L K E K C N K W S R R 606
HMSG32 K Q V L L D E H K D T L R T H E N C T K Y L K R K C H K W S R R 604
HMSG33 K Q V L L D E H K D T L K D Q E S C V K Y L K E K C N K W S R R 597
HMSG35 K Q V L L D E H K D T L K D Q E S C V K Y L K E K C N K W S R R 600
GBHMSG K Q V L L N E H K D T L K T H E N C V T Y L K E K C N K W S R R 610

RMSGGP3 R K N S F S V S C A L P E E T C S Y M V F H T S Q D C S S L K V 620
HMSGp1 R N E R F S L L C A L Q N R T C R I M V E D V K N Q C K I F E K 637
HMSGp3 E N N K F F S A C S D L E L V C K K I T R N V E S K C N I L K G 622
HMSG11 G D D R F S F V C V F Q N A T C E L M V K D V Q D R C K I F E E 638
HMSG14 G D D R F S F V C V F Q N A T C E L M V K D V K D R C E V F K K 638
HMSG32 G D D R F S F V C V Y Q N A T C K L I V D D V K D R C E V F E K 636
HMSG33 G D D R F S F V C V F Q N A T C E L M V K D V K D R C E V F K K 629
HMSG35 G D D R F S F V C V F Q N A T C E L M V K D V K D R C E V F K K 633
GBHMSG G D D R F S F V C V F Q N A T C K L M V K D V Q D R C K I F K E 642

FIGURE 1G

```
RMSGGP3  N I K N E K I L E K I G E E I K K A N K N E A L V E E L C T T W   652
HMSGp1   N I K K Y Q G I D S K T K I - - - - E E - - - - L G T Y C P I W   661
HMSGp3   H M E T M N V I S E I A K K - - - - - - - - - - E E K I C E F W   644
HMSG11   N M Q A S D I N D S L K K N Q I K A E S - - - - A A N I C P S W   666
HMSG14   N I K A S Y I I E F L E N N T N K I T T - - - - L E R N C P S W   666
HMSG32   N M Q A S D I N N S L K N K Q I K T E S - - - - A A N I C P S W   664
HMSG33   N I K A S Y I I E F L E N N T N K I T T - - - - L E R N C P S W   657
HMSG35   N I K A S Y I I E F L E N N T N K I T T - - - - L E R N C P S W   660
GBHMSG   N I K V S E I V D F L K N N T N N I T T - - - - L E R N C P S W   670

RMSGGP3  G R H C H Q L M E N C P D D L K K K E N G N G N D H N C E A L Q   684
HMSGp1   H P H C H R F G P N C P D L E K - - - - - - - - - N K C E D F E   684
HMSGp3   A P Y C K K Y E Q N C E K L K N G G K - - - - - - D G Q C K K L N   671
HMSG11   H P Y C D R F L P N C P D L K K G - - - - - - - - K T F C Q N L K   691
HMSG14   H T Y C N R F S P N C P G L T K - - - - - - - - - E N S C T K I K   690
HMSG32   H P Y C D R F L P N C P D L K K G - - - - - - - - K T F C Q N L K   689
HMSG33   H T Y C N R F S P N C P G L T K - - - - - - - - - E N S C T K I K   681
HMSG35   H T Y C N R F S P N C P G L T K - - - - - - - - - E N S C T K I K   684
GBHMSG   H T Y C N R F S S N C P D F S K - - - - - - - - - K N P C T K I K   694

RMSGGP3  E K C N K T F E K L K L E E E L S H L L K G S L K D - D K C K E   715
HMSGp1   K Y C K P Y Y K Q R D L E N A L I F E F R G H L D K K K N C K T   716
HMSGp3   K K C K S F L E K E A L E N K V V E E L K G S L S N V G E C N N   703
HMSG11   K Y C E P F Y K R K V L E D A L K V E L R G N L S N I T K C E P   723
HMSG14   K H C E P F Y K R K A L E D A L K V E L Q G K L T D K S K C E P   722
HMSG32   K Y C E P F Y K R K V L E D A L K V E L Q G N L S N R N K C E S   721
HMSG33   K H C E P F Y K R K A L E D A L K V E L Q G K L T D K S K C E P   713
HMSG35   K H R E P F Y K R K A L E D A L K V E L Q G K L T D K S K C E P   716
GBHMSG   N N C K P F Y E R K A L E D A L K V E L R G K L S D E N K C T A   726
```

FIGURE 1H

```
RMSGGP3  A L G K R C T E L E K N E A F K T L Y G K C D D N T - - - - - -   741
HMSGp1   N L D K Y C T L W D Q T G N K T - L K G F C N S S T D - - - N N   744
HMSGp3   T L N I Y C T Q L K K A E N G - - L E T L C K S K E - - - N T K   730
HMSG11   A L E R Y C T V L K D V N N A S - I S S L C K D N T E S K T K K   754
HMSG14   A L N R Y C T V A G N V N N A S - I S G L C K A N T K D N S G K   753
HMSG32   A L E R Y C T I L K N V S D S S - I N S L C K D N T E S K T K K   752
HMSG33   A L K R Y C T V A G N V N N A S - I S G L C K A N T K D N S G K   744
HMSG35   A L K R Y C T V A G N V N N A S - I S G L C K A N T K D N S G K   747
GBHMSG   A L K G Y C T L A G N V N N A S - V R S L C K D N T Q G S N K K   757

RMSGGP3  K E - - - - - - N V C K K L V D K V K K R C P T L K D E L E N A   767
HMSGp1   E T - - - F R D K L C E K L V Q R V K E K C Q G L S K E L E K A   773
HMSGp3   S D - I K V R E E L C E K L I K R I K E K C S K L K D E L E E V   761
HMSG11   A D N K N V R K K L C L K L V E E V E Q Q C K V L P T E L T E L   786
HMSG14   S D - E D A R K E L C E K S V K E V E E Q C K A L P T E L G Q P   784
HMSG32   T D - N E V R K K L C L K L V E E V E Q Q C K M L P A E L E H E   783
HMSG33   S D - E D A R K E L C E K L V K E V E E Q C K A L P T E L G Q P   775
HMSG35   S D - E D A R K E L C E K L V K E V E E Q C K A L P T E L G Q P   778
GBHMSG   T D - E K V V E E L C K K L M E E V K E Q C E T L P A E L K Q P   788

RMSGGP3  K K E L T K M K N E Y D D L K K A A E K S T E A A K L L L S R P   799
HMSGp1   K N D L E E K H K D Y E K V K K D T K N A M E E T N L V F S T T   805
HMSGp3   K E V L E K K E E K Y K K I K E E A E K A M E D A N L I L S R A   793
HMSG11   E K S L K K D V K T Y E E L K E R A K K A M N K S S L V L S L V   818
HMSG14   A A D L K K D Y K T Y E E L K K R A E E A M N K S S L V L S L I   816
HMSG32   E K D L K D D F E T F E K L K K Q A E K T M N K S N L V L S F V   815
HMSG33   A A D L K K D Y K T Y E E L K K R A E E A M N K S S L V L S L I   807
HMSG35   A A D L K K D Y K T Y E E L K K R A E E A M N K S S L V L S L I   810
GBHMSG   A D D L E K D V K T Y E E L K E E A K K A M N K S S L V L S F V   820
```

FIGURE 1I

```
RMSGGP3  R Q T V M P N A Q N G S D S T L V P P P P Q A P A G P P P P G S  831
HMSGp1   K - - - - S T D N K T E K G - V K P S T - - - - - - - - - - - -  820
HMSGp3   K - - - - G P D N N N N K - - S V N K D - - - - - - - - - - - -  807
HMSG11   K - - - - K N E S N T S K N N S K N K D - - - - - - - - - - - -  834
HMSG14   K - - - - K N E S N V S K S N S K N K D - - - - - - - - - - - -  832
HMSG32   K - - - - K D E N N T S K N S S K D K D - - - - - - - - - - - -  831
HMSG33   K - - - - K N E S N V S K S N S K N K D - - - - - - - - - - - -  823
HMSG35   K - - - - K N E S N V S K S N S K N K D - - - - - - - - - - - -  826
GBHMSG   K - - - - K D G N N T P K N N S K S E D - - - - - - - - - - - -  836

RMSGGP3  P P P P P S Q N G T P G T P G G E T G A S G G T P G T P G T P G  863
HMSGp1   - - P S V V Q D - - - - - - - - - - - - - - - - - - - - - - - -  826
HMSGp3   - - S S D T P K - E G K G - - - - - - - - - - - - - - - - - - -  817
HMSG11   - - K N V V S N G L Q D T - - - - - - - - - - - - - - - - - - -  845
HMSG14   - - K N A V S N G L Q D T - - - - - - - - - - - - - - - - - - -  843
HMSG32   - - K N T V S N G L Q D T - - - - - - - - - - - - - - - - - - -  842
HMSG33   - - K N A V S N G L Q D T - - - - - - - - - - - - - - - - - - -  834
HMSG35   - - K N A V S N G L Q D T - - - - - - - - - - - - - - - - - - -  837
GBHMSG   - - K N V V S N - E K D T - - - - - - - - - - - - - - - - - - -  847

RMSGGP3  T P G T P G G M M K Y A K L G L V K R T Y V D G G V S E V E V K  895
HMSGp1   - - - - - - - - - - I V H F K L V K R N E K - V Q V T E K E A K  847
HMSGp3   - - - - - - - - - - T T G F K L V R R N A K - V H V T E K E L A  838
HMSG11   - - - - - - - - - - T K Y V K I L R R G V K E A L V T E S E A K  867
HMSG14   - - - - - - - - - - T K H V K I L R R G V K D V S V T E L E A K  865
HMSG32   - - - - - - - - - - T E H M K I L R R G V K D V S V T E S E A K  864
HMSG33   - - - - - - - - - - T K H V K I L R R G V K D V S V T E L E A K  856
HMSG35   - - - - - - - - - - T K H V K I L R R G V K D V S V T E L E A K  859
GBHMSG   - - - - - - - - - - I K H V K I L R R G V K D V L V T E L E A K  869
```

FIGURE 1J

```
RMSGGP3  A F D A T T I A L E L Y L E L K E E C K A L E L D C G F K E D C   927
HMSGp1   A F D L V A L A F S L Y V E L K E T C H H L K D D C E F R K E C   879
HMSGp3   A F D L V A R A F D L Y L E L K E I C N H S L K N C G F K K E C   870
HMSG11   A F D L A A E V F G R Y V D L K E K C E K L T S D C G I K D D C   899
HMSG14   A F D L A A E V F G R Y V D L K E R C N K L E S D C R I K E D C   897
HMSG32   A F D L V A E V F G R Y L D L K E R C N K L E S D C R V K E D C   896
HMSG33   A F D L A A E V F G R Y V D L K E R C N K L E S D C R I K E D C   888
HMSG35   A F D L A A E V F G R Y V D L K E R C N K L E S D C R I K E D C   891
GBHMSG   A F D L A A E V F G R Y V D L K E R C E K L T L D C G I K D D C   901

RMSGGP3  P D T K Q A C E N I D T L C K - L E P L E I K P H H T E K I T E   958
HMSGp1   K - C K D Q C K E I E K I C L K I E P L K V K P H E I K T V T E   910
HMSGp3   D - C E D P C K K I Q G I C S T L E P L K V R P H E I V T K N I   901
HMSG11   D G L K E V C G K I E K T C H D L K P L E V K S H E I V T E - -   929
HMSG14   K D L E E V C K K I N K A C R N L K P L E V K P H E T V T E - -   927
HMSG32   K D L E G V C G K I Q G V C S K L K P L K V K P H E T V T E - -   926
HMSG33   K D L E E V C K K I N K A C R N L K P L E V K P H E T V T E - -   918
HMSG35   K D L E E V C K K I N K A C R N L K P L E V K P H E T V T E - -   921
GBHMSG   D G L K G V C G K I K K K C R D L K P L E V K S H E I V T E - -   931

RMSGGP3  T K T E T K T E T K T E T K T D G K A D E K T V E K T V T E T K   990
HMSGp1   - - T N I T T V T E T V K E A E K T V G D G - - - - - - - - - -   930
HMSGp3   - - T T T T T T T T T T I K D A K A T - - - - - - - - - - - - -   919
HMSG11   - - S T T T T T T T T T T V T D P K A T - - - - - - - - - - - -   947
HMSG14   - - G T T T T T T T T T T V A D P K A T - - - - - - - - - - - -   945
HMSG32   - - S T T T T T T T T T T V T D P K A T - - - - - - - - - - - -   944
HMSG33   - - S T T T T T T T T T T V A D P K A T - - - - - - - - - - - -   936
HMSG35   - - S T T T T T T T T T T V A D P K A T - - - - - - - - - - - -   939
GBHMSG   - - S T T T T T T T T T T V T D P K A T - - - - - - - - - - - -   949
```

FIGURE 1K

```
RMSGGP3  S V G G G K V T E E C T M I Q T T D T W V T S T S L H T S T T T  1022
HMSGp1   - - - - - - - - E K C K S L S T T D T W V T K T S T H T S T S T   954
HMSGp3   - - - - - - - - - D C H S L Q T T D T W V T K T S T H T S T S T   942
HMSG11   - - - - - - - - - E C K S L Q T T D T W V T Q T S T H T S T S T   970
HMSG14   - - - - - - - - - E C K S L Q T T D T W V T Q T S T H T S T S T   968
HMSG32   - - - - - - - - - E C K S L Q T T D T W I T Q T S T H T S T S T   967
HMSG33   - - - - - - - - - E C K S L Q T T D T W V T Q T S T H T S T S T   959
HMSG35   - - - - - - - - - E C K S L Q T T D T W V T Q T S T H T S T S T   962
GBHMSG   - - - - - - - - - E C K S L Q T T D T W V T Q T S T H T S T S T   972

RMSGGP3  S T S T V T S T V T L T S M R K C K P T K C T T D S S K E T Q K  1054
HMSGp1   T T S T V T S R I T L T S T R R C K P T K C T T G E - - - - - -   980
HMSGp3   T T S T V T S R I T L T S T R R C K P T K C T T G E - - - - - -   968
HMSG11   I T S T I T S K I T L T S T R R C K P T K C T T G - - - - - - -   995
HMSG14   I T S T I T S K I T L T S T R R C K P T K C T T G - - - - - - -   993
HMSG32   I T S T I T S K I T L T S T R R C K P T K C T T G - - - - - - -   992
HMSG33   I T S T I T S K I T L T S T R R C K P T K C T T G - - - - - - -   984
HMSG35   I T S T I T S K I T L T S T R R C K P T K C T T G E - - - - - -   988
GBHMSG   I T S T I T S K I T L T S T R R C K P T K C T T G - - - - - - -   997

RMSGGP3  E E D D E E V K P N E G M K I R V P D M I K I M L L G V I V M G  1086
HMSGp1   E D E A G E V K P S E G L R M S G W S V M R G V L L A M M I S F  1012
HMSGp3   E D E A G D V K P S E G L R M S G W S V M R G V L L A M T I S F  1000
HMSG11   - D E A G D V K P S E G L K M S G W S V M R G V I V A M V I S F  1026
HMSG14   - D D A E D V K P S E G L R V S G W N V M R G V I V A M V I S F  1024
HMSG32   - D D A E D V K P S E G L K M S G - - - - - - - - - - - - - - -  1008
HMSG33   - D D A E D V K P S E G L R V S G W N V M R G V I V A M V I S F  1015
HMSG35   E D D A G D V K P S E G L R M S G W N V M R G V I V A M V I S F  1020
GBHMSG   - D D A E D V K P S E G L R V S G W N V M R G A I V A M V I S F  1028
```

FIGURE 1L

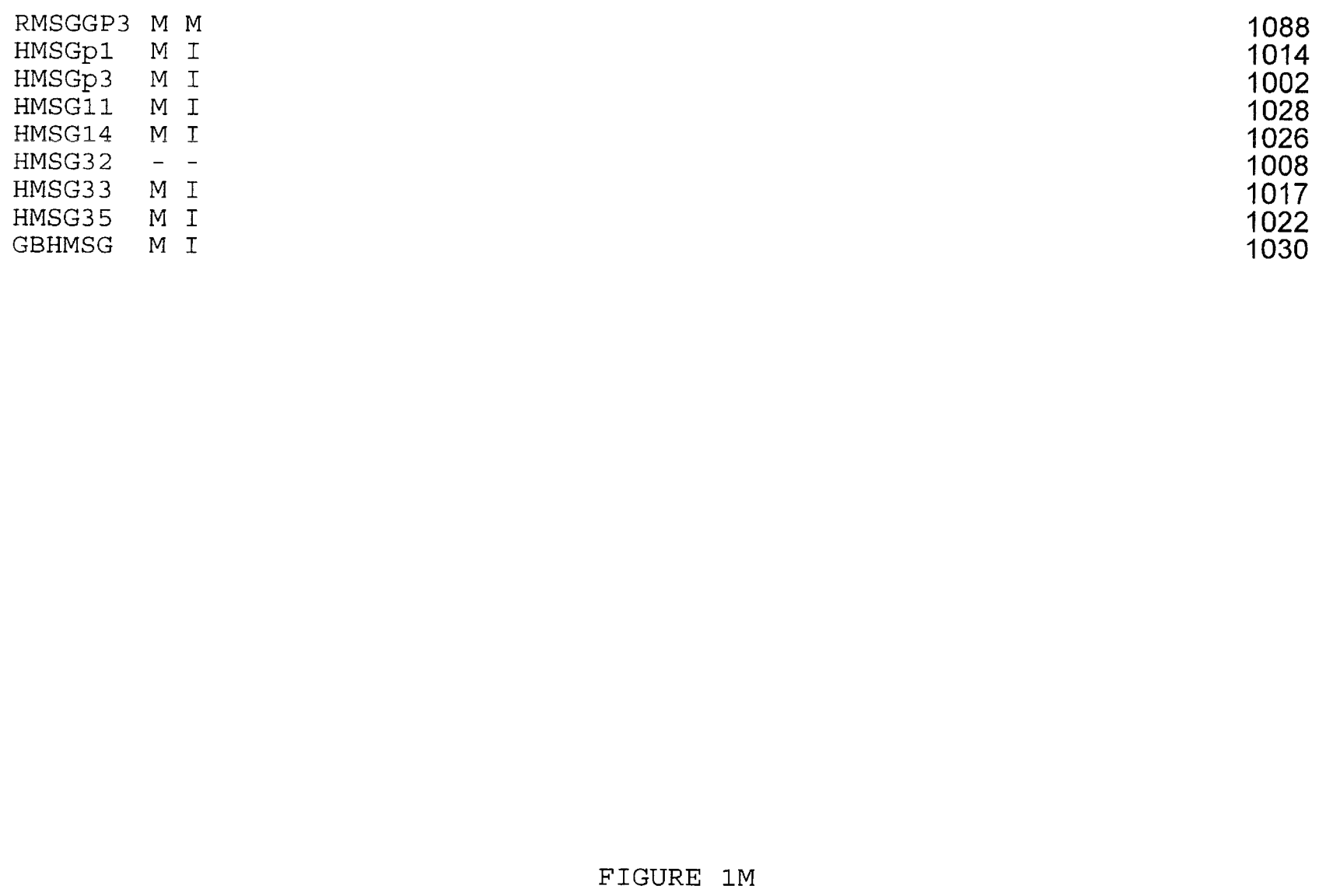

```
RMSGGP3  M M     1088
HMSGp1   M I     1014
HMSGp3   M I     1002
HMSG11   M I     1028
HMSG14   M I     1026
HMSG32   - -     1008
HMSG33   M I     1017
HMSG35   M I     1022
GBHMSG   M I     1030
```

FIGURE 1M

IDENTIFICATION OF A REGION OF THE MAJOR SURFACE GLYCOPROTEIN (MSG) GENE OF HUMAN *PNEUMOCYSTIS CARINII*

REFERENCE TO RELATED CASES

This application claims priority to International Application No. PCT/US99/18750, filed Aug. 17, 1999, which claims the benefit of U.S. Provisional Application No. 60/096,805, filed Aug. 17, 1998.

FIELD OF THE INVENTION

This invention relates to methods for detecting *Pneumocystis carinii* infection in humans, specifically to such methods that involve polymerase chain reaction or other amplification of nucleic acid sequences that encode a *Pneumocystis carinii* sp. f. hominis protein.

BACKGROUND OF THE INVENTION

*Pneumocystis carinii* is an important life threatening opportunistic pathogen of immunocompromised patients, especially those with human immunodeficiency virus (HIV) infection. Conventional diagnosis of *Pneumocystis carinii* pneumonia (PCP) involves analysis of a tissue sample or oropharyngeal secretion sample for the presence of a *P. carinii* organism through staining and microscopic examination. Sample acquisition techniques have included such invasive methods as transbronchial biopsy, percutanenous lung biopsy, or open lung biopsy. Each of these techniques is fraught with possible complications and requires significant time and expense. In the mid 1980's, bronchoalveolar lavage (BAL) was introduced as a less invasive, less expensive, and less complication-prone technique for acquiring samples to be used in PCP diagnosis (Ognibene et al. (1984) *Am. Rev. Respir. Dis.* 129:929–932). However BAL, coupled with bronchoscopy, still required special equipment and facilities, as well as the time of a physician and technician. Simpler still, it is now known that the Pneumocystis organism can also be detected in induced sputum samples (Bigby et al. (1986) *Am. Rev. Respir. Dis.* 133:515–518; Kovacs et al. (1988) *NEJM* 318:589–593).

Advances also have occurred in the techniques used to detect the Pneumocystis organism in tissue and oropharyngeal secretion samples. Direct microscopic examination of clinical samples stained with, for instance, Giemsa stain or toluidine blue O, requires time-consuming sample preparation and subsequent examination by specially trained and experienced microscopy technicians (see, for instance, Bigby et al. (1986) *Am. Rev. Respir. Dis.* 133:515–518). This procedure has been somewhat simplified and rendered more amenable to mechanization through the use of monoclonal antibodies in detection of *P. carinii* antigens in clinical samples (Kovacs et al. (1988) *NEJM* 318:589–593). A few groups have used oligonucleotide probes complementary to *P. carinii* nucleotide sequences to detect the organism through hybridization, as in U.S. Pat. No. 5,164,490 (the Santi patent).

Polymerase chain reaction (PCR) -mediated amplification of DNA or RNA-encoding sequences has been used to diagnose various diseases including leprosy (Santos et al. (1997) *J. Med. Microbiol.* 46:170–172) and PCP. This technique exhibits increased sensitivity over simple probe hybridization methods. Primers complementary to sequences encoding *P. carinii* mitochondrial or chromosomal ribosomal RNA (rRNA) have been used to amplify Pneumocystis-specific DNA sequence, as in Wakefield et al. (1990) *Mol. Biochem. Parasit.* 43:69–76; Wakefield et al. (1990) *Lancet* 336:451453; Lipschik et al. (1992) *Lancet* 340:203–206; WO 91/19005; and U.S. Pat. Nos. 5,519,127 (the Shah patent), 5,593,836 (the Niemiec patent) and 5,776,680 (the Leibowitz patent).

Other recent research advances relate to elucidating the molecular mechanisms involved in *P. carinii* infection. A great deal of interest has focused on the major surface glycoprotein (MSG; also called glycoprotein A) of *P. carinii*, because it is considered to be both a virulence factor and a target of host immune responses. MSG is the most abundant protein expressed on the surface of *P. carinii*, as assessed by Coomassie blue staining. It appears to play a critical role in the pathogenesis of pneumocystosis, possibly by acting as an attachment ligand to lung cells. MSG is also a target of both humoral and cellular immune responses by the host.

Multiple genes encode the MSG of rat-*P. carinii*, and different MSGs may be expressed in the lung of a rat infected with *P. carinii* (Angus et al. (1996) *J. Exp. Med.* 183:1229–1234; Kovacs et al. (1993) *J Biol. Chem.* 268:6034–6040). Similarly, multiple genes encode the MSG of *P. carinii* infecting ferrets and mice (Haidaris et al. (1998) *DNA Res.* 5:77–85; Haidaris et al. (1992) *J. Infect. Dis.* 166:1113–1123). Additional studies have shown that there is a single genomic site for expression of rat MSG variants (Edman et al. (1996) *DNA Cell Biol.* 15:989–999; Sunkin and Stringer (1996) *Mol. Microbiol.* 19:283–295; Wada and Nakamura (1996) *DNA Res.* 3:55–64; Wada et al. (1995) *J. Infect. Dis.* 171:1563–1568). These studies suggest that *P. carinii* has developed an elaborate system for antigenic variation, presumably to evade host defense mechanisms.

Molecular and immunological studies have clearly demonstrated that *P. carinii* isolated from different host species are distinct organisms, and may in fact be separate species (Gigliotti (1992) *J. Infect. Dis.* 165:329–336; Keely et al. (1994) *J. Eukaryot. Microbiol.* 41:94S; Kovacs et al. (1989) *J. Infect. Dis.* 159:60–70; Stringer (1993) *Infect. Agents Dis.* 2:109–117). There is a high level of variation among orthologous genes, including the MSG genes, isolated from different host-specific strains of the Pneumocystis. Hence, diagnosis of *P. carinii* infection in human patients ideally requires *P. carinii* sp. f. hominis (hereinafter "human-*P. carinii*") derived reagents.

The cloning of human-*P. carinii* MSG genes has recently been reported (Garbe and Stringer (1994) *Infect. Immun.* 62:3092–3101; Stringer et al. (1993) *J. Eukaryot. Microbiol.* 40:821–826); however, only one full-length sequence was reported.

SUMMARY OF THE INVENTION

The inventors have discovered that human-*P. carinii* MSG is encoded for by a large, highly-conserved gene family, with a particularly conserved region of about 100 amino acids in the C-terminal region of the proteins. The have further discovered that direct detection or nucleic acid amplification (e.g., PCR amplification) of human-*P. carinii* MSG-encoding genes provides a particularly sensitive and specific technique for the detection of *P. carinii*, and the diagnosis of PCP.

This invention encompasses the purified novel human-*P. carinii* proteins represented by SEQ ID NO: 2, SEQ ID NO: 4, SEQ ID NO: 6, SEQ ID NO: 8, SEQ ID NO: 10, SEQ ID NO: 12, and SEQ ID NO: 14, and isolated nucleic acid molecules that encode these proteins. Specific nucleic acid molecules encompassed in this invention include those represented in SEQ ID NO: 1; SEQ ID NO: 2; SEQ ID NO:

3; SEQ ID NO: 4, SEQ ID NO: 5; SEQ ID NO: 6, SEQ ID NO: 7; SEQ ID NO: 15; and SEQ ID NO: 17. Also encompassed within this invention are the isolated nucleic acid sequences that encode the carboxy-terminal conserved about 100 amino acids of the disclosed human-*P. carinii* MSGs; these may be used for amplification or as probes. The sequences of these conserved nucleic acid molecule regions include residues 2794–3042 of HMSGp1 (SEQ ID NO: 1), 2758–3006 of HMSGp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), 2821–3072 of HMSG35 (SEQ ID NO: 13), or 1–249 of HMSGp2 (SEQ ID NO: 15). In addition, this invention encompasses sequences with at least 70% sequence identity to these regions, and recombinant vectors comprising such nucleic acid molecules and conserved regions from within such nucleic acid molecules, as well as transgenic cells including such a recombinant vector.

Another aspect of this invention provides a method of detecting the presence of *Pneumocystis carinii* in a biological specimen, by amplifying with a nucleic acid amplification method (e.g., the polymerase chain reaction) a human-*P. carinii* nucleic acid sequence using two or more oligonucleotide primers derived from a human-*P. carinii* MSG protein encoding sequence, then determining whether an amplified sequence is present. In a preferred embodiment of this invention, the human-*P. carinii* nucleic acid sequence is a highly conserved region within an MSG-protein encoding sequence. Such a highly conserved region may, for instance, include residues 2794–3042 of HMSGp1 (SEQ ID NO: 1), 2758–3006 of HMSGp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), 2821–3072 of HMSG35 (SEQ ID NO: 13), or 1–249 of HMSGp2 (SEQ ID NO: 15). A further aspect of this invention is the method of detecting the presence of *Pneumocystis carinii* in a biological specimen, by determining whether an amplified sequence is present, for instance by electrophoresis and staining of the amplified sequence, or hybridization to a labeled probe of the amplified sequence. Appropriate labels for the hybridization probe include a fluorescent molecule, a chemiluminescent molecule, an enzyme, a co-factor, an enzyme substrate, or a hapten. The nucleotide sequence of such a probe can be chosen from any MSG gene sequence that is amplified in the detection method, and for instance can include a nucleic acid sequence according to SEQ ID NO: 19.

Another aspect of this invention is a method of detecting the presence of *Pneumocystis carinii* in a biological specimen by exposing the biological specimen to a probe that hybridizes to a human-*P. carinii* nucleic acid sequence derived from a human-*P. carinii* MSG protein encoding sequence. The labeled probe to be used in this method may, for instance, include the nucleic acid sequence of SEQ ID NO: 19.

This invention also encompasses one or more oligonucleotide primers including at least 15, or at least 20, 25, 30, 35, 40, 50, or 100, contiguous nucleotides from any of the highly conserved regions within an MSG-protein encoding sequence disclosed herein, or from any nucleic acid sequences having at least 70%, or at least 90% or 95%. sequence homology with these sequences. Specific examples of such oligonucleotide primer sequences are shown in SEQ ID NO: 17, SEQ ID NO: 18, SEQ ID NO: 19, SEQ ID NO: 20, SEQ ID NO: 23, and SEQ ID NO: 24. Of these primers, SEQ ID NO: 17, SEQ ID NO: 18, SEQ ID NO: 19, and SEQ ID NO:23 may serve as upstream primers, while SEQ ID NO: 20 and SEQ ID NO: 24 may serve as down stream primers.

Kits for detection of a human-*P. carinii* nucleic acid sequence are another aspect of this invention. Such kits may include at least a pair of primers each comprising at least 15, or at least 20, 25, 30, 35, 40, 45, 50, or 100 contiguous nucleotides of any of the conserved regions of the herein disclosed MSG-encoding sequences, and homologs having at least 70% identity with such sequences. Representative primers include those represented by the nucleotide sequences of SEQ ID NO: 17; SEQ ID NO: 18; SEQ ID NO: 19; SEQ ID NO: 20; SEQ ID NO: 21; SEQ ID NO: 22; SEQ ID NO: 23; and SEQ ID NO: 24. These kits may further including a positive nucleic acid amplification (e.g., PCR) control sequence.

Antibodies raised to the peptide sequence according to SEQ ID NO: 25 or SEQ ID NO: 26 are also included within the scope of this invention.

The foregoing and other objects, features, and advantages of the invention will become more apparent from the following detailed description of several embodiments. which proceeds with reference to the accompanying figure and tables.

BRIEF DESCRIPTION OF THE DRAWINGS

FIG. 1A–1M is an alignment of the deduced amino acid sequences encoded by two of the human-*P. carinii* MSG genes contained in the genomic clone (HMSGp1, SEQ ID NO: 2: and HMSGp3, SEQ ID NO: 4) and the five genes generated by PCR (HMSG11, SEQ ID NO: 6; HMSG14, SEQ ID NO: 8; HMSG32, SEQ ID NO: 10; HMSG33, SEQ ID NO: 12 and HMSG35. SEQ ID NO: 14), together with a published sequence (GBHMSG) and a rat-*P. carinii* MSG sequence (RMSGGP3, GenBank accession number: L05906). A methionine was substituted for valine at position 1 in the PCR clones during amplification to facilitate expression, and thus is excluded from the alignment. The peptides that were synthesized and used to generate anti-peptide antibodies are shaded in light grey in FIG. 1L (conserved epitope) or dark grey (HMSG32-specific epitope). The arrows (FIG. 1L) flank the conserved region that was expressed in pET28a. The conserved carboxy-terminal region of the proteins is boxed (FIG. 1L).

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the nucleic acid sequence of MSG HMSGp1, GenBank Accession No: AF038556.

SEQ ID NO: 2 shows the amino acid sequence of MSG protein HMSGp1.

SEQ ID NO: 3 shows the nucleic acid sequence of MSG HMSGp3, GenBank Accession No: AF038556.

SEQ ID NO: 4 shows the amino acid sequence of MSG protein HMSGp3.

SEQ ID NO: 5 shows the nucleic acid sequence of MSG HMSG11, GenBank Accession No: AF033208.

SEQ ID NO: 6 shows the amino acid sequence of MSG protein HuMSG11.

SEQ ID NO: 7 shows the nucleic acid sequence of MSG HMSG14, GenBank Accession No: AF033209.

SEQ ID NO: 8 shows the amino acid sequence of MSG protein HuMSG14.

SEQ ID NO: 9 shows the nucleic acid sequence of MSG HMSG32, GenBank Accession No: AF033212.

SEQ ID NO: 10 shows the amino acid sequence of MSG protein HuMSG32.

SEQ ID NO: 11 shows the nucleic acid sequence of MSG HMSG33, GenBank Accession No: AF033210.

SEQ ID NO: 12 shows the amino acid sequence of MSG protein HuMSG33.

SEQ ID NO: 13 shows the nucleic acid sequence of MSG HMSG35, GenBank Accession No: AF033211.

SEQ ID NO: 14 shows thc amino acid sequence of MSG protein HMSG35.

SEQ ID NO: 15 shows the nucleic acid sequence of the conserved carboxy-terminal portion of MSG HMSGp2, GenBank Accession Number: AF038556.

SEQ ID NO: 16 shows the amino acid sequence of the conserved carboxy-terminal portion of MSG protein HMSGp2.

SEQ ID NO: 17 shows oligonucleotide JKK14 (upstream primer).

SEQ ID NO: 18 shows oligonucleotide JKK15 (upstream primer).

SEQ ID NO: 19 shows oligonucleotide JKK16 (internal probe).

SEQ ID NO: 20 shows oligonucleotide JKK17 (downstream primer).

SEQ ID NO: 21 shows oligonucleotide JK151 (upstream cloning primer).

SEQ ID NO: 22 shows oligonucleotide JK152 (downstream cloning primer).

SEQ ID NO: 23 shows oligonucleotide JK451 (upstream C-terminal cloning primer).

SEQ ID NO: 24 shows oligonucleotide JK452 (downstream C-terminal cloning primer).

SEQ ID NO:25 shows the amino acid sequence of the internal peptide used to generate antibodies.

SEQ ID NO: 26 shows the amino acid sequence of the C-terminal peptide used to generate antibodies.

DETAILED DESCRIPTION OF THE INVENTION

1. Abbreviations and Definitions

A. Abbreviations

PCP: *Pneumocystis carinii* pneumonia (pneumocystosis)

MSG: major surface glycoprotein human-*P. carinii: P. carinii* sp. f hominis, human-derived *Pneumocystis carinii*

B. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

Biological Specimen: A biological specimen is a sample of bodily fluid or tissue used for laboratory testing or examination. As used herein, biological specimens include all clinical samples useful for detection of microbial infection in subjects.

Appropriate tissue samples may be taken from the oropharyngeal tract, for instance from lung or bronchial tissue. Samples can be taken by biopsy or during autopsy examination, as appropriate. Biological fluids include blood, derivatives and fractions of blood such as serum, and fluids of the oropharyngeal tract, such as sputum.

Examples of appropriate specimens for use with the current invention for the detection of *P. carinii* include conventional clinical samples, for instance blood or blood-fractions (e.g., serum), and bronchoalveolar lavage (BAL), sputum, and induced sputum samples. Techniques for acquisition of such samples are well known in the art. Blood and blood fractions (e.g., serum) can be prepared in traditional ways. Oropharyngeal tract fluids can be acquired through conventional techniques, including sputum induction, bronchoalveolar lavage (BAL), and oral washing. Oral washing provides an excellent, non-invasive technique for acquiring appropriate samples to be used in nucleic acid amplification (e.g., PCR) of human-*P. carinii* MSG sequences. Obtaining a sample from oral washing involves having the subject gargle with an amount normal saline for about 10–30 seconds and then expectorate the wash into a sample cup.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is synthesized in the laboratory by reverse transcription from messenger RNA extracted from cells.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Oligonucleotide: A linear polynucleotide sequence of between 10 and 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. *P. carinii* isolated from different host species (for instance rats and humans) are known to be distinct organisms, and may in fact be separate Pneumocystis species. Because of this, genes and proteins derived from *P. carinii* isolated from different host species are orthologous to each other (e.g., the MSG11 gene isolated from human-*P. carinii* (HMSG11) would be an ortholog of MSG11 isolated from rat-*P. carinii*). Orthologous sequences are also homologous sequences.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, Cold Spring Harbor, N.Y., 1989) and Ausubel et al. (In *Current Protocols in Molecular Biology*, Greene Publ. Assoc. and Wiley-Intersciences, 1992).

Primers are short nucleic acid molecules, preferably DNA oligonucleotides 15 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, Cold Spring Harbor, N.Y., 1989), Ausubel et al. (In *Current Protocols in Molecular Biology*, Greene Publ. Assoc. and Wiley-Intersciences, 1992), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of the human-*P. carinii* MSG11 gene will anneal to a target sequence, such as another MSG gene homolog from the gene family contained within a human-*P. carinii* genomic DNA library, with a higher specificity than a corresponding primer of only 15 nucleotides. Thus, in order to obtain greater specificity, probes and primers can be selected that comprise 20, 25, 30, 35, 40, 50 or more consecutive nucleotides of human-*P. carinii* MSG gene sequences.

The invention thus includes isolated nucleic acid molecules that comprise specified lengths of the disclosed human-*P. carinii* MSG gene sequences. Such molecules may comprise at least 20, 25, 30, 35, 40 or 50 consecutive nucleotides of these sequences, and may be obtained from any region of the disclosed sequences. By way of example, the human-*P. carinii* MSG gene sequences may be apportioned into halves or quarters based on sequence length, and the isolated nucleic acid molecules may be derived from the first or second halves of the molecules, or any of the four quarters. The human-*P. carinii* MSG11 gene, shown in SEQ ID NO: 3, can be used to illustrate this. The human-*P. carinii* MSG11 gene is 3088 nucleotides in length and so may be hypothetically divided into about halves (nucleotides 1–1544 and 1545–3088) or about quarters (nucleotides 1–772, 773–1544, 1545–237 and 2372–3088), for instance. Nucleic acid molecules may be selected that comprise at least 20, 25, 30, 35, 40 or 50 consecutive nucleotides of any of these portions of the human-*P. carinii* MSG11 gene. Thus, one such nucleic acid molecule might comprise at least 25 consecutive nucleotides of the region comprising nucleotides 2372–3088 of the disclosed human-*P. carinii* MSG11 gene (SEQ ID NO: 5).

Further nucleic acid molecules might comprise at least 15 consecutive nucleotides of the regions encoding the conserved carboxy-terminal portion of each human-*P. carinii* MSG gene. These regions comprise nucleotides 2794–3042 of HMSGp1 (SEQ ID NO: 1), 2758–3006 of HMSGp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), 2821–3072 of HMSG35 (SEQ ID NO: 13), and 1–249 of HMSGp2 (SEQ ID NO: 15), respectively.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity berween two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs of human-*P. carinii* MSG proteins, and the corresponding gene sequences, will possess a relatively high degree of sequence identity when aligned using standard methods. This homology will be more significant when the proteins or gene sequences are derived from *P. carinii* isolated from one host species (i.e., two human-*P. carinii* MSG homologs will typically have greater sequence identity than that shown by one human- and one rat-*P. carinii* MSG ortholog).

Typically, human-*P. carinii* MSG homologs are 74 to 91% identical at the nucleotide level and 63 to 88% identical at the amino acid level when comparing pairs of clones. In comparison, there is approximately 60% identity at the DNA level and 40% identity at the amino acid level when comparing a human *P. carinii* MSG to the rat *P. carinii* ortholog MSGGP3.

Methods of alignment of sequences for comparison are well known in the art. Various programs and alignment algorithms are described in: Smith & Waterman (1981) *Adv. Appl. Math.* 2:482; Needleman & Wunsch (1970) *J. Mol. Biol.* 48: 443; Pearson & Lipman (1988) *Proc. Natl. Acad. Sci. USA* 85: 2444; Higgins & Sharp (1988) *Gene*, 73: 237–244; Higgins & Sharp (1989) *CABIOS* 5:151–153; Corpet et al. (1988) *Nuc. Acids Res.* 16, 10881–90; Huang el al. (1992) *Computer Appls. in the Biosciences* 8, 155–65; and Pearson et al. (1994) *Meth. Mol. Bio.* 24, 307–31. Altschul et al. (1990) *J. Mol. Biol.* 215:403410, presents a detailed consideration of sequence alignment methods and homology calculations.

The NCBI Basic Local Alignment Search Tool (BLAST) (Altschul et al. (1990) *J. Mol. Biol.* 215:403410) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI online site under the "BLAST" heading. A description of how to determine sequence identity using this program is available at the NCBI online site under the "BLAST" heading and "BLAST overview" subheading. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties).

Other members of the gene family of the disclosed human-*P. carinii* MSG proteins typically possess at least 60% sequence identity counted over full-length alignment with the amino acid sequence of human-*P. carinii* MSG using the NCBI Blast 2.0, gapped blastp set to default parameters. Sequence identity over the about 100 C-terminal amino acids will typically be higher than 60%, for instances about 63%. Proteins with even greater similarity to the reference sequence will show increasing percentage identities when assessed by this method, such as at least 70%, at least 75%, at least 80%, at least 90%, at least 95%, or at least 98% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the NCBI online site under the "BLAST" heading and "Frequently Asked Questions" subheading.

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. ((1989) In *Molecular Cloning: A Laboratory Manual*, Cold Spring Harbor, N.Y.) and Tijssen ((1993) *Laboratory Techniques in Biochemistry and Molecular Biology—Hybridization with Nucleic Acid Probes* Part 1, Chapter 2, Elsevier, N.Y.). Nucleic acid molecules that hybridize under stringent conditions to a human-*P. carinii* MSG gene sequence will typically hybridize to a probe based on either an entire human-*P. carinii* MSG gene or selected portions of the gene under wash conditions of 2×SSC at 50° C. A more detailed discussion of hybridization conditions is presented below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus an MSG protein-specific binding agent binds substantially only the MSG protein. As used herein, the term "MSG protein specific binding agent" includes anti- MSG protein antibodies and other agents that bind substantially only to the MSG protein.

Anti-MSG protein antibodies may be produced using standard procedures described in a number of texts, including Harlow and Lane (*Antibodies, A Laboratory Manual*, CSHL, New York, 1988). The determination that a particular agent binds substantially only to the MSG protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given MSG protein binding agent, such as an anti-MSG protein monoclonal antibody, binds substantially only to the MSG protein.

Shorter fragments of antibodies can also serve as specific binding agents. For instance, FAbs, Fvs, and single-chain Fvs (SCFvs) that bind to MSG would be MSG-specific binding agents.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

II. Human-*P. Carinii* MSG Sequences

This specification provides MSG proteins and MSG-encoding nucleic acid molecules, including gene sequences, derived from human-*P. carinii*. The prototypical MSG sequences are the human-*P. carinii* sequences as presented herein (HMSGp1, HMSGp3, HMSG11, HMSG14, HMSG32, HMSG33, and HMSG 35).

a. Human-*P. carnii* HMSGp1, HMSGp3, HMSG11, HMSG14, HMSG32, HMSG33, and HMSG35

Human-*P. carinii* HMSGp1, HMSGp3, HMSG11, HMSG14, HMSG32, HMSG33, and HMSG35 genomic sequences are shown in SEQ ID NOS: 1, 3, 5, 7, 9, 11, and 13, respectively. The sequences typically encode proteins that are about 1000 to about 1030 amino acids in length (for instance, SEQ ID NO: 5 shows the amino acid sequence of the MSG11 protein, which is 1028 amino acids long). These human-*P. carinii* MSG proteins show significant sequence similarity to each other, and a lesser degree of sequence similarity to MSG proteins derived from organisms in other hosts.

With the provision herein of seven novel human-*P. carinii* MSG gene sequences, nucleotide amplification methods, for instance polymerase chain reaction (PCR), may now be utilized as a preferred method for producing nucleic acid sequences encoding these human-*P. carinii* MSG proteins.

For example, PCR amplification of the human-*P. carinii* MSG11 gene sequence may be accomplished by direct PCR from a clinical sample. Methods and conditions for direct PCR are known in the art and are described in Innis et al. (*PCR Protocols, A Guide to Methods and Applications*, Academic Press, Inc., San Diego, Calif., 1990). Appropriate sampling methods are described more fully below.

The selection of amplification primers will be made according to the portions of the gene that are to be amplified. Primers may be chosen to amplify small segments of the gene, the open reading frame, or the entire gene sequence. Variations in amplification conditions may be required to accommodate primers of differing lengths; such considerations are well known in the art and are discussed in Innis et al. (*PCR Protocols, A Guide to Methods and Applications*, Academic Press, Inc., San Diego, Calif., 1990), Sambrook et at (in *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992). By way of example only, the human-*P. carinii* HMSG11 gene as shown in SEQ ID NO: 5 can be amplified using the following combination of primers:

primer JK151: 5' TIT CAT ATG GCG CGG GCG GTC AAG CGG CAG 3' (SEQ ID NO: 21)

primer JK152: 5° CTA AAT CAT GAA CGA AAT AAC CAT TGC TAC 3' (SEQ ID NO: 22).

The sequence encoding the conserved carboxy-terminal region of human-*P. carinii* HMSG11 can be amplified using the following primer pair:

primer JKK14: 5' GAA TGC AAA TCC TTA CAG ACA ACA G 3' (SEQ ID NO: 17)

primer JKK17: 5' AAA TCA TGA ACG AAA TAA CCA TTG C 3' (SEQ ID NO: 20).

These primers are illustrative only; one skilled in the art will appreciate that many different primers may be derived from the provided MSG gene sequences in order to amplify particular regions of these molecules. Resequencing of PCR products obtained by these amplification procedures is recommended; this will facilitate confirmation of the amplified sequence and will also provide information on natural variation on this sequence in different ecotypes and plant populations. Oligonucleotides derived from the human-*P. carinii* MSG gene sequences provided may be used in such sequencing methods.

Further homologous human-*P. carinii* MSGs can be cloned in a similar manner. In order to increase the number of MSGs that can be amplified in a single PCR reaction, a third primer can be added. For instance, a second upstream primer (e.g., primer JKK15: 5' GAA TGC AAA TCT TTA CAG ACA ACA G 3' (SEQ ID NO: 18)) may be added to the amplification reaction along with primers JKK14 and JKK17. Typically, when more than two primers are provided in a single PCR amplification reaction, those primers that anneal to the same site on the target nucleotide sequence (e.g., JKK14 and JKK15) will be provided in equimolar amounts (for instance, 0.625 pM each), and such that the total amount of primer provided for each end of the amplicon will be equivalent (for instance, 1.25 pM each).

Oligonucleotide that are derived from the human-*P. carinii* HMSGp1, HMSGp3, HMSG11, HMSG14, HMSG32, HMSG33, and HMSG35 gene sequences (SEQ ID NOS: 1, 3, 5, 7, 9, 11, and 13, respectively), as well as the fragment of HMSGp2 disclosed (SEQ ID NO: 15), are encompassed within the scope of the present invention. Preferably, such oligonucleotide primers will comprise a sequence of at least 15–20 consecutive nucleotides of the relevant human-*P. carinii* MSG gene sequence. To enhance amplification specificity, oligonucleotide primers comprising at least 25, 30, 35, 40, 45 or 50 consecutive nucleotides of these sequences may also be used. These primers for instance may be obtained from any region of the disclosed sequences. By way of example, human-*P. carinii* MSG gene sequences may be apportioned into halves or quarters based on sequence length, and the isolated nucleic acid molecules may be derived from the first or second halves of the molecules, or any of the four quarters. In addition, primers may be specifically chosen from the conserved carboxy-terminal region of each MSG coding sequence. This region comprises nucleic acid residues 2794–3042 of HMSGp1 (SEQ ID NO: 1), 2758–3006 of HMSGp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), 2821–3072 of HMSG35 (SEQ ID NO: 13), and 1–249 of HMSGp2 (SEQ ID NO: 15).

With the provision of human-*P. carinii* HMSGp1, HMSGp3, HMSG11, HMSG14, HMSG32, HMSG33, and HMSG35 proteins and corresponding gene sequences herein, the creation of variants of these sequences is now enabled.

Variant MSG proteins include proteins that differ in amino acid sequence from the human-*P. carinii* MSG sequences disclosed but that share at least 63% amino acid sequence homology (for example at least 80%, 90%, 95% or 98% homology) with any of the provided human MSG proteins. Such variants may be produced by manipulating the nucleotide sequence of the, for instance, human-*P. carinii* HMSG11 gene using standard procedures, including for instance site-directed mutagenesis or PCR. The simplest modifications involve the substitution of one or more amino acids for amino acids having similar biochemical properties. These so-called conservative substitutions are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in enzymatic function or other protein features may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant MSG genes may be produced by standard DNA mutagenesis techniques, for example, M13 primer mutagenesis. Details of these techniques are provided in Sambrook el al. (In *Molecular Cloning: A Laboratory Manual*, Cold Spring Harbor, N.Y., 1989), Ch. 15. By the use of such techniques, variants may be created which differ in minor ways from the human-*P. carinii* MSG gene sequences disclosed. DNA molecules and nucleotide sequences which are derivatives of those specifically disclosed herein and that differ from those disclosed by the deletion, addition, or substitution of nucleotides while still encoding a protein that has at least 63% sequence identity with the MSG sequences disclosed (SEQ ID NOS: 1, 3, 5, 7, 9, 11, and 13) are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed human *P. carinii* MSG protein sequences. For example, the 2nd amino acid residue of the human *P. carinii* HMSG11 protein is alanine. The nucleotide codon triplet GCG encodes this alanine residue. Because of the degeneracy of the genetic code, three other nucleotide codon triplets—GCT, GCC and GCA—also code for alanine. Thus, the nucleotide sequence of the human *P. carinii* HMSG11 ORF could be changed at this position to any of these three alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode an MSG protein, but which vary from the disclosed nucleic acid sequences by virtue of the degeneracy of the genetic code.

Variants of the MSG protein may also be defined in terms of their sequence identity with the prototype MSG proteins shown in SEQ ID NOS: 2, 4, 6, 8, 10, 12, and 14. As described above, human MSG proteins share at least 60% (for example, at least 63%) amino acid sequence identity with the human *P. carinii* HMSGp1, HMSGp3, HMSG11, HMSG14, HMSG32, HMSG33, or HMSG35 proteins (SEQ ID NOS: 2, 4, 6, 8, 10, 12, and 14, respectively). Nucleic acid sequences that encode such proteins may readily be determined simply by applying the genetic code to the amino acid sequence of an MSG protein, and such nucleic acid molecules may readily be produced by assembling oligonucleotides corresponding to portions of the sequence.

Nucleic acid molecules that are derived from the human *P. carinii* MSG gene sequences disclosed include molecules that hybridize under stringent conditions to the disclosed prototypical MSG nucleic acid molecules, or fragments thereof. Stringent conditions are hybridization at 65° C. in 6×SSC, 5×Denhardt's solution, 0.5% SDS and 100 $\mu$g sheared salmon testes DNA, followed by 15–30 minute sequential washes at 65° C. in 2×SSC, 0.5% SDS, followed by 1×SSC, 0.5% SDS and finally 0.2×SSC, 0.5% SDS.

Low stringency hybridization conditions (to detect less closely related homologs) are performed as described above but at 50° C. (both hybridization and wash conditions); however, depending on the strength of the detected signal, the wash steps may be terminated after the first 2×SSC wash.

Human-*P. carinii* HMSGp1, HMSGp3, HMSG11, HMSG14, HMSG32, HMSG33, and HMSG35 genes (SEQ ID NOS: 1, 3, 5, 7, 9, 11 and 13), as well as the fragment of HMSGp2 disclosed (SEQ ID NO: 15), and homologs of these sequences may be incorporated into transformation or expression vectors.

III. Detection of *P. Carinii* In Clinical Specimens

The conserved nature of human-*P. carinii* MSG genes provided in this specification, and particularly the highly-conserved about 100 amino acid region in the C-terminal portion of the protein, makes these genes useful targets for use in detection of *P. carinii* in clinical samples and diagnosis of PCP.

a. Clinical Specimens

Appropriate specimens for use with the current invention in detection of *P. carinii* include any conventional clinical samples, for instance blood or blood-fractions (e.g., serum), and bronchoalveolar lavage (BAL), sputum, and induced sputum samples. Techniques for acquisition of such samples are well known in the art. See, for instance, Schluger et al. (*J. Exp. Med* 176:1327–1333) (collection of serum samples); Bigby et al. (*Am. Rev. Respir. Dis.* 133:515–518, 1986) and Kovacs et al. (*NEJM* 318:589–593, 1988) (collection of sputum samples); and Ognibene et al. (*Am. Rev. Respir. Dis.* 129:929–932,1984) (collection of bronchoalveolar lavage (BAL).

In addition to conventional methods, oral washing provide an excellent, non-invasive technique for acquiring appropriate samples to be used in nucleic acid amplification (e.g. PCR) of human-*P. carinii* MSG sequences (Helweg-Larsen et al. (1998) *J. Clin. Microbiol.* 36:2068–2072). Oral washing involves having the subject gargle with 50 cc of normal saline for 10–30 seconds and then expectorate the wash into a sample cup.

Serum or other blood fractions can be prepared in the conventional manner. About 200 $\mu$L of serum is an appropriate amount for the extraction of DNA for use in amplification reactions. See also, Schluger et al., (1992) *J. Exp. Med.* 176:1327–1333; Ortona et al., (1996) *Mol. Cell Probes* 10:187–90.

Once a sample has been obtained, DNA can be extracted through any conventional method. For instance, rapid DNA preparation can be performed using a commercially available kit (e.g., the InstaGene Matrix, BioRad, Hercules, Calif.; the NucliSens isolation kit, Organon Teknika, Netherlands). Preferably the DNA preparation technique chosen yields a nucleotide preparation that is accessible to and amenable to nucleic acid amplification.

b. Direct Hybridization Probing Detection

Human-*P. carinii* MSG gene sequences can be detected through the hybridization of an oligonucleotide probe to nucleic acid molecules prepared from a clinical sample. The sequence of appropriate oligonucleotide probes will correspond to a region within one or more of the human-*P. carinii* MSG sequences disclosed herein. Techniques for use in hybridization of oligonucleotide probes to target sequences will be known to one of ordinary skill in the art. See, for instance, U.S. Pat. Nos. 5,164,490 (disclosing use of sequences from the *P. carinii* dihydrofolate reductase gene as direct hybridization probes) and 5,519,127 (using nucleic acid probes capable of hybridizing to rRNA or rDNA of *P. carinii* for detection of the organism). In general, hybridization probes will be at least 15 bases in length, and may be 20, 25, 30, 35, 40 or 50 or more bases in length. For instance, a probe may comprise the entire conserved sequence of an MSG (e.g., residues 2845–3090 of HMSG11), or the entire coding sequence of the gene. Typically such a probe will be detectably labeled in some fashion, either with an isotopic or non-isotopic label. Such non-isotopic labels may, for instance, comprise a fluorescent or luminescent molecule, or an enzyme, co-factor, enzyme substrate, or hapten. The probe is generally incubated with a single-stranded preparation of DNA, RNA, or a mixture of both, and hybridization determined after separation of double and single-stranded molecules. Alternatively, probes may be incubated with a nucleotide preparation after it has been separated by size and/or charge and immobilized on an appropriate medium. Hybridization techniques suitable for use with oligonucleotides are well known to those of ordinary skill in the art. For general references on the conditions and options that are appropriate, see Sambrook et al. (1989) *Molecular Cloning: A Laboratory Manual*, Cold Spring Harbor, N.Y., and Ausubel et al. (1992) In *Current Protocols in Molecular Biology*, Greene Publishing Associates and Wiley-Intersciences.

c. Nucleic Acid-Mediated Detection

It may be advantageous to amplify target *P. carinii* gene sequences in a clinical sample prior to using a hybridization probe to detect its presence. For instance, for detection of human-*P. carinii* MSG gene sequences, it may be advantageous to amplify part or all of the MSG gene sequence, then detect the presence of the amplified sequence pool. Any nucleic acid amplification method can be used, including polymerase chain reaction (PCR) amplification. Amplification can be carried out in a simple single reaction using a pair of primers, or can be enhanced by the use of multiple degenerate primers to increase the number of MSG homologs that are amplified. Where degenerate primers are used, the sequence variability of the disclosed human-*P. carinii* MSG gene sequences can be used to design appropriate primers that will be specific for multiple human *P. carinii* MSG homologs. Alternately, amplification specificity can be increased through the use of nested PCR techniques, which are known (see, for instance, Lipschik et al. (1992) *Lancet* 340:203–206, using nested sets of primers to rRNA in the detection of *Pneumocystis carinii*).

It is also possible to run sequential PCR amplification experiments on samples using different targets in each reaction, such that putative positive samples detected in the first reaction are confirmed by amplification of a second sequence. For instance, it would be possible to analyze clinical samples through PCR amplification of a human-*P. carinii* MSG gene, then to take only those samples that are positive for amplification of MSG and test them also for the presence of *P. carinii* rRNA, for instance. Such sequential testing of samples will help reduce false positive results due to cross contamination of PCR samples; it is unlikely that a clinical sample will become contaminated with both target sequences.

The selection of PCR primers will be made according to the portions of the gene sequence that are to be amplified. For use in PCR detection of *P. carinii*, it is advantageous to choose primer-annealing sites that are highly conserved across many different members of the human-*P. carinii* MSG gene family. For instance, it is advantageous to choose primer sites from within the regions of human-*P. carinii* sequence displaying greater than 63% sequence identity across the disclosed family members, e.g., that portion of the gene encoding the conserved carboxy-terminal region of the protein. The highly conserved carboxy-terminal regions of the disclosed genes are as follows: residues 2794–3042 of HMSGp1 (SEQ ID NO: 1), 2758–3006 of HMSGp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), 2821–3072 of HMSG35 (SEQ ID NO: 13), and 1–249 of HMSGp2 (SEQ ID NO: 15).

Variations in amplification conditions may be required to accommodate primers of differing lengths; such considerations are well known in the art and are discussed in Sambrook et al. ((1989) In *Molecular Cloning: A Laboratory Manual*, Cold Spring Harbor, N.Y.) and Ausubel et al. (In *Current Protocols in Molecular Biology*, Greene Publishing Associates and Wiley-Intersciences, 1992). By way of example only, primers JKH14, JKH15, and JKK17 (SEQ ID NOS: 17,18, and 20 respectively) can be used to amplify the C-terminal conserved region of several human-*P. carinii* MSG genes. These primers are illustrative only; one skilled in the art will appreciate that many different primers may be derived from the provided cDNA and gene sequences in order to amplify particular regions of these molecules.

Oligonucleotides to be used in detection of the *P. carinii* organism or diagnosis of PCP that are derived from the human-*P. carinii* MSG gene sequences disclosed herein are encompassed within the scope of the present invention.

d. Detection of Amplified *P. carinii* MSG Sequences

The presence of amplified human-*P. carinii* MSG sequences can be determined in any conventional manner, including electrophoresis and staining (for instance, with ethidium bromide) of the amplified sequence, or hybridization of a labeled probe to the amplified sequence. For general guidelines on such techniques, see *Molecular Cloning: A Laboratory Manual*, Cold Spring Harbor, N.Y. (1989), and *Current Protocols in Molecular Biology*, Greene Publishing Associates and Wiley-Intersciences (1987). Hybridization probes appropriate for use in detection of amplified human-*P. carinii* MSG sequences are essentially equivalent to those described above for direct hybridization. The region of the gene that has been amplified will be important in choosing an appropriate probe; the detection probe should hybridize to a sequence that falls between the ends of the amplification primers such that the annealing site of the probe is amplified. By way of example, one appropriate oligonucleotide probe is JKK16 (SEQ ID NO: 19), which corresponds to residues of 2926–2950 of HMSG33. This probe could be used for detection of both full-length and carboxy-terminal amplified fragments of human-*P. carinii* MSG genes.

Typically, oligonucleotide probes will be labeled as discussed above, and detection will be carried out through conventional methods. In general, detection of amplified sequences will be more sensitive than direct hybridization.

In addition to radioisotope labeled hybridizing probes, amplicons can be detected using fluorescent labeled probes. One such appropriate fluorescent label is europium ($Eu^{3+}$).

See, for instance, Lopez et al. (1993) *Clin. Chem.* 39(2): 196–201 (using a europium derivative for time-resolved fluorescence detection of amplified human papillomavirus sequences); Eskola et al. (1994) *Clin. Biochem.* 27(5) :373–379 (using PCR and europium-labeled DNA probes to detect a marker for chronic myelogenous leukemia); and Dahlen et al. (1991) *J. Clin. Microbiol.* 29(4):798–804 (detection of PCR amplified HIV sequences using biotinylated and europium labeled oligonucleotide probes).

e. Preparation of a Positive Nucleic Acid Amplification Control

It is advantageous to provide a positive control sequence for use in nucleic acid amplification reactions, to ensure that the system is functioning properly. The positive control sequence should be one the provided oligonucleotide primers are known to anneal to. Therefore, in the present invention, appropriate positive control sequences include, for instance, any sequences that can be amplified with the same primers as are used to amplify human-*P. carinii* MSG. For instance, primers JKK14 (SEQ ID NO: 17) and JKK17 (SEQ ID NO: 20) can serve as appropriate primers. It is advantageous, however, if the internal amplified sequence is distinguishable from the MSG target (i.e., is a mimic rather than identical sequence); this allows specific and separate detection of the target and mimic amplified products. Appropriate differences between the two sequences include overall length of the amplicon (where detection of the PCR products will be performed using electrophoresis and subsequent staining) and amplicon sequence differences (where detection of the PCR products will be performed using hybridization to a labeled probe specific for each amplified sequence).

Nucleic acid amplification positive control sequences can be provided in the form of independent, linear nucleotide sequences. Alternately, a recombinant vector comprising the appropriate positive control sequence may be provided. Construction of such a recombinant vector is by conventional means, and any of a myriad of conventional cloning vectors can be used. In general, the vector will include one or more restriction enzyme sites into which the PCR control sequence can be inserted. The vector may also comprise a replication site to provide for its production in a suitable host cell, for instance in a bacterial cell. The choice of appropriate cloning vector will be within the skill of an ordinary artisan.

IV. Kits For Detection of *P. Carinii*

The oligonucleotide primers disclosed herein can be supplied in the form of a kit for use in detection of *P. carinii* or diagnosis of PCP. in such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of human-*P. carinii* can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

A kit may include more than two primers, in order to facilitate the PCR amplification of a larger number of human-*P. carinii* MSG genes. For instance, primers JKK14 (SEQ ID NO: 17) and JKK15 (SEQ ID NO: 18) both may be provided as upstream primers, while primer IKK17 (SEQ ID NO: 20) is provided as a downstream primer. These primers are provided by way of example only.

In some embodiments of the current invention, kits may also include the reagents necessary to carry out PCR amplification reactions, including, for instance, DNA sample preparation reagents, appropriate buffers (e.g., polymerase buffer), salts (e.g. magnesium chloride), and deoxyribonucleotides (dNTPs).

Kits may in addition include either labeled or unlabeled oligonucleotide probes for use in detection of the amplified human-*P. carinii* sequences. The appropriate sequences for such a probe will be any sequence that falls between the annealing sites of the two provided oligonucleotide primers, such that the sequence the probe is complementary to is amplified during the PCR reaction. Primer JKK16 (SEQ ID NO: 19) exemplifies such a sequence, and an appropriate probe could comprise this sequence.

It may also be advantageous to provided in the kit one or more control sequences for use in the PCR reactions. Appropriate positive control sequences may be essentially as those discussed above.

EXAMPLES

Example 1

Isolation of Multiple Human-*P. carinii* MSG Sequences

A. Polymerase Chain Reaction (PCR) Amplification Cloning

DNA was isolated from an autopsy lung sample of an HIV-infected patient with *P. carinii* pneumonia according to standard methods, using SDS and proteinase K (0.5 μg/ml), followed by phenol-chloroform extraction and ethanol precipitation (Davis et al. (1986) *Basic Methods in Molecular Biology*, Elsevier, N.Y.). A genomic library using the same DNA cloned into the Xho1 site of lambda GEM 12 vector (Promega, Madison, Wis.) was commercially prepared (Lofstrand Labs Limited, Gaithersburg, Md.).

Primers to amplify full-length human *P. carinii* genes were designed based on published data (Garbe and Stringer (1994) *Infect. Immun.* 62(8):3092–3101). The sense primer, JK151 (5'-TTT CAT ATG GCG CGG GCG GTC AAG CGG CAG-3') (SEQ ID NO: 21) corresponds to nucleotides 153 to 175 of a published MSG sequence (GenBank accession number L27092), and the antisense primer JK152 (5'-CTA AAT CAT GAA CGA AAT AAC CAT TGC TAC-3') (SEQ ID NO: 22) is complementary to nucleotides 3215 to 3244 of the same sequence. An NdeI site was created at the beginning of JK151, which substitutes a methionine for the valine of the original sequence, to facilitate subcloning and expression. For amplification, 1 μg of genomic DNA was added to a 50 μl reaction containing primers (25 pM each), dNTPs (0.2 mM), 5 U of AmpliTaq (Perkin-Elmer), and $MgCl_2$ (2.5 mM). The DNA amplification was performed on a Perkin Elmer Cetus DNA thermal cycler. An initial denaturation cycle (1 minute at 96° C.) was followed by 36 cycles of denaturation at 95° C. for 1 minute, annealing at 50° C. for 2 minutes and extension at 72° C. for 2 minutes, followed by a final extension after the last cycle at 72° C. for 10 minutes.

A band of the correct size (approximately 3.1 Kb) was amplified and subjected to electrophoresis in 1% agarose gel in 1×TBE buffer. PCR products were then directly subcloned into PCR II (Invitrogen, Carlsbad, Calif.) according to the manufacturer's instructions. Five clones that differed in their restriction mapping and hybridization patterns were identified and sequenced (HMSG11 (SEQ ID NO: 5) GenBank accession number AF033208; HMSG14 (SEQ ID NO: 7) number AF033209; HMSG33 (SEQ ID NO: 11) number AF033210; HMSG35 (SEQ ID NO: 13) number AF033211; and HMSG32 (SEQ ID NO: 9) number AF033212).

Nucleotide sequencing was performed using an automated sequencer (Model 373 or 377. Applied Biosystems/ Perkin Elmer, Foster City, Calif.). The nucleotide sequence and deduced amino acid sequence data were analyzed by Factura and AutoAssembler (both from Applied Biosystems), Sequencher (Gene Codes Corp., Ann Arbor, Mich.), MacVector (Scientific Imaging Systems, New Haven, Conn.), ClustalW (40), and GeneWorks (IntelliGenetics, Mountain View, Calif.).

All clones encoded MSG variants that were clearly related but differed from each other. The coding region of the clones varied in length from 3,054 to 3,087 bases, encoding proteins of 1,008 to 1,028 amino acids with predicted molecular weights of 114 to 117 KDa. They are 74 to 91% identical at the nucleotide level and 63 to 88% identical at the amino acid level when comparing pairs of clones. Overall, approximately 50% of the amino acids are conserved in all five clones. The clones are more closely related to each other than to rat *P. carinii* MSG genes. There is an approximately 60% identity at the DNA level and 40% identity at the amino acid level when comparing a human *P. carinii* MSG to rat *P. carinii* MSGGP3.

B. Southern Hybridization/Library Screening

For southern hybridization with a radioactive probe, DNA was treated with restriction enzymes, separated by agarose gel electrophoresis and transferred to Hybond N+ membranes (Amersham, Life Science, Arlington Heights, Ill.) with 0.4 M NaOH. DNA was probed using an approximately 600 bp XbaI fragment of the human *P. carinii* MSG III gene (Garbe and Stringer (1994) *Infect. immuno.* 62:3092–3101) that had been labeled with α-32P dATP or α-32P dCTP by a random priming kit (Boehringer Mannheim). Filters were prehybridized for 4 hours and then hybridized overnight at 55° C. in 6×SSPE with 0.5% SDS, and 5×Denhardt's solution. Blots were washed in 6×SSPE with 0.5% SDS at room temperature for 10 minutes and then in 0.5×SSPE with 0.5% SDS at 55° C. twice for 30 minutes each. The genomic library was screened using a gel-purified fiill-length fragment of HMSG11 under the same conditions as above. One clone that hybridized strongly to the probe was subcloned into the BamHI site of pBluescript 11 (Stratagene, La Jolla, Calif.). This 12,792 bp clone (GenBank accession number AF038556) contained three full-length and one partial MSG sequences in a head to tail tandem arrangement, similar to what has previously been reported (Garbe and Stringer (1994) *Infect. Immun.* 62:3092–3 101; Stringer et al. (1993) *J. Eukaryot. Microbiol.* 40:821–826). One of the full-length MSG sequences did not have a complete open reading frame due to a frame shift between bases 6290 and 6347. The codon corresponding to a methionine at the beginning of rat *P. carinii* MSG clones encoded a valine in all the open reading frames, consistent with earlier observations (Garbe and Stringer (1994) *Infect. Immun.* 62:3092–3101; Stringer et al. (1993) *J. Eukaryot. Microbiol.* 40:821–826). Nucleotide sequencing was performed as above.

Example 2

Characterization of Human-*P. carinii* MSG Proteins

FIG. 1 shows an alignment of the predicted proteins encoded by the full length MSG genes cloned by PCR (MSG 11, 14, 32, 33, and 35) and Southern (MSGp1 and p3), together with previously published a human (Garbe and Stringer (1994) *Infect. Immun.* 62:3092–3101) and rat *P. carinii* MSG sequence (GenBank accession number L05906). Among the human-*P. carinii* MSG sequences, there is substantial variability downstream of the amino-terminus, while the region near the carboxyl terminus is highly conserved. For example, there is 63% identity in the last 100 amino acids among all the genes (excluding the region encoded by the PCR primer JK152), which is about five times as high as the conservation among the first 100 amino acids (13% excluding the primer region corresponding to primer JK151). Like most known genes of *P. carinii*, all human *P. carinii* MSG genes show a strong AT bias, especially in the third position (approximately 70% A or T) (Edman et al. (1989) *Proc. Natl. Acad Sci. USA.* 86:8625–8629; Garbe and Stringer (1994) *Infect. Immun.* 62:3092–3101; Kovacs et al. (1993) *J. Biol. Chem.* 268:6034–6040; Wada et al. (1993) *J. Infect. Dis.* 168:979–985). As in other MSG molecules, cysteine residues of the human *P. carinii* MSG molecules are relatively numerous (5.7 to 5.9%) and are highly conserved: 96% of all the cysteine residues present in the human-*P. carinii* MSG clones are conserved in all the clones. When comparing HuMSG11 to rat *P. carinii* MSG clone GP3, 94% of cysteine residues are conserved. The cysteine residues are unevenly distributed in four main regions and often show a pattern of two cysteines separated by 6 to 7 amino acids, similar to what is seen in rat *P. carinii* (Kovacs et al. (1993) *J. Biol. Chem.* 268:6034–6040). There is no predictable pattern to the intervening amino acids. All human MSG proteins share a highly conserved amino acid domain rich in threonine and serine residues near the carboxyl terminus. Seven to thirteen potential N-linked glycosylation sites (NXS/T) were observed in the MSGs. A premature stop codon was seen in MSG 32 after residue 1008 which is most probably due to a PCR artifact resulting in a point mutation; studies using the ligase chain reaction with primers specific for the mutation supported this conclusion.

A. Construction and Expression of Full Length Recombinant Human *P. carinii* MSG The full-length HMSG32 gene, which contains the premature stop codon, was inserted into pBlueBacHis2A (Invitrogen, Carlsbad, Calif.) at the EcoR1 site for expression in a baculovirus insect cell system. Correct insertion was confirmed by restriction mapping and sequencing. Isolation of recombinant virus, plaque purification and amplification of high titer virus stock were performed according to the manufacturer's protocols (Invitrogen, Carlsbad, Calif.). PCR amplification using gene-specific primers was used to confirm the presence of the gene in the virus. Sf9 cells were grown at 27° C. in SFII-900 medium (GIBCO BRL Grand Island, N.Y.) with 5% fetal calf serum to a density of $2.0\times10^6$ cells/ml. Cells were infected at a multiplicity of infection (moi) of 5. Seventy-two hours after infection, cells were harvested by centrifugation, washed with phosphate buffered saline supplemented with PMSF (1 mM/ml), then resuspended in 10 mM Tris-HCl, pH 8 with 1 mM PMSF, and sonicated. The cell lysates were analyzed by SDS-PAGE and western blotting.

SDS-PAGE and western blotting were performed using standard techniques (see Kovacs et al. (1988) *J. Immunol.* 140:2023–2031). Electrophoresis was done in pre-poured discontinuous 8% and 14% acrylamide tris-glycine gels (Novex, San Diego, Calif.). Proteins were stained by Coomassie blue or transferred to nitrocellulose membranes, following which western blots were performed with a variety of antisera using standard techniques (Kovacs et al. (1988) *J. Immunol.* 140:2023–2031). Recombinant rat *P. carinii* HMSGp3 protein (expressed in a baculovirus system) (Mei et al. (1996) *J. Eukarot. Microbiol.* 43:31S) and purified recombinant 5-galactosidase (expressed in the pET 28-E. coli system) were used as controls in western blotting.

Anti-peptide antisera were commercially generated in rabbits to a peptide specific for HMSG32 (KMYGLFYGSGKEWFKKLLEKIM (SEQ ID NO: 25), corresponding to amino acids 461482) and to a conserved human-*P. carinii* MSG epitope contained within the recombinant carboxyl terminal fragment (TITSTITSKITLTST (SEQ ID NO:26) corresponding to amino acids 968 to 982 of MSG32) by the multiple antigenic peptide system method (Posnett et al. (1988) *J. Biol. Chem.* 263:1719–1725) (Research Genetics, Huntsville, Ala.). Anti-Xpress monoclonal antibody, which detects an epitope tag at the amino terminus of the fusion proteins expressed in pBlueBacHis2A, was purchased from Invitrogen (Carlsbad, Calif.). T7-tag monoclonal antibody, which detects an epitope tag at the amino terminus of the fusion proteins derived from PET 28A, was purchased from Novagen, Inc. (Madison, Wis.).

A time course showed that maximal expression occurred after 60–72 hours of infection. The identity of the recombinant protein was confirmed by western blotting using both an antibody against a peptide tag present in the vector as well as an anti-peptide antibody raised against a peptide (SEQ ID NO: 25) specific for MSG32. No reactivity was seen when SF9 cells alone or recombinant baculovirus-derived rat MSG GP3 were used as the targets. Multiple bands were seen in the western blots, especially when using the MSG-specific anti-peptide antibody. These likely represent protein degradation products, or possibly modification of the recombinant protein.

Although rat MSGGP3 could be produced at a high level in a baculovirus system, and was easily purified by affinity chromatograph using a nickel column (Mei et al. (1996) *J. Eukarot. Microbiol.* 43:31S), prolonged attempts to produce and purify high levels of human *P. carinii* MSG were unsuccessful.

B. Construction and Expression of the Conserved C-terminal Portion of Human-*P. carinii* MSGs PCR was used to amplify the conserved carboxy-terminal region of the human *P. carinii* MSG gene without the carboxyl terminus hydrophobic tail, since this hydrophobic tail could potentially interfere with expression and purification. Primers were designed based on the alignment of five new MSG genes as well as the published sequence. The sense primer was JK451 (5'-GAA TTC GAT CTG AAG CCT CTG GAG-3') (SEQ ID NO: 23), and the antisense primer was JK452 (5'-TTC TAG AAA CCC ACT CAT CTT CAA-3') (SEQ ID NO: 24). An EcoR1 site was added to the sense primer and an XbaI site, which encoded an in frame stop codon, was added to the antisense primer to facilitate subcloning. One pg of plasmid DNA was used for PCR amplification under the same conditions used above for isolation of PCR clones.

The 306 bp PCR product of carboxy-terminal region amplified from MSG33 was ligated in frame into pET28A (Novagen, Inc. Madison, Wis.) at the EcoR1 site. pET28A is an expression vector in which a histidine tag precedes the insertion site. The presence of a six histidine (hexa-his) sequence in the expressed portion of the vector preceding the insert allows rapid, one-step purification of the recombinant protein by binding to nickel metal affinity chromatography matrix. Restriction mapping and sequencing were performed to confirm correct insertion. Expression was induced in *E. coli* strain BL21 (DE3) using 1 mM IPTG. Recombinant protein was solubilized with 6M urea and purified by affinity chromatography using a nickel column according to the manufacturer's instructions (Novagen, Inc., Madison, Wis.). The sample was eluted with elution buffer without urea, dialyzed using 0.5×PBS to eliminate imidazole, and lyophilized for storage.

Recombinant protein was analyzed by SDS-PAGE and western blotting as above. High level expression was observed within two hours; no equivalent band was seen using pET 28A without insert under the same conditions. Although the yield was variable from experiment to experiment, typically about 7 milligrams of purified protein was obtained from a one liter culture of *E. coli*. The identity of the protein was confirmed by immunoblotting using both T7-tag monoclonal antibody and a polyclonal anti-epitope antibody generated in rabbits against an epitope (SEQ ID NO: 26) contained within the recombinant carboxyl terminal fragment. No reactivity was seen with preimmune rabbit serum, with uninduced *E. coli* extracts, or with second antibody alone.

C. Evaluation of Human Sera Using Antibodies to Human-*P. carinii* MSG

Human sera evaluated by immunoblotting included sera from both AIDS and non-AIDS patients with and without a history of *P. carinii* pneumonia, as well as healthy individuals. Samples included those from 11 immunosuppressed patients with recent or acute *P. carinii* pneumonia but without HIV infection, 5 patients with HIV infection and *P. carinii* pneumonia, 17 patients with HIV infection but without *P. carinii* pneumonia, 3 patients with neither HIV infection nor *P. carinii* pneumonia, and 13 healthy laboratory workers. Human sera were tested at a dilution of 1:100. Horseradish peroxidase-conjugated goat anti-human IgG, alkaline phosphatase conjugated goat anti-rabbit IgG and goat anti-mouse IgG (all from GIBCO BRL) or horseradish peroxidase conjugated goat anti-cat, anti-rat, and anti-mouse IgG (Jackson ImmunoResearch Laboratories, Inc., West Grove, Pa.) were used as second antibodies in western blotting.

All 49 samples reacted by immunoblotting with the recombinant peptide. Because the recombinant peptide included a vector-derived region, a subset of 4 samples was simultaneous evaluated for reactivity with recombinant β-galactosidase expressed in the same vector. None of the samples reacted with the recombinant β-galactosidase, demonstrating that the reactivity seen was against the *P. carinii* derived peptide region. In addition, little or no reactivity was seen when using rat, mouse, or cat serum.

Example 3

Detection of Human-*P. carinii* Nucleic Acid Sequences

A. Preparation of a Vector Comprising A Control Sequence

A mimic amplification construct containing a positive control sequence was prepared using the tetracycline resistance ($tet^R$) gene coding sequence from pBR322 (Backman and Boyer (1983) *Gene* 26:197). In order to generate a $tet^R$ gene-based amplicon that could be amplified using MSG-specific primers JKK14/15 and JKK17, bipartite primers were generated with two distinct annealing regions. The 5' region of each primer was taken from the MSG target sequences (e.g., SEQ ID NOS: 17 and 20). The 3' region of each primer was designed to be specific to the tetR coding sequence. Amplification using these primers generated an amplicon containing an approximately 280 base internal fragment of tetr coding sequence, with 25 nucleotide MSG-specific ends. For amplification, 1 μg of $tet^R$ coding sequence DNA was added to a 50 μl reaction containing primers (25 pM each), dNTPs (0.2 mM), 5 U of AmpliTaq (Perkin-Elmer), and $MgCl_2$ (2.5 mM). The DNA amplification was performed on a Perkin Elmer Cetus DNA thermal cycler. An initial denaturation cycle (2 minutes at 94° C.) was followed by 34 cycles of denaturation at 94° C. for 1 minute, annealing at 68° C. for 1 minute and extension at 72° C. for 2 minutes, followed by a final extension after the last cycle at 72° C. for 5 minutes.

The resultant 294 base pair amplicon was ligated in to the pCR 2.1 vector and transformed into *E. coli* following the manufacturer's procedures (TA cloning Kit, Invitrogen, Carlsbad, Calif.). Confirmation of the insert was performed through standard cloning and PCR techniques.

B. Collection and Preparation of Clinical Samples

Clinical samples for use in MSG-PCR detection of *P. carinii* can be collected in any conventional way. Sputum was collected as described in Bigby et al. (*Am. Rev. Respir. Dis*. 133:515–518, 1986), and Kovacs et al. (*NEJM* 318:589–593, 1988). Bronchoalveolar lavage (BAL) was performed as described in Ognibene et al. (*Am. Rev. Respir. Dis*. 129:929–932,1984). Oral washes were carried out by having the subject gargle with 50 cc of normal saline for 10–30 seconds and then expectorate the wash into a sample cup (Helweg-Larsen et al. (1998) *J. Clin. Microbiol*. 36:2068–2072). Serum samples were obtained from blood in a conventional fashion. A 200 μL aliquot of serum was used for DNA extraction.

Oral washes, sputum and bronchoalveolar lavages were spun down 3500 rpm for 10 minutes and the supernatant decanted, leaving approximately 1 ml of liquid in which to resuspend the pellet. Samples were transferred to 2 ml microfuge tubes and centrifuge at 10,000 rpm for 10 minutes to remove remaining liquid. A 250 μL aliquot of InstaGene Matrix (BioRad. Cat. #732-6030, Hercules, Calif.) was added to the pellet and vortexed briefly. The samples were then incubated at 56° C. for 20 minutes, vortexed for 10 seconds and incubated at 100° C. for 8 minutes. The samples are vortexed again for 10 seconds and centrifuged at 12,000 rpm for 3 minutes; 5 pL of the resultant supernatant was used in each standard 50 μL PCR reaction.

In certain experiments, DNA was extracted from samples prepared as above using the NucliSens Isolation System (Organon Teknika Corp., Netherlands), using the manufacturer's instructions.

C. Conditions for PCR Reactions

To minimize contamination, DNA extraction, amplification and product detection procedures were carried out in separate areas of the laboratory, aerosol-barrier pipette tips were used for all reagent transfers, and multiple negative controls were included in each experiment. In order to minimize carry-over contamination from amplified samples, all specimens were irradiated with UV light after completion of amplification to cross-link the IP-10, which reacts with the PCR product to make it unamplifiable while not interfering with detection (Isaacs et al. (1991) *Nucleic Acids Res*. 19:109–116; Rys and Persing (1993) *J. Clin. Microbiol*. 31:2356–2360).

MSG sequence: For PCR amplification of human-*P. carinii* MSG in clinical samples, the upstream primer used was an equimolar mixture of JKK14 (SEQ ID NO: 17) (corresponding to the residues of 2809–2833 of HMSG33, which is also 2845–2869 of hMSG11) and JKK15 (SEQ ID NO: 18) (corresponding to the residues of 2836–2860 of HMSG32). The downstream primer used was JKK17 (SEQ ID NO: 20) (complementary to the conserved residues 3028–3052 of HMSG33, which is also 3064–3088 of MSG11). In experiments wherein the amplified product was detected using the DELFIA™ system, the downstream primer was biotinylated at the 5' end to allow specific capture of amplified sequences through the use of streptavidin.

PCR amplification was carried out in standard PCR reaction mixture (50 mM KCl, 10 mM Tris, pH 8.0, 0.01% gelatin, 3 mM $MgCl_2$, 400 μM dNTPs (Boehringer Mannheim), 1 μM each oligonucleotide primer, and 0.025 units/μl of Amplitaq (Perkin Elmer Cetus)). The HRI Amp-Stop™ system was used to control carry-over contaminations; IP-10 (a psoralen derivative) (4 μg/μl) was added to each reaction to enable UV cross-linking at the end of the amplification cycle, thereby reducing the possibility of cross contaminating of other samples by amplified products (HRI Research, Inc., Concord, Calif.).

Samples were amplified using one of the following two PCR cycles: (1) an initial denaturation cycle (5 minutes at 94° C.) was followed by 44 cycles of denaturation at 94° C. for 30 seconds, annealing at 65° C. for 1 minute and extension at 72° C. for 2 minutes, followed by a final extension after the last cycle at 72° C. for 5 minutes; (2) an initial denaturation at 96° C. for 1 minute was followed by 43 cycles of denaturation at 95° C. for 1 minute, annealing at 65° C. for 1 minute, and extension at 72° C. for 1 minute, with a final extension time of 10 minutes at 72° C. All specimens were irradiated with UV light after completion of cycling to cross-link the incorporated IP-10.

Mitochondria large subunit rRNA (MRSU): Previously published PCR primers pAZ102-E and pAZ102-H were used to amplify *P. carinii* mitochondrial large subunit rRNA (MRSU) in clinical samples (Wakefield et al. (1990) *Mol. and Biochem. Parasitol*. 43:69–76). Primer pAZ102H was biotinylated at the 5' end to allow streptavidin-mediated capture of the amplified product in experiments wherein the amplified product was detected using the DELFIA™ system. The PCR reaction mixture employed was as above. Samples were amplified using one of the following two PCR cycles: (1) an initial denaturation cycle (2 minutes at 94° C.) was followed by 40 cycles of denaturation at 94° C. for 1.5 minutes, annealing at 55° C. for 1.5 minutes and extension at 72° C. for 2 minutes, followed by a final extension after the last cycle at 72° C. for 5 minutes; (2) an initial denaturation at 96° C. for 1 minute was followed by 43 cycles of denaturation at 95° C. for 1 minute, annealing at 65° C. for 1 minute, and extension at 72° C. for 1 minute, with a final extension time of 10 minutes at 72° C.

D. Detection of Amplified PCR Products

Southern Blotting: Standard southern blotting techniques were used to confirm the PCR results (Tables 2 and 3).

Following agarose gel electrophoresis, PCR products were transferred to Hybond N+ membranes (Amersham, Live Science, Arlington Heights, Ill.). Amplification of human-*P. carinii* MSG was detected using probe JKK16 (SEQ ID NO: 19), which corresponds to residues of 2926–2950 of HMSG33. Amplification of *P. carinii* MRSU was detected using pAZ102-L2 (Wakefield et al. (1990) *Mol. and Biochem. Parasitol.* 43:69–76). Oligonucleotides were labeled with [$\gamma$-$^{32}$P]-ATP by T4 polynucleotide kinase (Ready-to-Go™ Molecular Biology Reagents, Pharmacia Biotech, Denmark). Prehybridization and hybridization were performed overnight at 52° C. in 6×SSPE, 1% sodium dodecyl sulfate (SDS), 10×Denhardts' solution (Research Genetics, Huntsville, Ala.). Filters were washed at 52° C. in 1×SSPE, 0.5% SDS for 30 min, then 0.1×SSPE, 0.5% SDS for 15 minutes.

Time-Resolved Fluorescence: Time-resolved fluorescence detection of amplified sequences was carried out using the DELFIA™ system essentially as described by the manufacturer (EG&G Wallac Co.). Using standard procedures, amplicons with incorporated biotin were immobilized in streptavidin-coated microtiter plate wells and washed. Europium-labeled JKK16 was used to probe for the presence of amplified MSG sequences; europium-labeled pAz102-L2 was used to probe for the presence of amplified RNA sequences. Results are summarized in Tables 4 and 5, in comparison to DFA staining.

F. Comparison of *P. carinii* Detection Methods

Oral wash samples were collected along with sputum, induced sputum or BAL. All samples were evaluated by direct fluorescent antibody (DFA) staining. DFA staining was performed using a commercially available kit per the manufacturer's instructions (Genetics Systems, Seattle, Wash.). Oral wash samples were further tested by PCR, using both primer pairs as detailed above. Summarized results from multiple experiments are shown. Table 2 summarizes the results of a comparison between DFA staining and MSG and MRSU PCR amplification of BAL samples. Table 3 shows the results of a similar comparison using oral wash specimens. Table 4 shows the results of the comparison of samples taken via oral wash; results were determined using the Delfia™ hybridization capture system. Table 5 shows the results of the comparison of samples taken from serum; results were determined using the Delfiam hybridization capture system.

The DFA-/PCR+samples (Table 4) likely represent true positive results based on PCR amplification of corresponding sputum samples or concordance between the two PCR methods. One patient with PCP diagnosed by BAL had a negative PCR of oral wash and sputum by both methods, and negative DFA of induced sputum. These data suggest that PCR performed on oral washes can be an accurate, noninvasive means of diagnosing PCP.

TABLE 2

Results of DFA staining compared to MSG and MRSU gene primer PCR amplification in BAL specimens, as measured by Southern hybridization.

| | No. of BAL specimens | | | |
|---|---|---|---|---|
| | MSG gene primers | | MRSU gene primers | |
| Stain Results | Positive | Negative | Positive | Negative |
| Positive | 7 | 0 | 6 | 1 |
| Negative | 0 | 12 | 0 | 12 |

TABLE 3

Results of DFA staining compared to MSG and MRSU gene primer PCR amplification in oral wash specimens, as measured by Southern hybridization.

| | No. of oral wash specimens | | | |
|---|---|---|---|---|
| | MSG gene primers | | MRSU gene primers | |
| Stain Results | Positive | Negative | Positive | Negative |
| Positive | 4 | 4 | 3 | 5 |
| Negative | 3 | 70 | 0 | 73 |

TABLE 4

Results of DFA staining compared to MSG and MRSU gene primer PCR amplification in oral wash specimens, as measured by Delfia ™ hybridization capture assay.

| | No. of oral wash specimens | | | |
|---|---|---|---|---|
| | MSG gene primers | | MRSU gene primers | |
| Stain Results | Positive | Negative | Positive | Negative |
| Positive | 11 | 0 | 9 | 2 |
| Negative | 4 | 157 | 3 | 158 |

TABLE 5

Results of DFA staining compared to MSG and MRSU gene primer PCR amplification in blood serum specimens, as measured by Delfia ™ hybridization capture assay.

| | No. of serum specimens | | | |
|---|---|---|---|---|
| | MSG gene primers | | MRSU gene primers | |
| Stain Results | Positive | Negative | Positive | Negative |
| Positive | 3 | 0 | 2 | 1 |
| Negative | 0 | 7 | 0 | 7 |

The sensitivity of the PCR assay was tested quantitatively by serial dilution of DNA isolated from an autopsy lung sample of an HIV-infected patient with *P. carinii* pneumonia (as above). From this DNA preparation, amplified PCR product could be generated with the MSG gene primers (JKK 14, JKK 15 and JKK 17) using about as little as 16 fg of genomic DNA containing human *P. carinii* DNA as the template. This amount indicates that MSG gene amplification is about 10 to 100 fold more sensitive than amplification using the large subunit rRNA gene primers (pAZ102-E and pAZ102-H). This calculation is based on total DNA, the vast majority of which is human DNA, not *P. carinii* DNA, since there is no good method for purifying human-*P. carinii* away from the human DNA in a single sample. Amounts of DNA were measured by spectrophotometry.

The foregoing examples are provided by way of illustration only. One of skill in the art will appreciate that numerous variations on the biological molecules and methods described above may be employed to make and use oligonucleotide primers for the amplification of human-*P. carinii* MSG-encoding sequences, and for their use in detection and diagnosis of *P. carinii* in clinical samples. We claim all such subject matter that falls within the scope and spirit of the following claims.

We claim:

1. A method of detecting the presence of *Pneumocystis carinii* in a human biological specimen, comprising:

amplifying a highly conserved region within a human-*P. carinii* nucleic acid sequence, if such sequence is present in the specimen, using two or more oligonucleotide primers that hybridize to the highly conserved region; and determining whether an amplified sequence is present, wherein the highly conserved region comprises a sequence selected from the group consisting of residues 2794–3042 of HMSGp1 (SEQ ID NO: 1), 2758–3006 of HMSCp3 (SEQ ID NO: 3), 2845–3090 of HMSG11 (SEQ ID NO: 5), 2839–3084 of HMSG14 (SEQ ID NO: 7), 2836–3081 of HMSG32 (SEQ ID NO: 9), 2809–3054 of HMSG33 (SEQ ID NO: 11), or 1–249 of HMSGp2 (SEQ ID NO: 15): residues 2821–3072 of HMSG35 (SEQ ID NO: 13);

and wherein at least one oligonucleotide primer consists of SEO ID NO: 17 or 18;

and wherein the presence of the amnplified sequence detects the presence of *Pneumocystis carinii* in the human biological specimen.

2. The method according to claim 1, wherein amplification of the human-*P. carinii* nucleic acid sequence is by polymerase chain reaction.

3. The method of claim 1, wherein the oligonucleotide primers hybridize under low stringency conditions comprising 50° C. in 6×SSC, 5x Denhardt's solution, 0.5% SDS and 100 $\mu$g sheared salmon testes DNA.

4. The method of claim 1, wherein the oligonucleotide primers hybridize under stringent conditions comprising 65° C. in 6×SSC, 5x Denhardt's solution, 0.5% SDS and 100 $\mu$g sheared salmon testes DNA.

5. The method of claim 1, wherein the oligonucleotide primers consist of one upstream primer and one downstream primer.

6. The method of claim 5, wherein:

the upstream primer is SEQ ID NO: 17, or SEQ ID NO: 18; and the downstream primer is SEQ ID NO: 20 or SEQ ID NO: 24.

7. The method of claim 1, wherein one of the oligonucleotide primers is SEQ ID NO: 17.

8. The method of claim 1, wherein one of the oligonucleotide primers is SEQ ID NO: 18.

9. The method of claim 1, wherein the specimen is from the oropharyngeal tract.

10. The method of claim 1, wherein the specimen is from blood.

11. The method of claim 1, wherein the step of determining whether an amplified sequence is present comprises one or more of:

(a) electrophoresis and staining of the amplified sequence; or (b) hybridization to a labeled probe of the amplified sequence.

12. The method of claim 11, wherein the amplified sequence is detected by hybridization to a labeled probe.

13. The method of claim 12, wherein the labeled probe comprises a detectable non-isotopic label chosen from the group consisting of:

a fluorescent molecule;

a chemiluminescent molecule;

an enzyme;

a co-factor;

an enzyme substrate; and a hapten.

14. The method of claim 12, wherein the labeled probe comprises SEQ ID NO: 19.

* * * * *

UNITED STATES PATENT AND TRADEMARK OFFICE

CERTIFICATE OF CORRECTION

PATENT NO. : 6,664,053 B1
DATED : December 16, 2003
INVENTOR(S) : Kovacs et al.

It is certified that error appears in the above-identified patent and that said Letters Patent is hereby corrected as shown below:

Column 1,
Line 15, “flourscent” should read -- fluorescent --.

Column 2,
Line 2, “451453” should read -- 451-453 --.
Line 55, “The” should read -- They --.

Column 4,
Line 16, “including” should read -- include --.
Line 67, “HuMSG11” should read -- HMSG11 --.

Column 5,
Line 4, “HuMSG14” should read -- HMSG14 --.
Line 8, “HuMSG32” should read -- HMSG32 --.
Line 12, “HuMSG33” should read -- HMSG33 --.
Line 44, “SEQ ID NO:25” should read -- SEQ ID NO: 25 --.

Column 6,
Line 29, “amount normal” should read -- amount of normal --.

Column 8,
Line 3, “1545-237” should read -- 1545-2371 --.
Line 61, “403410” should read -- 403-410 --.
Line 65, “403410” should read -- 403-410 --.

Column 9,
Line 22, “instances” should read -- instance --.

Column 11,
Line 24, “TIT” should read -- TTT --.
Line 26, “5°” should read -- 5’ --.

Column 12,
Line 21, the following subheading is missing: -- b. MSG Sequence Variants --.

Column 14,
Line 36, “*Med*” should read -- *Med.* --.

UNITED STATES PATENT AND TRADEMARK OFFICE

CERTIFICATE OF CORRECTION

PATENT NO. : 6,664,053 B1
DATED : December 16, 2003
INVENTOR(S) : Kovacs et al.

It is certified that error appears in the above-identified patent and that said Letters Patent is hereby corrected as shown below:

Column 15,
Line 49, "human *P. carinii*" should read -- human-*P. carinii* --.

Column 16,
Line 26, "JKH14, JKH15" should read -- JKK14, JKK15 --.

Column 17,
Line 51, "PCP. in" should read -- PCP. In --.

Column 18,
Line 18, "IKK17" should read -- JKK17 --.

Column 19,
Line 61, "fiill-length" should read -- full-length --.

Column 20,
Line 2, "3092-3 101" should read -- 3092-3101 --.
Line 17, "full length" should read -- full-length --.
Line 31, "human *P. carinii*" should read -- human-*P. carinii* --.

Column 21,
Line 22, "5-galactosidase" should read -- β-galactosidase --.
Line 40, "PET 28A" should read -- pET-28a --.

Column 22,
Line 7, "pg" should read -- $\mu$g --.

Column 23,
Line 14, "tetR" should read -- $tet^R$ --.
Line 17, "tetr" should read -- $tet^R$ --.
Line 58, "pL" should read -- $\mu$L --.

Column 24,
Line 51, "pAZ012H" should read -- pAZ102-H --.

UNITED STATES PATENT AND TRADEMARK OFFICE

CERTIFICATE OF CORRECTION

PATENT NO. : 6,664,053 B1 
DATED : December 16, 2003
INVENTOR(S) : Kovacs et al.

It is certified that error appears in the above-identified patent and that said Letters Patent is hereby corrected as shown below:

Column 115,
Line 13, "HMSCp3" should read -- HMSGp3 --.
Line 20, "SEO" should read -- SEQ --.
Line 21, "amnplified" should read -- amplified --.

Signed and Sealed this

Twenty-fifth Day of January, 2005

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 3042
<212> TYPE: DNA
<213> ORGANISM: Pneumocystis carinii sp. f. hominis
<220> FEATURE:
<221> NAME/KEY: CDS
<222> LOCATION: (1)..(3042)

<400> SEQUENCE: 1

gtg gcg cgg gcg gtt aag cgg cag gta aca gga gca tca gga gta gat       48
Val Ala Arg Ala Val Lys Arg Gln Val Thr Gly Ala Ser Gly Val Asp
  1               5                  10                  15

gag gag gaa gtg cgt ctt ttg gct tta ata cta aaa gaa gat tct aag       96
Glu Glu Glu Val Arg Leu Leu Ala Leu Ile Leu Lys Glu Asp Ser Lys
             20                  25                  30

gat gat aaa aaa tgc gaa gaa aaa tta gaa aaa cat tgc aaa gaa tta      144
Asp Asp Lys Lys Cys Glu Glu Lys Leu Glu Lys His Cys Lys Glu Leu
         35                  40                  45

agt gaa gca aat cta act cca gaa caa gta cat gaa aag tta aaa gat      192
Ser Glu Ala Asn Leu Thr Pro Glu Gln Val His Glu Lys Leu Lys Asp
     50                  55                  60

ttc tgt gat agc aaa aaa cgt gat aaa aaa tgt aaa gaa cta aaa aaa      240
Phe Cys Asp Ser Lys Lys Arg Asp Lys Lys Cys Lys Glu Leu Lys Lys
 65                  70                  75                  80

aat gtt gaa aaa aaa tgc ggt gat ttt aaa aca gaa tta gaa gaa ttg      288
Asn Val Glu Lys Lys Cys Gly Asp Phe Lys Thr Glu Leu Glu Glu Leu
                 85                  90                  95

gtg aaa aag gaa gct tca aat ttg aaa aat gat gag tgt aca aaa aat      336
Val Lys Lys Glu Ala Ser Asn Leu Lys Asn Asp Glu Cys Thr Lys Asn
            100                 105                 110

gaa caa cag tgc ttg ttt tta gaa gaa gca tgc tct gat ctt aca aag      384
Glu Gln Gln Cys Leu Phe Leu Glu Glu Ala Cys Ser Asp Leu Thr Lys
        115                 120                 125

aat tgc aac gat tta aga aac aaa tgt tat cag aat aag cgt gat aag      432
Asn Cys Asn Asp Leu Arg Asn Lys Cys Tyr Gln Asn Lys Arg Asp Lys
    130                 135                 140

gta gca aag gaa gtt ctt tta aga ata ata aaa gga aag aat ttt aaa      480
Val Ala Lys Glu Val Leu Leu Arg Ile Ile Lys Gly Lys Asn Phe Lys
145                 150                 155                 160

gat aaa aat tca tgt gaa aat aaa ctg gaa gta tac tgt caa gaa tta      528
Asp Lys Asn Ser Cys Glu Asn Lys Leu Glu Val Tyr Cys Gln Glu Leu
                165                 170                 175

agt caa atg agt gac gaa ttg atg aaa tta tgt ttt gat caa aaa aat      576
Ser Gln Met Ser Asp Glu Leu Met Lys Leu Cys Phe Asp Gln Lys Asn
            180                 185                 190

acg tgt gat aat ctt gta aaa gaa acg caa caa aag tgt gaa tct ttc      624
Thr Cys Asp Asn Leu Val Lys Glu Thr Gln Gln Lys Cys Glu Ser Phe
        195                 200                 205

aaa aat ctt aaa acg gaa att aaa aca ata aag gaa gat gaa caa cta      672
Lys Asn Leu Lys Thr Glu Ile Lys Thr Ile Lys Glu Asp Glu Gln Leu
    210                 215                 220

aaa aaa aaa tgc cca tta tta tat gaa gaa tgc att ttt tat gat gaa      720
Lys Lys Lys Cys Pro Leu Leu Tyr Glu Glu Cys Ile Phe Tyr Asp Glu
225                 230                 235                 240

agt tgt gga aac gat tca ctg aag tgt agt gaa ttg gaa aaa aaa tgt      768
Ser Cys Gly Asn Asp Ser Leu Lys Cys Ser Glu Leu Glu Lys Lys Cys
                245                 250                 255
```

-continued

```
caa gag aaa aat att act tac aca tta tca tat tca ggg ttt gat cct      816
Gln Glu Lys Asn Ile Thr Tyr Thr Leu Ser Tyr Ser Gly Phe Asp Pro
            260                 265                 270

ata gaa cca gaa att aca tta gca gaa gaa gta gac tta gaa gga att      864
Ile Glu Pro Glu Ile Thr Leu Ala Glu Glu Val Asp Leu Glu Gly Ile
        275                 280                 285

tat aga aag gca gca gaa gaa gga act ctt gtt ggg aaa cct tta cca      912
Tyr Arg Lys Ala Ala Glu Glu Gly Thr Leu Val Gly Lys Pro Leu Pro
    290                 295                 300

gca gat gct act gct ttg gtg gca ttt ttg att caa gat cca tct ctt      960
Ala Asp Ala Thr Ala Leu Val Ala Phe Leu Ile Gln Asp Pro Ser Leu
305                 310                 315                 320

aca act caa cga act aac aaa gaa aaa tgt aaa aaa att ctt gaa gat     1008
Thr Thr Gln Arg Thr Asn Lys Glu Lys Cys Lys Lys Ile Leu Glu Asp
                325                 330                 335

aaa tgt aaa aat tta aaa gaa cat gat att ata aaa ggt cta tgc gag     1056
Lys Cys Lys Asn Leu Lys Glu His Asp Ile Ile Lys Gly Leu Cys Glu
            340                 345                 350

gat tat aat gca aat aaa gat aag gac aaa aaa tgc gaa gaa ctt agt     1104
Asp Tyr Asn Ala Asn Lys Asp Lys Asp Lys Lys Cys Glu Glu Leu Ser
        355                 360                 365

aca gat att gaa gaa aca tgt aaa ttt ttc att tca aaa acc ctt atg     1152
Thr Asp Ile Glu Glu Thr Cys Lys Phe Phe Ile Ser Lys Thr Leu Met
    370                 375                 380

att cat ttt ttt ggc gat gga aat aaa aat gat gga att att aaa tgg     1200
Ile His Phe Phe Gly Asp Gly Asn Lys Asn Asp Gly Ile Ile Lys Trp
385                 390                 395                 400

ggg aat tta tca acg ttt cta agc aat aaa gat tgt aca aaa tta gaa     1248
Gly Asn Leu Ser Thr Phe Leu Ser Asn Lys Asp Cys Thr Lys Leu Glu
                405                 410                 415

tcg tat tgt ctt tat ttt gaa aaa agc tgt aga agc gaa act gca tgc     1296
Ser Tyr Cys Leu Tyr Phe Glu Lys Ser Cys Arg Ser Glu Thr Ala Cys
            420                 425                 430

aag aat atc aga gca gca tgc tac aag aga gga ctt gac aca tta gca     1344
Lys Asn Ile Arg Ala Ala Cys Tyr Lys Arg Gly Leu Asp Thr Leu Ala
        435                 440                 445

aat gaa gta tta caa aaa gaa atg cga gga atg ctg cat ggt tca aat     1392
Asn Glu Val Leu Gln Lys Glu Met Arg Gly Met Leu His Gly Ser Asn
    450                 455                 460

aaa aca tgg ctt agt ggt ttc caa aaa aaa ctc ata gaa gtg tgc aaa     1440
Lys Thr Trp Leu Ser Gly Phe Gln Lys Lys Leu Ile Glu Val Cys Lys
465                 470                 475                 480

aaa gtg aaa aaa gag aat aaa gga gtt ttt ccg agt aat gaa tta ttt     1488
Lys Val Lys Lys Glu Asn Lys Gly Val Phe Pro Ser Asn Glu Leu Phe
                485                 490                 495

gtc tta tgt gta caa cca tca aaa gca gct cga ttg ctt tcg cat gat     1536
Val Leu Cys Val Gln Pro Ser Lys Ala Ala Arg Leu Leu Ser His Asp
            500                 505                 510

ctt cgg atg aaa act atc ttt ttg caa gac gat ttg aac aga aag cga     1584
Leu Arg Met Lys Thr Ile Phe Leu Gln Asp Asp Leu Asn Arg Lys Arg
        515                 520                 525

gat ttt cca gtg aaa gaa gac tgc gaa gaa tta tta aag aaa tgt gag     1632
Asp Phe Pro Val Lys Glu Asp Cys Glu Glu Leu Leu Lys Lys Cys Glu
    530                 535                 540

gct cta aga aag gat tct aaa aaa att gaa tgg cca tgt cat aca tta     1680
Ala Leu Arg Lys Asp Ser Lys Lys Ile Glu Trp Pro Cys His Thr Leu
545                 550                 555                 560

agc caa aat tgt gat caa ttg aga aac gct aaa gaa ttg aaa gaa ctt     1728
Ser Gln Asn Cys Asp Gln Leu Arg Asn Ala Lys Glu Leu Lys Glu Leu
                565                 570                 575
```

-continued

```
tta cta aat gaa cat aag gat ata ttg aaa aat caa gag aat tgt gga     1776
Leu Leu Asn Glu His Lys Asp Ile Leu Lys Asn Gln Glu Asn Cys Gly
            580                 585                 590

atg tat ttg aag gag aaa tgc aat gaa tgg tct aga agg aga aat gaa     1824
Met Tyr Leu Lys Glu Lys Cys Asn Glu Trp Ser Arg Arg Arg Asn Glu
        595                 600                 605

cgt ttc tct ctt tta tgt gct ttg caa aat agg act tgc aga ata atg     1872
Arg Phe Ser Leu Leu Cys Ala Leu Gln Asn Arg Thr Cys Arg Ile Met
    610                 615                 620

gta gaa gat gtg aaa aat caa tgc aaa ata ttt gaa aaa aac att aaa     1920
Val Glu Asp Val Lys Asn Gln Cys Lys Ile Phe Glu Lys Asn Ile Lys
625                 630                 635                 640

aaa tac caa ggt att gat agt aaa act aaa ata gaa gaa tta ggg aca     1968
Lys Tyr Gln Gly Ile Asp Ser Lys Thr Lys Ile Glu Glu Leu Gly Thr
                645                 650                 655

tat tgt cct att tgg cac cca cac tgc cat aga ttt gga ccc aat tgc     2016
Tyr Cys Pro Ile Trp His Pro His Cys His Arg Phe Gly Pro Asn Cys
            660                 665                 670

ccg gat ctt gaa aaa aat aaa tgt gaa gac ttt gaa aaa tat tgc aaa     2064
Pro Asp Leu Glu Lys Asn Lys Cys Glu Asp Phe Glu Lys Tyr Cys Lys
        675                 680                 685

cct tat tat aag caa aga gac ctt gaa aat gca ctt ata ttt gag ttt     2112
Pro Tyr Tyr Lys Gln Arg Asp Leu Glu Asn Ala Leu Ile Phe Glu Phe
    690                 695                 700

aga gga cat ctt gat aag aaa aaa aac tgc aaa aca aat ctt gat aag     2160
Arg Gly His Leu Asp Lys Lys Lys Asn Cys Lys Thr Asn Leu Asp Lys
705                 710                 715                 720

tac tgt aca cta tgg gat caa aca gga aat aaa aca ctt aaa ggt ttt     2208
Tyr Cys Thr Leu Trp Asp Gln Thr Gly Asn Lys Thr Leu Lys Gly Phe
                725                 730                 735

tgt aac agt tct act gat aac aat gaa aca ttt aga gat aaa ctt tgc     2256
Cys Asn Ser Ser Thr Asp Asn Asn Glu Thr Phe Arg Asp Lys Leu Cys
            740                 745                 750

gaa aaa cta gtt cag cgt gtg aaa gaa aaa tgc caa gga tta tca aaa     2304
Glu Lys Leu Val Gln Arg Val Lys Glu Lys Cys Gln Gly Leu Ser Lys
        755                 760                 765

gaa ctt gaa aaa gca aaa aat gat tta gaa gaa aaa cat aaa gat tat     2352
Glu Leu Glu Lys Ala Lys Asn Asp Leu Glu Glu Lys His Lys Asp Tyr
    770                 775                 780

gaa aaa gta aaa aag gat aca aaa aat gca atg gaa gaa aca aat ctc     2400
Glu Lys Val Lys Lys Asp Thr Lys Asn Ala Met Glu Glu Thr Asn Leu
785                 790                 795                 800

gtt ttt tca aca act aaa tca aca gat aat aaa aca gaa aaa gga gtc     2448
Val Phe Ser Thr Thr Lys Ser Thr Asp Asn Lys Thr Glu Lys Gly Val
                805                 810                 815

aag cct agt acg cct agt gta gtt caa gat att gta cat ttt aaa ctt     2496
Lys Pro Ser Thr Pro Ser Val Val Gln Asp Ile Val His Phe Lys Leu
            820                 825                 830

gta aaa aga aat gaa aaa gtt caa gtg aca gaa aaa gaa gca aaa gcg     2544
Val Lys Arg Asn Glu Lys Val Gln Val Thr Glu Lys Glu Ala Lys Ala
        835                 840                 845

ttt gat ttg gta gca cta gca ttc agt ctt tat gta gag tta aaa gaa     2592
Phe Asp Leu Val Ala Leu Ala Phe Ser Leu Tyr Val Glu Leu Lys Glu
    850                 855                 860

acg tgt cac cat cta aag gat gat tgc gaa ttt aga aaa gaa tgt aaa     2640
Thr Cys His His Leu Lys Asp Asp Cys Glu Phe Arg Lys Glu Cys Lys
865                 870                 875                 880

tgt aaa gac cag tgc aaa gag ata gaa aaa ata tgt tta aaa ata gaa     2688
Cys Lys Asp Gln Cys Lys Glu Ile Glu Lys Ile Cys Leu Lys Ile Glu
```

-continued

```
                885                 890                 895

cca ctg aaa gta aag cca cat gaa ata aaa aca gta acg gaa acc aac     2736
Pro Leu Lys Val Lys Pro His Glu Ile Lys Thr Val Thr Glu Thr Asn
            900                 905                 910

ata aca aca gtc aca gaa aca gtc aaa gaa gca gaa aaa aca gta gga     2784
Ile Thr Thr Val Thr Glu Thr Val Lys Glu Ala Glu Lys Thr Val Gly
        915                 920                 925

gac gga gag aaa tgc aaa tct ctc agc aca aca gac acg tgg gtc aca     2832
Asp Gly Glu Lys Cys Lys Ser Leu Ser Thr Thr Asp Thr Trp Val Thr
    930                 935                 940

aag acg tca acc cat acc agc acc tcc acg act acg tcc aca gtt acg     2880
Lys Thr Ser Thr His Thr Ser Thr Ser Thr Thr Thr Ser Thr Val Thr
945                 950                 955                 960

tca aga ata aca ctg acc tcg acg agg cgg tgt aag cct acg aag tgt     2928
Ser Arg Ile Thr Leu Thr Ser Thr Arg Arg Cys Lys Pro Thr Lys Cys
                965                 970                 975

acg aca gga gag gaa gat gaa gca gga gag gtg aag ccg agt gag ggg     2976
Thr Thr Gly Glu Glu Asp Glu Ala Gly Glu Val Lys Pro Ser Glu Gly
            980                 985                 990

ctg agg atg agt ggg tgg agt gtg atg aga ggg gtg tta tta gca atg     3024
Leu Arg Met Ser Gly Trp Ser Val Met Arg Gly Val Leu Leu Ala Met
        995                1000                1005

atg att tca ttc atg att                                             3042
Met Ile Ser Phe Met Ile
   1010


<210> SEQ ID NO 2
<211> LENGTH: 1014
<212> TYPE: PRT
<213> ORGANISM: Pneumocystis carinii sp. f. hominis

<400> SEQUENCE: 2

Val Ala Arg Ala Val Lys Arg Gln Val Thr Gly Ala Ser Gly Val Asp
  1               5                  10                  15

Glu Glu Glu Val Arg Leu Leu Ala Leu Ile Leu Lys Glu Asp Ser Lys
            20                  25                  30

Asp Asp Lys Lys Cys Glu Glu Lys Leu Glu Lys His Cys Lys Glu Leu
        35                  40                  45

Ser Glu Ala Asn Leu Thr Pro Glu Gln Val His Glu Lys Leu Lys Asp
    50                  55                  60

Phe Cys Asp Ser Lys Lys Arg Asp Lys Lys Cys Lys Glu Leu Lys Lys
 65                  70                  75                  80

Asn Val Glu Lys Lys Cys Gly Asp Phe Lys Thr Glu Leu Glu Glu Leu
                85                  90                  95

Val Lys Lys Glu Ala Ser Asn Leu Lys Asn Asp Glu Cys Thr Lys Asn
            100                 105                 110

Glu Gln Gln Cys Leu Phe Leu Glu Glu Ala Cys Ser Asp Leu Thr Lys
        115                 120                 125

Asn Cys Asn Asp Leu Arg Asn Lys Cys Tyr Gln Asn Lys Arg Asp Lys
    130                 135                 140

Val Ala Lys Glu Val Leu Leu Arg Ile Ile Lys Gly Lys Asn Phe Lys
145                 150                 155                 160

Asp Lys Asn Ser Cys Glu Asn Lys Leu Glu Val Tyr Cys Gln Glu Leu
                165                 170                 175

Ser Gln Met Ser Asp Glu Leu Met Lys Leu Cys Phe Asp Gln Lys Asn
            180                 185                 190

Thr Cys Asp Asn Leu Val Lys Glu Thr Gln Gln Lys Cys Glu Ser Phe
```

-continued

```
        195                 200                 205

Lys Asn Leu Lys Thr Glu Ile Lys Thr Ile Lys Glu Asp Glu Gln Leu
    210                 215                 220

Lys Lys Lys Cys Pro Leu Leu Tyr Glu Glu Cys Ile Phe Tyr Asp Glu
225                 230                 235                 240

Ser Cys Gly Asn Asp Ser Leu Lys Cys Ser Glu Leu Glu Lys Lys Cys
                245                 250                 255

Gln Glu Lys Asn Ile Thr Tyr Thr Leu Ser Tyr Ser Gly Phe Asp Pro
            260                 265                 270

Ile Glu Pro Glu Ile Thr Leu Ala Glu Glu Val Asp Leu Glu Gly Ile
        275                 280                 285

Tyr Arg Lys Ala Ala Glu Glu Gly Thr Leu Val Gly Lys Pro Leu Pro
    290                 295                 300

Ala Asp Ala Thr Ala Leu Val Ala Phe Leu Ile Gln Asp Pro Ser Leu
305                 310                 315                 320

Thr Thr Gln Arg Thr Asn Lys Glu Lys Cys Lys Lys Ile Leu Glu Asp
                325                 330                 335

Lys Cys Lys Asn Leu Lys Glu His Asp Ile Ile Lys Gly Leu Cys Glu
            340                 345                 350

Asp Tyr Asn Ala Asn Lys Asp Lys Asp Lys Lys Cys Glu Glu Leu Ser
        355                 360                 365

Thr Asp Ile Glu Glu Thr Cys Lys Phe Phe Ile Ser Lys Thr Leu Met
    370                 375                 380

Ile His Phe Phe Gly Asp Gly Asn Lys Asn Asp Gly Ile Ile Lys Trp
385                 390                 395                 400

Gly Asn Leu Ser Thr Phe Leu Ser Asn Lys Asp Cys Thr Lys Leu Glu
                405                 410                 415

Ser Tyr Cys Leu Tyr Phe Glu Lys Ser Cys Arg Ser Glu Thr Ala Cys
            420                 425                 430

Lys Asn Ile Arg Ala Ala Cys Tyr Lys Arg Gly Leu Asp Thr Leu Ala
        435                 440                 445

Asn Glu Val Leu Gln Lys Glu Met Arg Gly Met Leu His Gly Ser Asn
    450                 455                 460

Lys Thr Trp Leu Ser Gly Phe Gln Lys Lys Leu Ile Glu Val Cys Lys
465                 470                 475                 480

Lys Val Lys Lys Glu Asn Lys Gly Val Phe Pro Ser Asn Glu Leu Phe
                485                 490                 495

Val Leu Cys Val Gln Pro Ser Lys Ala Ala Arg Leu Leu Ser His Asp
            500                 505                 510

Leu Arg Met Lys Thr Ile Phe Leu Gln Asp Asp Leu Asn Arg Lys Arg
        515                 520                 525

Asp Phe Pro Val Lys Glu Asp Cys Glu Glu Leu Leu Lys Lys Cys Glu
    530                 535                 540

Ala Leu Arg Lys Asp Ser Lys Lys Ile Glu Trp Pro Cys His Thr Leu
545                 550                 555                 560

Ser Gln Asn Cys Asp Gln Leu Arg Asn Ala Lys Glu Leu Lys Glu Leu
                565                 570                 575

Leu Leu Asn Glu His Lys Asp Ile Leu Lys Asn Gln Glu Asn Cys Gly
            580                 585                 590

Met Tyr Leu Lys Glu Lys Cys Asn Glu Trp Ser Arg Arg Arg Asn Glu
        595                 600                 605

Arg Phe Ser Leu Leu Cys Ala Leu Gln Asn Arg Thr Cys Arg Ile Met
    610                 615                 620
```

-continued

```
Val Glu Asp Val Lys Asn Gln Cys Lys Ile Phe Glu Lys Asn Ile Lys
625                 630                 635                 640

Lys Tyr Gln Gly Ile Asp Ser Lys Thr Lys Ile Glu Glu Leu Gly Thr
                645                 650                 655

Tyr Cys Pro Ile Trp His Pro His Cys His Arg Phe Gly Pro Asn Cys
            660                 665                 670

Pro Asp Leu Glu Lys Asn Lys Cys Glu Asp Phe Glu Lys Tyr Cys Lys
        675                 680                 685

Pro Tyr Tyr Lys Gln Arg Asp Leu Glu Asn Ala Leu Ile Phe Glu Phe
    690                 695                 700

Arg Gly His Leu Asp Lys Lys Lys Asn Cys Lys Thr Asn Leu Asp Lys
705                 710                 715                 720

Tyr Cys Thr Leu Trp Asp Gln Thr Gly Asn Lys Thr Leu Lys Gly Phe
                725                 730                 735

Cys Asn Ser Ser Thr Asp Asn Asn Glu Thr Phe Arg Asp Lys Leu Cys
            740                 745                 750

Glu Lys Leu Val Gln Arg Val Lys Glu Lys Cys Gln Gly Leu Ser Lys
        755                 760                 765

Glu Leu Glu Lys Ala Lys Asn Asp Leu Glu Glu Lys His Lys Asp Tyr
    770                 775                 780

Glu Lys Val Lys Lys Asp Thr Lys Asn Ala Met Glu Glu Thr Asn Leu
785                 790                 795                 800

Val Phe Ser Thr Thr Lys Ser Thr Asp Asn Lys Thr Glu Lys Gly Val
                805                 810                 815

Lys Pro Ser Thr Pro Ser Val Val Gln Asp Ile Val His Phe Lys Leu
            820                 825                 830

Val Lys Arg Asn Glu Lys Val Gln Val Thr Glu Lys Glu Ala Lys Ala
        835                 840                 845

Phe Asp Leu Val Ala Leu Ala Phe Ser Leu Tyr Val Glu Leu Lys Glu
    850                 855                 860

Thr Cys His His Leu Lys Asp Asp Cys Glu Phe Arg Lys Glu Cys Lys
865                 870                 875                 880

Cys Lys Asp Gln Cys Lys Glu Ile Glu Lys Ile Cys Leu Lys Ile Glu
                885                 890                 895

Pro Leu Lys Val Lys Pro His Glu Ile Lys Thr Val Thr Glu Thr Asn
            900                 905                 910

Ile Thr Thr Val Thr Glu Thr Val Lys Glu Ala Glu Lys Thr Val Gly
        915                 920                 925

Asp Gly Glu Lys Cys Lys Ser Leu Ser Thr Thr Asp Thr Trp Val Thr
    930                 935                 940

Lys Thr Ser Thr His Thr Ser Thr Ser Thr Thr Thr Ser Thr Val Thr
945                 950                 955                 960

Ser Arg Ile Thr Leu Thr Ser Thr Arg Arg Cys Lys Pro Thr Lys Cys
                965                 970                 975

Thr Thr Gly Glu Glu Asp Glu Ala Gly Glu Val Lys Pro Ser Glu Gly
            980                 985                 990

Leu Arg Met Ser Gly Trp Ser Val Met Arg Gly Val Leu Leu Ala Met
        995                1000                1005

Met Ile Ser Phe Met Ile
   1010
```

<210> SEQ ID NO 3
<211> LENGTH: 3006

-continued

<212> TYPE: DNA
<213> ORGANISM: Pneumocystis carinii sp. f. hominis
<220> FEATURE:
<221> NAME/KEY: CDS
<222> LOCATION: (1)..(3006)

<400> SEQUENCE: 3 gtg gcg cgg gcg gtc aag cgg cgg gct gca gca cag aat agt gtt gaa 48
Val Ala Arg Ala Val Lys Arg Arg Ala Ala Ala Gln Asn Ser Val Glu
1 5 10 15 gaa gaa tat ctt ttg gct ttg att tta gaa aat gag tat gaa aat aat 96
Glu Glu Tyr Leu Leu Ala Leu Ile Leu Glu Asn Glu Tyr Glu Asn Asn
20 25 30 gat aaa tgt aaa aaa agg ttg aaa gag tat tgt gaa gtt tta aaa aat 144
Asp Lys Cys Lys Lys Arg Leu Lys Glu Tyr Cys Glu Val Leu Lys Asn
35 40 45 gta aca aaa gaa cca aaa aaa cta gaa gaa aag tta gac gga atc tgc 192
Val Thr Lys Glu Pro Lys Lys Leu Glu Glu Lys Leu Asp Gly Ile Cys
50 55 60 aaa gat gat aaa aca ata gaa gca aaa tgc aaa gaa tca gaa aca aag 240
Lys Asp Asp Lys Thr Ile Glu Ala Lys Cys Lys Glu Ser Glu Thr Lys
65 70 75 80 gtt aaa gca aag tgt act agt ttt caa aca gaa ctt gat aaa gca gtc 288
Val Lys Ala Lys Cys Thr Ser Phe Gln Thr Glu Leu Asp Lys Ala Val
85 90 95 aaa aag gga gct tca aca tta gaa gat aat gat tgt aag aag aat gaa 336
Lys Lys Gly Ala Ser Thr Leu Glu Asp Asn Asp Cys Lys Lys Asn Glu
100 105 110 cga caa tgc ctg ttt ttg gag gga gca tgt cca aca gaa ctt aaa gat 384
Arg Gln Cys Leu Phe Leu Glu Gly Ala Cys Pro Thr Glu Leu Lys Asp
115 120 125 aaa tgt aat gaa ctg agg aat aaa tgt tat caa aaa aaa cga gac gac 432
Lys Cys Asn Glu Leu Arg Asn Lys Cys Tyr Gln Lys Lys Arg Asp Asp
130 135 140 gta gca gaa aaa gct ctt tta aga gta ctt aga ggg aac ctt aag gat 480
Val Ala Glu Lys Ala Leu Leu Arg Val Leu Arg Gly Asn Leu Lys Asp
145 150 155 160 aaa aac aca tgc aaa aat aag tta aag ggg gtt tgt caa gaa ttc aac 528
Lys Asn Thr Cys Lys Asn Lys Leu Lys Gly Val Cys Gln Glu Phe Asn
165 170 175 aaa gaa agt gat gag cta ata aaa tta tgt ctt gac gaa gaa aaa acg 576
Lys Glu Ser Asp Glu Leu Ile Lys Leu Cys Leu Asp Glu Glu Lys Thr
180 185 190 tgt gga gat ctt gta tct aag aaa gaa tac aaa tgc aaa cct ctc aaa 624
Cys Gly Asp Leu Val Ser Lys Lys Glu Tyr Lys Cys Lys Pro Leu Lys
195 200 205 gaa gga att gat cta gtg ctt gga aag gaa gat tta tta aaa gaa aaa 672
Glu Gly Ile Asp Leu Val Leu Gly Lys Glu Asp Leu Leu Lys Glu Lys
210 215 220 tgt tta tta ttt ctt gaa gaa tgt tac ttt tat ggg tca aac tgt gaa 720
Cys Leu Leu Phe Leu Glu Glu Cys Tyr Phe Tyr Gly Ser Asn Cys Glu
225 230 235 240 aca gat cag cca aag tgt aaa gag ttt gca agc aaa tgt caa aag gaa 768
Thr Asp Gln Pro Lys Cys Lys Glu Phe Ala Ser Lys Cys Gln Lys Glu
245 250 255 aat ctc gtt tat gca gca cca ggt tca cac ttt gat cct acg aaa tta 816
Asn Leu Val Tyr Ala Ala Pro Gly Ser His Phe Asp Pro Thr Lys Leu
260 265 270 aag att agg tta gca gaa gaa ata gac cta gaa aaa ttg tac gta gaa 864
Lys Ile Arg Leu Ala Glu Glu Ile Asp Leu Glu Lys Leu Tyr Val Glu
275 280 285

-continued

```
gca gtg aaa aag gga att cat att gga agg cca tca ata aaa gat gaa      912
Ala Val Lys Lys Gly Ile His Ile Gly Arg Pro Ser Ile Lys Asp Glu
    290                 295                 300

gtc gct tta ttg gca tta tta agc aag agt gat gct caa aat act ttt      960
Val Ala Leu Leu Ala Leu Leu Ser Lys Ser Asp Ala Gln Asn Thr Phe
305                 310                 315                 320

aaa gat caa tgt gaa gat gtt att aaa aaa aaa tgt gga aac ttt aaa     1008
Lys Asp Gln Cys Glu Asp Val Ile Lys Lys Lys Cys Gly Asn Phe Lys
                325                 330                 335

gag cat att att tta aaa gat tta tgt agt aat aag act atc act gat     1056
Glu His Ile Ile Leu Lys Asp Leu Cys Ser Asn Lys Thr Ile Thr Asp
            340                 345                 350

aat cca aaa gaa aaa tgc gaa gaa cta aat aag gag tta aca acc cgt     1104
Asn Pro Lys Glu Lys Cys Glu Glu Leu Asn Lys Glu Leu Thr Thr Arg
        355                 360                 365

att tta act gtt tct aaa agg att gag aaa tat ttc gct cca gct aat     1152
Ile Leu Thr Val Ser Lys Arg Ile Glu Lys Tyr Phe Ala Pro Ala Asn
    370                 375                 380

gta aag gaa att att ggt tgg cat atg ttg cat aca ttt ctt ggt gaa     1200
Val Lys Glu Ile Ile Gly Trp His Met Leu His Thr Phe Leu Gly Glu
385                 390                 395                 400

aga gag tgt acg aaa ctg ttg tcg gat tgt ttt tat ttg aaa agc caa     1248
Arg Glu Cys Thr Lys Leu Leu Ser Asp Cys Phe Tyr Leu Lys Ser Gln
                405                 410                 415

gct cca ctt gaa aag ccc tgc aat aac tta aaa gca gca tgt tat aaa     1296
Ala Pro Leu Glu Lys Pro Cys Asn Asn Leu Lys Ala Ala Cys Tyr Lys
            420                 425                 430

aaa ggg ctt gaa gca gta gca aat gaa gca tta caa gat aag tta cgg     1344
Lys Gly Leu Glu Ala Val Ala Asn Glu Ala Leu Gln Asp Lys Leu Arg
        435                 440                 445

gga aaa ttg caa ggt tca aat aga aca tgg ctt gaa acc ctt caa aaa     1392
Gly Lys Leu Gln Gly Ser Asn Arg Thr Trp Leu Glu Thr Leu Gln Lys
    450                 455                 460

aac ttg gta aaa gtt tgt gaa aag acg aaa gga gaa agt gat gaa tta     1440
Asn Leu Val Lys Val Cys Glu Lys Thr Lys Gly Glu Ser Asp Glu Leu
465                 470                 475                 480

ttt gta cta tgt atg aac cca ata aaa acg gct ctt aca gtg tca aca     1488
Phe Val Leu Cys Met Asn Pro Ile Lys Thr Ala Leu Thr Val Ser Thr
                485                 490                 495

gat ttg cga atg agg gca gtt gct ttg caa gag cat ttg aac gaa aaa     1536
Asp Leu Arg Met Arg Ala Val Ala Leu Gln Glu His Leu Asn Glu Lys
            500                 505                 510

cga gat ttt cca aca gaa aag gat tgt aaa gaa tta gag aaa aaa tgt     1584
Arg Asp Phe Pro Thr Glu Lys Asp Cys Lys Glu Leu Glu Lys Lys Cys
        515                 520                 525

gag gtc tta gga aaa gat tca aga gaa att aaa tgg tca tgt tat acg     1632
Glu Val Leu Gly Lys Asp Ser Arg Glu Ile Lys Trp Ser Cys Tyr Thr
    530                 535                 540

tta aaa cag cat tgc aat cgg ctg aag agc ata gag cac tta gaa gag     1680
Leu Lys Gln His Cys Asn Arg Leu Lys Ser Ile Glu His Leu Glu Glu
545                 550                 555                 560

gag ttg cta aaa gaa aat aaa gga tat tta aaa gat gaa aat agc tgc     1728
Glu Leu Leu Lys Glu Asn Lys Gly Tyr Leu Lys Asp Glu Asn Ser Cys
                565                 570                 575

aaa gaa gaa gct aag aaa cga tgt gaa aaa tgg ttt aga aga gaa aat     1776
Lys Glu Glu Ala Lys Lys Arg Cys Glu Lys Trp Phe Arg Arg Glu Asn
            580                 585                 590

aat aaa ttt ttt tcg gct tgt tct gac ttg gaa ctt gtt tgc aaa aag     1824
Asn Lys Phe Phe Ser Ala Cys Ser Asp Leu Glu Leu Val Cys Lys Lys
```

-continued

```
        595                 600                 605

atc act aga aat gtt gaa tct aaa tgt aat ata ttg aaa gga cat atg      1872
Ile Thr Arg Asn Val Glu Ser Lys Cys Asn Ile Leu Lys Gly His Met
    610                 615                 620

gaa act atg aac gtt ata agt gaa ata gct aaa aaa gag gaa aaa ata      1920
Glu Thr Met Asn Val Ile Ser Glu Ile Ala Lys Lys Glu Glu Lys Ile
625                 630                 635                 640

tgt gaa ttt tgg gct cca tat tgt aaa aag tac gag caa aat tgt gaa      1968
Cys Glu Phe Trp Ala Pro Tyr Cys Lys Lys Tyr Glu Gln Asn Cys Glu
                645                 650                 655

aaa ctt aaa aac gga gga aaa gat ggg caa tgc aaa aaa ctc aat aaa      2016
Lys Leu Lys Asn Gly Gly Lys Asp Gly Gln Cys Lys Lys Leu Asn Lys
            660                 665                 670

aag tgc aaa tca ttc ctt gaa aaa gaa gct tta gaa aat aaa gtt gta      2064
Lys Cys Lys Ser Phe Leu Glu Lys Glu Ala Leu Glu Asn Lys Val Val
        675                 680                 685

gaa gaa ttg aaa ggt agt tta tca aac gta gga gaa tgt aac aat aca      2112
Glu Glu Leu Lys Gly Ser Leu Ser Asn Val Gly Glu Cys Asn Asn Thr
    690                 695                 700

ctt aat ata tac tgt aca caa ttg aaa aag gca gag aat ggg ttg gaa      2160
Leu Asn Ile Tyr Cys Thr Gln Leu Lys Lys Ala Glu Asn Gly Leu Glu
705                 710                 715                 720

act ttg tgc aaa agc aaa gaa aac acc aag agt gac att aaa gtt aga      2208
Thr Leu Cys Lys Ser Lys Glu Asn Thr Lys Ser Asp Ile Lys Val Arg
                725                 730                 735

gaa gaa ctc tgt gaa aag cta ata aaa cgt ata aaa gaa aaa tgc tca      2256
Glu Glu Leu Cys Glu Lys Leu Ile Lys Arg Ile Lys Glu Lys Cys Ser
            740                 745                 750

aaa ttg aag gac gag ctt gaa gaa gta aaa gag gtc tta gaa aag aaa      2304
Lys Leu Lys Asp Glu Leu Glu Glu Val Lys Glu Val Leu Glu Lys Lys
        755                 760                 765

gaa gaa aag tat aaa aaa att aaa gaa gaa gca gaa aaa gcc atg gaa      2352
Glu Glu Lys Tyr Lys Lys Ile Lys Glu Glu Ala Glu Lys Ala Met Glu
    770                 775                 780

gat gca aac ctt att tta tcg aga gcg aaa gga cct gat aat aat aat      2400
Asp Ala Asn Leu Ile Leu Ser Arg Ala Lys Gly Pro Asp Asn Asn Asn
785                 790                 795                 800

aat aag tca gta aat aaa gac tca tct gat aca cct aag gaa gga aaa      2448
Asn Lys Ser Val Asn Lys Asp Ser Ser Asp Thr Pro Lys Glu Gly Lys
                805                 810                 815

ggc aca aca gga ttt aaa ctt gta aga aga aat gca aaa gtg cat gta      2496
Gly Thr Thr Gly Phe Lys Leu Val Arg Arg Asn Ala Lys Val His Val
            820                 825                 830

aca gaa aaa gaa tta gca gca ttt gat ttg gta gca aga gca ttt gat      2544
Thr Glu Lys Glu Leu Ala Ala Phe Asp Leu Val Ala Arg Ala Phe Asp
        835                 840                 845

ctc tat cta gaa ttg aaa gaa ata tgt aat cat tca ctg aag aat tgt      2592
Leu Tyr Leu Glu Leu Lys Glu Ile Cys Asn His Ser Leu Lys Asn Cys
    850                 855                 860

ggt ttc aaa aaa gag tgt gac tgt gag gat cca tgt aaa aag ata cag      2640
Gly Phe Lys Lys Glu Cys Asp Cys Glu Asp Pro Cys Lys Lys Ile Gln
865                 870                 875                 880

gga ata tgt tca aca tta gag cca cta aaa gtg aga cca cac gaa ata      2688
Gly Ile Cys Ser Thr Leu Glu Pro Leu Lys Val Arg Pro His Glu Ile
                885                 890                 895

gta act aaa aac ata aca act aca acc aca acc acc acc aca act acc      2736
Val Thr Lys Asn Ile Thr Thr Thr Thr Thr Thr Thr Thr Thr Thr Thr
            900                 905                 910

att aaa gac gca aag gca aca gac tgc cac tct tta cag aca aca gat      2784
```

-continued

```
Ile Lys Asp Ala Lys Ala Thr Asp Cys His Ser Leu Gln Thr Thr Asp
        915                 920                 925

acg tgg gtc aca aag acg tcg acc cat act agc aca tcc aca acc aca      2832
Thr Trp Val Thr Lys Thr Ser Thr His Thr Ser Thr Ser Thr Thr Thr
    930                 935                 940

tct aca gtc acg tca aga ata acg ttg acc tcg aca aga cgg tgt aag      2880
Ser Thr Val Thr Ser Arg Ile Thr Leu Thr Ser Thr Arg Arg Cys Lys
945                 950                 955                 960

cct acg aag tgt acg aca gga gag gaa gat gaa gca gga gac gtg aaa      2928
Pro Thr Lys Cys Thr Thr Gly Glu Glu Asp Glu Ala Gly Asp Val Lys
                965                 970                 975

ccg agt gaa ggg ttg agg atg agt gga tgg agt gtg atg agg ggg gtg      2976
Pro Ser Glu Gly Leu Arg Met Ser Gly Trp Ser Val Met Arg Gly Val
            980                 985                 990

tta tta gca atg acg att tca ttc atg att                              3006
Leu Leu Ala Met Thr Ile Ser Phe Met Ile
        995                 1000


<210> SEQ ID NO 4
<211> LENGTH: 1002
<212> TYPE: PRT
<213> ORGANISM: Pneumocystis carinii sp. f. hominis

<400> SEQUENCE: 4

Val Ala Arg Ala Val Lys Arg Arg Ala Ala Ala Gln Asn Ser Val Glu
  1               5                  10                  15

Glu Glu Tyr Leu Leu Ala Leu Ile Leu Glu Asn Glu Tyr Glu Asn Asn
            20                  25                  30

Asp Lys Cys Lys Lys Arg Leu Lys Glu Tyr Cys Glu Val Leu Lys Asn
         35                  40                  45

Val Thr Lys Glu Pro Lys Lys Leu Glu Glu Lys Leu Asp Gly Ile Cys
     50                  55                  60

Lys Asp Asp Lys Thr Ile Glu Ala Lys Cys Lys Glu Ser Glu Thr Lys
 65                  70                  75                  80

Val Lys Ala Lys Cys Thr Ser Phe Gln Thr Glu Leu Asp Lys Ala Val
                85                  90                  95

Lys Lys Gly Ala Ser Thr Leu Glu Asp Asn Asp Cys Lys Lys Asn Glu
            100                 105                 110

Arg Gln Cys Leu Phe Leu Glu Gly Ala Cys Pro Thr Glu Leu Lys Asp
        115                 120                 125

Lys Cys Asn Glu Leu Arg Asn Lys Cys Tyr Gln Lys Lys Arg Asp Asp
    130                 135                 140

Val Ala Glu Lys Ala Leu Leu Arg Val Leu Arg Gly Asn Leu Lys Asp
145                 150                 155                 160

Lys Asn Thr Cys Lys Asn Lys Leu Lys Gly Val Cys Gln Glu Phe Asn
                165                 170                 175

Lys Glu Ser Asp Glu Leu Ile Lys Leu Cys Leu Asp Glu Glu Lys Thr
            180                 185                 190

Cys Gly Asp Leu Val Ser Lys Lys Glu Tyr Lys Cys Lys Pro Leu Lys
        195                 200                 205

Glu Gly Ile Asp Leu Val Leu Gly Lys Glu Asp Leu Leu Lys Glu Lys
    210                 215                 220

Cys Leu Leu Phe Leu Glu Glu Cys Tyr Phe Tyr Gly Ser Asn Cys Glu
225                 230                 235                 240

Thr Asp Gln Pro Lys Cys Lys Glu Phe Ala Ser Lys Cys Gln Lys Glu
                245                 250                 255
```

-continued

```
Asn Leu Val Tyr Ala Ala Pro Gly Ser His Phe Asp Pro Thr Lys Leu
            260                 265                 270

Lys Ile Arg Leu Ala Glu Glu Ile Asp Leu Glu Lys Leu Tyr Val Glu
        275                 280                 285

Ala Val Lys Lys Gly Ile His Ile Gly Arg Pro Ser Ile Lys Asp Glu
    290                 295                 300

Val Ala Leu Leu Ala Leu Leu Ser Lys Ser Asp Ala Gln Asn Thr Phe
305                 310                 315                 320

Lys Asp Gln Cys Glu Asp Val Ile Lys Lys Lys Cys Gly Asn Phe Lys
                325                 330                 335

Glu His Ile Ile Leu Lys Asp Leu Cys Ser Asn Lys Thr Ile Thr Asp
            340                 345                 350

Asn Pro Lys Glu Lys Cys Glu Glu Leu Asn Lys Glu Leu Thr Thr Arg
        355                 360                 365

Ile Leu Thr Val Ser Lys Arg Ile Glu Lys Tyr Phe Ala Pro Ala Asn
    370                 375                 380

Val Lys Glu Ile Ile Gly Trp His Met Leu His Thr Phe Leu Gly Glu
385                 390                 395                 400

Arg Glu Cys Thr Lys Leu Leu Ser Asp Cys Phe Tyr Leu Lys Ser Gln
                405                 410                 415

Ala Pro Leu Glu Lys Pro Cys Asn Asn Leu Lys Ala Ala Cys Tyr Lys
            420                 425                 430

Lys Gly Leu Glu Ala Val Ala Asn Glu Ala Leu Gln Asp Lys Leu Arg
        435                 440                 445

Gly Lys Leu Gln Gly Ser Asn Arg Thr Trp Leu Glu Thr Leu Gln Lys
    450                 455                 460

Asn Leu Val Lys Val Cys Glu Lys Thr Lys Gly Glu Ser Asp Glu Leu
465                 470                 475                 480

Phe Val Leu Cys Met Asn Pro Ile Lys Thr Ala Leu Thr Val Ser Thr
                485                 490                 495

Asp Leu Arg Met Arg Ala Val Ala Leu Gln Glu His Leu Asn Glu Lys
            500                 505                 510

Arg Asp Phe Pro Thr Glu Lys Asp Cys Lys Glu Leu Glu Lys Lys Cys
        515                 520                 525

Glu Val Leu Gly Lys Asp Ser Arg Glu Ile Lys Trp Ser Cys Tyr Thr
    530                 535                 540

Leu Lys Gln His Cys Asn Arg Leu Lys Ser Ile Glu His Leu Glu Glu
545                 550                 555                 560

Glu Leu Leu Lys Glu Asn Lys Gly Tyr Leu Lys Asp Glu Asn Ser Cys
                565                 570                 575

Lys Glu Glu Ala Lys Lys Arg Cys Glu Lys Trp Phe Arg Arg Glu Asn
            580                 585                 590

Asn Lys Phe Phe Ser Ala Cys Ser Asp Leu Glu Leu Val Cys Lys Lys
        595                 600                 605

Ile Thr Arg Asn Val Glu Ser Lys Cys Asn Ile Leu Lys Gly His Met
    610                 615                 620

Glu Thr Met Asn Val Ile Ser Glu Ile Ala Lys Lys Glu Glu Lys Ile
625                 630                 635                 640

Cys Glu Phe Trp Ala Pro Tyr Cys Lys Lys Tyr Glu Gln Asn Cys Glu
                645                 650                 655

Lys Leu Lys Asn Gly Gly Lys Asp Gly Gln Cys Lys Lys Leu Asn Lys
            660                 665                 670

Lys Cys Lys Ser Phe Leu Glu Lys Glu Ala Leu Glu Asn Lys Val Val
```

-continued

```
        675                 680                 685

Glu Glu Leu Lys Gly Ser Leu Ser Asn Val Gly Glu Cys Asn Asn Thr
    690                 695                 700

Leu Asn Ile Tyr Cys Thr Gln Leu Lys Lys Ala Glu Asn Gly Leu Glu
705                 710                 715                 720

Thr Leu Cys Lys Ser Lys Glu Asn Thr Lys Ser Asp Ile Lys Val Arg
                725                 730                 735

Glu Glu Leu Cys Glu Lys Leu Ile Lys Arg Ile Lys Glu Lys Cys Ser
            740                 745                 750

Lys Leu Lys Asp Glu Leu Glu Glu Val Lys Glu Val Leu Glu Lys Lys
        755                 760                 765

Glu Glu Lys Tyr Lys Lys Ile Lys Glu Glu Ala Glu Lys Ala Met Glu
    770                 775                 780

Asp Ala Asn Leu Ile Leu Ser Arg Ala Lys Gly Pro Asp Asn Asn Asn
785                 790                 795                 800

Asn Lys Ser Val Asn Lys Asp Ser Ser Asp Thr Pro Lys Glu Gly Lys
                805                 810                 815

Gly Thr Thr Gly Phe Lys Leu Val Arg Arg Asn Ala Lys Val His Val
            820                 825                 830

Thr Glu Lys Glu Leu Ala Ala Phe Asp Leu Val Ala Arg Ala Phe Asp
        835                 840                 845

Leu Tyr Leu Glu Leu Lys Glu Ile Cys Asn His Ser Leu Lys Asn Cys
    850                 855                 860

Gly Phe Lys Lys Glu Cys Asp Cys Glu Asp Pro Cys Lys Lys Ile Gln
865                 870                 875                 880

Gly Ile Cys Ser Thr Leu Glu Pro Leu Lys Val Arg Pro His Glu Ile
                885                 890                 895

Val Thr Lys Asn Ile Thr Thr Thr Thr Thr Thr Thr Thr Thr Thr Thr
            900                 905                 910

Ile Lys Asp Ala Lys Ala Thr Asp Cys His Ser Leu Gln Thr Thr Asp
        915                 920                 925

Thr Trp Val Thr Lys Thr Ser Thr His Thr Ser Thr Ser Thr Thr Thr
    930                 935                 940

Ser Thr Val Thr Ser Arg Ile Thr Leu Thr Ser Thr Arg Arg Cys Lys
945                 950                 955                 960

Pro Thr Lys Cys Thr Thr Gly Glu Glu Asp Glu Ala Gly Asp Val Lys
                965                 970                 975

Pro Ser Glu Gly Leu Arg Met Ser Gly Trp Ser Val Met Arg Gly Val
            980                 985                 990

Leu Leu Ala Met Thr Ile Ser Phe Met Ile
        995                1000


<210> SEQ ID NO 5
<211> LENGTH: 3090
<212> TYPE: DNA
<213> ORGANISM: Pneumocystis carinii sp. f. hominis
<220> FEATURE:
<221> NAME/KEY: CDS
<222> LOCATION: (1)..(3090)

<400> SEQUENCE: 5

atg gcg cgg gcg gtc aag cgg cgg gca aaa ggt gca cag aat agc att       48
Met Ala Arg Ala Val Lys Arg Arg Ala Lys Gly Ala Gln Asn Ser Ile
  1               5                  10                  15

gat gag gag cat gtt tta gct ttg att tta aaa aaa aat gga tta gaa       96
Asp Glu Glu His Val Leu Ala Leu Ile Leu Lys Lys Asn Gly Leu Glu
```

-continued

```
             20                  25                  30

gat aca aaa tgc aaa act aag ttg gaa gaa tat tgc aaa aca tta aca      144
Asp Thr Lys Cys Lys Thr Lys Leu Glu Glu Tyr Cys Lys Thr Leu Thr
        35                  40                  45

aat gca gga tta aat cca gaa aaa gtt cac gaa aaa tta aaa gat ttc      192
Asn Ala Gly Leu Asn Pro Glu Lys Val His Glu Lys Leu Lys Asp Phe
    50                  55                  60

tgt gat aac ggg aaa cga aat gaa aaa tgt caa gat cta aaa aac aaa      240
Cys Asp Asn Gly Lys Arg Asn Glu Lys Cys Gln Asp Leu Lys Asn Lys
 65                  70                  75                  80

gtc aat caa aaa tgc att aaa ttt caa gga aaa ctt caa aca gct gct      288
Val Asn Gln Lys Cys Ile Lys Phe Gln Gly Lys Leu Gln Thr Ala Ala
                85                  90                  95

gga aaa aaa att tca gaa tta aca gat gag gat tgc aaa aag aat gaa      336
Gly Lys Lys Ile Ser Glu Leu Thr Asp Glu Asp Cys Lys Lys Asn Glu
            100                 105                 110

caa caa tgc cta ttt ttg gag gga gca tgt cca aca gaa ctt aaa gat      384
Gln Gln Cys Leu Phe Leu Glu Gly Ala Cys Pro Thr Glu Leu Lys Asp
        115                 120                 125

gac tgc aat aaa tta agg aat aac tgt tat caa aaa gaa cgg aac aat      432
Asp Cys Asn Lys Leu Arg Asn Asn Cys Tyr Gln Lys Glu Arg Asn Asn
    130                 135                 140

gtg gca gaa gaa gtt ctt ttg agg gcg ctt cgt ggt gat ctc aat gaa      480
Val Ala Glu Glu Val Leu Leu Arg Ala Leu Arg Gly Asp Leu Asn Glu
145                 150                 155                 160

aca aag aca tgt gaa aaa aag ctg aaa gaa gtt tgc ccg aaa tta gaa      528
Thr Lys Thr Cys Glu Lys Lys Leu Lys Glu Val Cys Pro Lys Leu Glu
                165                 170                 175

aga gaa agc gat gaa tta acg gag ctt tgt ctt tat caa aaa aca aca      576
Arg Glu Ser Asp Glu Leu Thr Glu Leu Cys Leu Tyr Gln Lys Thr Thr
            180                 185                 190

tgc gta agt ctt gta aca aaa gga aaa agt aaa tgt gat act ctt gaa      624
Cys Val Ser Leu Val Thr Lys Gly Lys Ser Lys Cys Asp Thr Leu Glu
        195                 200                 205

aaa gaa gtt gaa gaa gca ctt aag aag aat gaa ttg cga gaa aaa tgt      672
Lys Glu Val Glu Glu Ala Leu Lys Lys Asn Glu Leu Arg Glu Lys Cys
    210                 215                 220

cta cta tta ctt gag caa tgt tac ttt cac aga ggg aac tgt gaa gga      720
Leu Leu Leu Leu Glu Gln Cys Tyr Phe His Arg Gly Asn Cys Glu Gly
225                 230                 235                 240

gac aaa tca aag tgc aat aaa cct aat aat aaa gac tgc aaa gaa tat      768
Asp Lys Ser Lys Cys Asn Lys Pro Asn Asn Lys Asp Cys Lys Glu Tyr
                245                 250                 255

gta cca gag tgt gat gaa tta gca gaa aag tgt gga aaa gaa aat att      816
Val Pro Glu Cys Asp Glu Leu Ala Glu Lys Cys Gly Lys Glu Asn Ile
            260                 265                 270

gtt tat atg cat cca gga tcc gat ttc gat cca act aag cca gag cct      864
Val Tyr Met His Pro Gly Ser Asp Phe Asp Pro Thr Lys Pro Glu Pro
        275                 280                 285

aca cta gca gag gac ata ggg ctg gaa gag ctt tat aag agg gca gaa      912
Thr Leu Ala Glu Asp Ile Gly Leu Glu Glu Leu Tyr Lys Arg Ala Glu
    290                 295                 300

gag gat gga att ttt gtt gga aga caa cat gta aga gat gca aca gct      960
Glu Asp Gly Ile Phe Val Gly Arg Gln His Val Arg Asp Ala Thr Ala
305                 310                 315                 320

ttg ttg gca cta ctt ctt aag aaa acc ctt aaa aaa gaa gaa tgt ata     1008
Leu Leu Ala Leu Leu Leu Lys Lys Thr Leu Lys Lys Glu Glu Cys Ile
                325                 330                 335

aaa gcc ctt aaa aaa aac tgc gaa aac cct cat gaa cat gag gcc tta     1056
```

-continued

```
Lys Ala Leu Lys Lys Asn Cys Glu Asn Pro His Glu His Glu Ala Leu
            340                 345                 350

gaa aat cta tgt aag gaa aat aaa cca agt agt gat gga acg aaa aaa      1104
Glu Asn Leu Cys Lys Glu Asn Lys Pro Ser Ser Asp Gly Thr Lys Lys
        355                 360                 365

tgt gat gaa cta gaa aaa gat gtt aac aaa act tgt aca agt ctt aca      1152
Cys Asp Glu Leu Glu Lys Asp Val Asn Lys Thr Cys Thr Ser Leu Thr
    370                 375                 380

tca aca att ctt aaa aac cgt ctt tac att tca cct gat gga att gcg      1200
Ser Thr Ile Leu Lys Asn Arg Leu Tyr Ile Ser Pro Asp Gly Ile Ala
385                 390                 395                 400

gaa tgg gga aaa tta ccg aca ttt ctt agt gat gaa gat tgt gca aaa      1248
Glu Trp Gly Lys Leu Pro Thr Phe Leu Ser Asp Glu Asp Cys Ala Lys
                405                 410                 415

cta gaa tct tat tgc ttt tat tat aaa gaa act tgt cca gat gtc aaa      1296
Leu Glu Ser Tyr Cys Phe Tyr Tyr Lys Glu Thr Cys Pro Asp Val Lys
            420                 425                 430

gaa gct tgt atg aat gtg agg gca gcg tgt tat aag aga ggg ctt gat      1344
Glu Ala Cys Met Asn Val Arg Ala Ala Cys Tyr Lys Arg Gly Leu Asp
        435                 440                 445

gca cgg gca aac agt gtg ttg caa aaa aat atg cga ggg tta ttg cat      1392
Ala Arg Ala Asn Ser Val Leu Gln Lys Asn Met Arg Gly Leu Leu His
    450                 455                 460

ggc tca aat aaa gat tgg ctt aag aaa ttt caa caa gaa tta gca aaa      1440
Gly Ser Asn Lys Asp Trp Leu Lys Lys Phe Gln Gln Glu Leu Ala Lys
465                 470                 475                 480

gta tgt gag aaa ctg aaa gga aat aaa gga agt ttc tcg aac gat gaa      1488
Val Cys Glu Lys Leu Lys Gly Asn Lys Gly Ser Phe Ser Asn Asp Glu
                485                 490                 495

ttg ttt gtt ctg tgt ata caa cca gca aag gca gca cga tta ctt aca      1536
Leu Phe Val Leu Cys Ile Gln Pro Ala Lys Ala Ala Arg Leu Leu Thr
            500                 505                 510

cat cac cat caa atg aga gtt atc ttt tta cga caa caa ctg gat caa      1584
His His His Gln Met Arg Val Ile Phe Leu Arg Gln Gln Leu Asp Gln
        515                 520                 525

aag aga gat ttt ccg aca gat aaa gac tgc aag gaa tta ggg aga aaa      1632
Lys Arg Asp Phe Pro Thr Asp Lys Asp Cys Lys Glu Leu Gly Arg Lys
    530                 535                 540

tgc caa gat tta gga aag gat tca aaa gaa att aca tgg cca tgt cat      1680
Cys Gln Asp Leu Gly Lys Asp Ser Lys Glu Ile Thr Trp Pro Cys His
545                 550                 555                 560

aca cta gaa cag caa tgc aat cgc tta ggg att aca gaa att tta aaa      1728
Thr Leu Glu Gln Gln Cys Asn Arg Leu Gly Ile Thr Glu Ile Leu Lys
                565                 570                 575

cag att tta ttg gat gaa cac aaa gat act ttg aaa agt cat gaa aac      1776
Gln Ile Leu Leu Asp Glu His Lys Asp Thr Leu Lys Ser His Glu Asn
            580                 585                 590

tgt gca aaa tat tta aaa aga aaa tgc cat aaa tgg tct aga agg ggt      1824
Cys Ala Lys Tyr Leu Lys Arg Lys Cys His Lys Trp Ser Arg Arg Gly
        595                 600                 605

gat gat cgt ttt tct ttt gta tgt gtt ttc caa aac gct aca tgt gag      1872
Asp Asp Arg Phe Ser Phe Val Cys Val Phe Gln Asn Ala Thr Cys Glu
    610                 615                 620

ctg atg gta aaa gac gtg caa gat agg tgc aaa ata ttc gaa gaa aat      1920
Leu Met Val Lys Asp Val Gln Asp Arg Cys Lys Ile Phe Glu Glu Asn
625                 630                 635                 640

atg caa gca tca gat att aat gat tcc ctt aaa aaa aat caa ata aaa      1968
Met Gln Ala Ser Asp Ile Asn Asp Ser Leu Lys Lys Asn Gln Ile Lys
                645                 650                 655
```

-continued

```
gca gaa tca gca gca aat att tgt ccc tca tgg cat cca tac tgc gat     2016
Ala Glu Ser Ala Ala Asn Ile Cys Pro Ser Trp His Pro Tyr Cys Asp
            660                 665                 670

aga ttt tta ccc aat tgt cct gat ctt aag aaa gga aaa act ttc tgt     2064
Arg Phe Leu Pro Asn Cys Pro Asp Leu Lys Lys Gly Lys Thr Phe Cys
        675                 680                 685

caa aat ctt aaa aaa tat tgc gaa cca ttc tac aaa aga aag gtt tta     2112
Gln Asn Leu Lys Lys Tyr Cys Glu Pro Phe Tyr Lys Arg Lys Val Leu
    690                 695                 700

gaa gat gct ctt aaa gta gag ctt cga gga aat tta agt aat ata act     2160
Glu Asp Ala Leu Lys Val Glu Leu Arg Gly Asn Leu Ser Asn Ile Thr
705                 710                 715                 720

aaa tgt gaa cct gca tta gaa aga tat tgt aca gta ttg aaa gac gta     2208
Lys Cys Glu Pro Ala Leu Glu Arg Tyr Cys Thr Val Leu Lys Asp Val
                725                 730                 735

aat aat gcg tca atc agc agt tta tgt aaa gat aat acc gaa agt aaa     2256
Asn Asn Ala Ser Ile Ser Ser Leu Cys Lys Asp Asn Thr Glu Ser Lys
            740                 745                 750

act aaa aag gcc gat aat aaa aat gtt aga aag aag ctt tgt cta aaa     2304
Thr Lys Lys Ala Asp Asn Lys Asn Val Arg Lys Lys Leu Cys Leu Lys
        755                 760                 765

tta gtg gaa gag gtg gaa cag caa tgc aaa gta tta cca aca gaa tta     2352
Leu Val Glu Glu Val Glu Gln Gln Cys Lys Val Leu Pro Thr Glu Leu
    770                 775                 780

aca gag ctg gaa aaa agt cta aaa aaa gat gtt aag aca tat gag gaa     2400
Thr Glu Leu Glu Lys Ser Leu Lys Lys Asp Val Lys Thr Tyr Glu Glu
785                 790                 795                 800

ctt aag gaa agg gca aaa aaa gca atg aac aag tcc agc ctt gtt tta     2448
Leu Lys Glu Arg Ala Lys Lys Ala Met Asn Lys Ser Ser Leu Val Leu
                805                 810                 815

tca ctt gtt aag aaa aac gaa agt aat aca tcg aaa aat aat agc aaa     2496
Ser Leu Val Lys Lys Asn Glu Ser Asn Thr Ser Lys Asn Asn Ser Lys
            820                 825                 830

aac aag gat aag aat gtc gtt tca aac gga ctt caa gat acc aca aaa     2544
Asn Lys Asp Lys Asn Val Val Ser Asn Gly Leu Gln Asp Thr Thr Lys
        835                 840                 845

tat gtg aaa ata cta cga aga gga gtt aag gag gca ctt gta aca gaa     2592
Tyr Val Lys Ile Leu Arg Arg Gly Val Lys Glu Ala Leu Val Thr Glu
    850                 855                 860

tct gaa gcc aag gca ttt gat ttg gca gca gaa gtg ttt gga aga tat     2640
Ser Glu Ala Lys Ala Phe Asp Leu Ala Ala Glu Val Phe Gly Arg Tyr
865                 870                 875                 880

gta gac ttg aaa gaa aaa tgt gag aaa ttg act tcg gat tgc ggg att     2688
Val Asp Leu Lys Glu Lys Cys Glu Lys Leu Thr Ser Asp Cys Gly Ile
                885                 890                 895

aaa gac gat tgc gat ggt tta aaa gaa gtg tgt gga aag att gag aag     2736
Lys Asp Asp Cys Asp Gly Leu Lys Glu Val Cys Gly Lys Ile Glu Lys
            900                 905                 910

aca tgt cac gat ctg aag cct ctg gag gtg aag tcg cat gaa ata gtc     2784
Thr Cys His Asp Leu Lys Pro Leu Glu Val Lys Ser His Glu Ile Val
        915                 920                 925

aca gaa agc aca acg acg acc aca acg aca aca acg acc gtt acc gat     2832
Thr Glu Ser Thr Thr Thr Thr Thr Thr Thr Thr Thr Thr Val Thr Asp
    930                 935                 940

ccg aag gca aca gaa tgc aaa tcc tta cag aca aca gat aca tgg gtt     2880
Pro Lys Ala Thr Glu Cys Lys Ser Leu Gln Thr Thr Asp Thr Trp Val
945                 950                 955                 960

aca cag aca tcg aca cac aca agc acg tct acc atc aca tct acc atc     2928
Thr Gln Thr Ser Thr His Thr Ser Thr Ser Thr Ile Thr Ser Thr Ile
                965                 970                 975
```

-continued

```
aca tca aaa ata aca ttg aca tca acg agg cga tgc aaa cca acc aag     2976
Thr Ser Lys Ile Thr Leu Thr Ser Thr Arg Arg Cys Lys Pro Thr Lys
            980                 985                 990

tgt acg aca ggg gat gaa gca gga gac gtg aaa ccg agt gag gga ttg     3024
Cys Thr Thr Gly Asp Glu Ala Gly Asp Val Lys Pro Ser Glu Gly Leu
        995                1000                1005

aag atg agt ggg tgg agc gtg atg agg ggg gtg ata gta gca atg gtt     3072
Lys Met Ser Gly Trp Ser Val Met Arg Gly Val Ile Val Ala Met Val
   1010                1015                1020

att tcg ttc atg att tag                                             3090
Ile Ser Phe Met Ile
1025               1030


<210> SEQ ID NO 6
<211> LENGTH: 1029
<212> TYPE: PRT
<213> ORGANISM: Pneumocystis carinii sp. f. hominis

<400> SEQUENCE: 6

Met Ala Arg Ala Val Lys Arg Arg Ala Lys Gly Ala Gln Asn Ser Ile
  1               5                  10                  15

Asp Glu Glu His Val Leu Ala Leu Ile Leu Lys Lys Asn Gly Leu Glu
            20                  25                  30

Asp Thr Lys Cys Lys Thr Lys Leu Glu Glu Tyr Cys Lys Thr Leu Thr
        35                  40                  45

Asn Ala Gly Leu Asn Pro Glu Lys Val His Glu Lys Leu Lys Asp Phe
    50                  55                  60

Cys Asp Asn Gly Lys Arg Asn Glu Lys Cys Gln Asp Leu Lys Asn Lys
 65                  70                  75                  80

Val Asn Gln Lys Cys Ile Lys Phe Gln Gly Lys Leu Gln Thr Ala Ala
                85                  90                  95

Gly Lys Lys Ile Ser Glu Leu Thr Asp Glu Asp Cys Lys Lys Asn Glu
            100                 105                 110

Gln Gln Cys Leu Phe Leu Glu Gly Ala Cys Pro Thr Glu Leu Lys Asp
        115                 120                 125

Asp Cys Asn Lys Leu Arg Asn Asn Cys Tyr Gln Lys Glu Arg Asn Asn
    130                 135                 140

Val Ala Glu Glu Val Leu Leu Arg Ala Leu Arg Gly Asp Leu Asn Glu
145                 150                 155                 160

Thr Lys Thr Cys Glu Lys Lys Leu Lys Glu Val Cys Pro Lys Leu Glu
                165                 170                 175

Arg Glu Ser Asp Glu Leu Thr Glu Leu Cys Leu Tyr Gln Lys Thr Thr
            180                 185                 190

Cys Val Ser Leu Val Thr Lys Gly Lys Ser Lys Cys Asp Thr Leu Glu
        195                 200                 205

Lys Glu Val Glu Glu Ala Leu Lys Lys Asn Glu Leu Arg Glu Lys Cys
    210                 215                 220

Leu Leu Leu Leu Glu Gln Cys Tyr Phe His Arg Gly Asn Cys Glu Gly
225                 230                 235                 240

Asp Lys Ser Lys Cys Asn Lys Pro Asn Asn Lys Asp Cys Lys Glu Tyr
                245                 250                 255

Val Pro Glu Cys Asp Glu Leu Ala Glu Lys Cys Gly Lys Glu Asn Ile
            260                 265                 270

Val Tyr Met His Pro Gly Ser Asp Phe Asp Pro Thr Lys Pro Glu Pro
        275                 280                 285
```

-continued

```
Thr Leu Ala Glu Asp Ile Gly Leu Glu Glu Leu Tyr Lys Arg Ala Glu
    290                 295                 300

Glu Asp Gly Ile Phe Val Gly Arg Gln His Val Arg Asp Ala Thr Ala
305                 310                 315                 320

Leu Leu Ala Leu Leu Leu Lys Lys Thr Leu Lys Lys Glu Glu Cys Ile
                325                 330                 335

Lys Ala Leu Lys Lys Asn Cys Glu Asn Pro His Glu His Glu Ala Leu
            340                 345                 350

Glu Asn Leu Cys Lys Glu Asn Lys Pro Ser Ser Asp Gly Thr Lys Lys
        355                 360                 365

Cys Asp Glu Leu Glu Lys Asp Val Asn Lys Thr Cys Thr Ser Leu Thr
    370                 375                 380

Ser Thr Ile Leu Lys Asn Arg Leu Tyr Ile Ser Pro Asp Gly Ile Ala
385                 390                 395                 400

Glu Trp Gly Lys Leu Pro Thr Phe Leu Ser Asp Glu Asp Cys Ala Lys
                405                 410                 415

Leu Glu Ser Tyr Cys Phe Tyr Tyr Lys Glu Thr Cys Pro Asp Val Lys
            420                 425                 430

Glu Ala Cys Met Asn Val Arg Ala Ala Cys Tyr Lys Arg Gly Leu Asp
        435                 440                 445

Ala Arg Ala Asn Ser Val Leu Gln Lys Asn Met Arg Gly Leu Leu His
    450                 455                 460

Gly Ser Asn Lys Asp Trp Leu Lys Lys Phe Gln Gln Glu Leu Ala Lys
465                 470                 475                 480

Val Cys Glu Lys Leu Lys Gly Asn Lys Gly Ser Phe Ser Asn Asp Glu
                485                 490                 495

Leu Phe Val Leu Cys Ile Gln Pro Ala Lys Ala Ala Arg Leu Leu Thr
            500                 505                 510

His His His Gln Met Arg Val Ile Phe Leu Arg Gln Gln Leu Asp Gln
        515                 520                 525

Lys Arg Asp Phe Pro Thr Asp Lys Asp Cys Lys Glu Leu Gly Arg Lys
    530                 535                 540

Cys Gln Asp Leu Gly Lys Asp Ser Lys Glu Ile Thr Trp Pro Cys His
545                 550                 555                 560

Thr Leu Glu Gln Gln Cys Asn Arg Leu Gly Ile Thr Glu Ile Leu Lys
                565                 570                 575

Gln Ile Leu Leu Asp Glu His Lys Asp Thr Leu Lys Ser His Glu Asn
            580                 585                 590

Cys Ala Lys Tyr Leu Lys Arg Lys Cys His Lys Trp Ser Arg Arg Gly
        595                 600                 605

Asp Asp Arg Phe Ser Phe Val Cys Val Phe Gln Asn Ala Thr Cys Glu
    610                 615                 620

Leu Met Val Lys Asp Val Gln Asp Arg Cys Lys Ile Phe Glu Glu Asn
625                 630                 635                 640

Met Gln Ala Ser Asp Ile Asn Asp Ser Leu Lys Lys Asn Gln Ile Lys
                645                 650                 655

Ala Glu Ser Ala Ala Asn Ile Cys Pro Ser Trp His Pro Tyr Cys Asp
            660                 665                 670

Arg Phe Leu Pro Asn Cys Pro Asp Leu Lys Lys Gly Lys Thr Phe Cys
        675                 680                 685

Gln Asn Leu Lys Lys Tyr Cys Glu Pro Phe Tyr Lys Arg Lys Val Leu
    690                 695                 700

Glu Asp Ala Leu Lys Val Glu Leu Arg Gly Asn Leu Ser Asn Ile Thr
```

-continued

```
705                 710                 715                 720

Lys Cys Glu Pro Ala Leu Glu Arg Tyr Cys Thr Val Leu Lys Asp Val
                725                 730                 735

Asn Asn Ala Ser Ile Ser Ser Leu Cys Lys Asp Asn Thr Glu Ser Lys
            740                 745                 750

Thr Lys Lys Ala Asp Asn Lys Asn Val Arg Lys Lys Leu Cys Leu Lys
        755                 760                 765

Leu Val Glu Glu Val Glu Gln Gln Cys Lys Val Leu Pro Thr Glu Leu
    770                 775                 780

Thr Glu Leu Glu Lys Ser Leu Lys Lys Asp Val Lys Thr Tyr Glu Glu
785                 790                 795                 800

Leu Lys Glu Arg Ala Lys Lys Ala Met Asn Lys Ser Ser Leu Val Leu
                805                 810                 815

Ser Leu Val Lys Lys Asn Glu Ser Asn Thr Ser Lys Asn Asn Ser Lys
            820                 825                 830

Asn Lys Asp Lys Asn Val Val Ser Asn Gly Leu Gln Asp Thr Thr Lys
        835                 840                 845

Tyr Val Lys Ile Leu Arg Arg Gly Val Lys Glu Ala Leu Val Thr Glu
    850                 855                 860

Ser Glu Ala Lys Ala Phe Asp Leu Ala Ala Glu Val Phe Gly Arg Tyr
865                 870                 875                 880

Val Asp Leu Lys Glu Lys Cys Glu Lys Leu Thr Ser Asp Cys Gly Ile
                885                 890                 895

Lys Asp Asp Cys Asp Gly Leu Lys Glu Val Cys Gly Lys Ile Glu Lys
            900                 905                 910

Thr Cys His Asp Leu Lys Pro Leu Glu Val Lys Ser His Glu Ile Val
        915                 920                 925

Thr Glu Ser Thr Thr Thr Thr Thr Thr Thr Thr Thr Thr Val Thr Asp
    930                 935                 940

Pro Lys Ala Thr Glu Cys Lys Ser Leu Gln Thr Thr Asp Thr Trp Val
945                 950                 955                 960

Thr Gln Thr Ser Thr His Thr Ser Thr Ser Thr Ile Thr Ser Thr Ile
                965                 970                 975

Thr Ser Lys Ile Thr Leu Thr Ser Thr Arg Arg Cys Lys Pro Thr Lys
            980                 985                 990

Cys Thr Thr Gly Asp Glu Ala Gly Asp Val Lys Pro Ser Glu Gly Leu
        995                1000                1005

Lys Met Ser Gly Trp Ser Val Met Arg Gly Val Ile Val Ala Met Val
   1010                1015                1020

Ile Ser Phe Met Ile
1025


<210> SEQ ID NO 7
<211> LENGTH: 3084
<212> TYPE: DNA
<213> ORGANISM: Pneumocystis carinii sp. f. hominis
<220> FEATURE:
<221> NAME/KEY: CDS
<222> LOCATION: (1)..(3084)

<400> SEQUENCE: 7

atg gcg cgg gcg gtc aag cgg cag gca aaa ggt gca cag aat agc att       48
Met Ala Arg Ala Val Lys Arg Gln Ala Lys Gly Ala Gln Asn Ser Ile
  1               5                  10                  15

gat gag gag cat gtt tta gct ttg att tta aaa aaa aat gga tta gaa       96
Asp Glu Glu His Val Leu Ala Leu Ile Leu Lys Lys Asn Gly Leu Glu
```

-continued

```
            20                  25                  30

gat aca aaa tgc aaa act aag ttg gaa gaa tat tgc aaa aca tta aca      144
Asp Thr Lys Cys Lys Thr Lys Leu Glu Glu Tyr Cys Lys Thr Leu Thr
        35                  40                  45

aat gca gga tta aat cca gaa aaa gtt cac gaa aaa tta aaa gat ttc      192
Asn Ala Gly Leu Asn Pro Glu Lys Val His Glu Lys Leu Lys Asp Phe
    50                  55                  60

tgt gat aac ggg aaa cga aat gaa aaa tgt caa gat cta aaa aac aaa      240
Cys Asp Asn Gly Lys Arg Asn Glu Lys Cys Gln Asp Leu Lys Asn Lys
65                  70                  75                  80

gtc aat caa aaa tgc att aaa ttt caa gga aaa ctt caa aca gct gct      288
Val Asn Gln Lys Cys Ile Lys Phe Gln Gly Lys Leu Gln Thr Ala Ala
                85                  90                  95

aga aaa aaa att tca gaa tta aca gat gag gat tgc aaa aag aat gaa      336
Arg Lys Lys Ile Ser Glu Leu Thr Asp Glu Asp Cys Lys Lys Asn Glu
            100                 105                 110

caa caa tgc cta ttt ttg gag gga gca tgt cca aca gaa ctt aaa gat      384
Gln Gln Cys Leu Phe Leu Glu Gly Ala Cys Pro Thr Glu Leu Lys Asp
        115                 120                 125

gac tgc aat aaa tta agg aat aac tgt tat caa aaa gaa cgg aac aat      432
Asp Cys Asn Lys Leu Arg Asn Asn Cys Tyr Gln Lys Glu Arg Asn Asn
    130                 135                 140

gtg gca gaa gaa gtt ctt ttg agg gcg ctt cgt ggt gat ctc aat gaa      480
Val Ala Glu Glu Val Leu Leu Arg Ala Leu Arg Gly Asp Leu Asn Glu
145                 150                 155                 160

aca aag aca tgt gaa aaa aaa ctg aaa gaa gtt tgc ccg aaa tta gaa      528
Thr Lys Thr Cys Glu Lys Lys Leu Lys Glu Val Cys Pro Lys Leu Glu
                165                 170                 175

aga gaa agc gat gaa tta acg gag ctt tgt ctt tat caa aaa aca aca      576
Arg Glu Ser Asp Glu Leu Thr Glu Leu Cys Leu Tyr Gln Lys Thr Thr
            180                 185                 190

tgc gta agt ctt gta aca aaa gga aaa agt aaa tgt gat act ctt gaa      624
Cys Val Ser Leu Val Thr Lys Gly Lys Ser Lys Cys Asp Thr Leu Glu
        195                 200                 205

aaa gaa gtt gaa gaa gca ctt aag aag aat gaa ttg cga gaa aaa tgt      672
Lys Glu Val Glu Glu Ala Leu Lys Lys Asn Glu Leu Arg Glu Lys Cys
    210                 215                 220

cta cta tta ctt gag caa tgt tac ttt cac aga ggg aac tgt gaa gga      720
Leu Leu Leu Leu Glu Gln Cys Tyr Phe His Arg Gly Asn Cys Glu Gly
225                 230                 235                 240

gac aaa tca aag tgc aat aaa cct aat aat aaa gac tgc aaa gaa tat      768
Asp Lys Ser Lys Cys Asn Lys Pro Asn Asn Lys Asp Cys Lys Glu Tyr
                245                 250                 255

gta cca gag tgt gat gaa tta gca gaa aag tgt gga aaa gaa aat att      816
Val Pro Glu Cys Asp Glu Leu Ala Glu Lys Cys Gly Lys Glu Asn Ile
            260                 265                 270

gtt tat atg cat cca gga tcc gat ttc gat cca act aag cca gag cct      864
Val Tyr Met His Pro Gly Ser Asp Phe Asp Pro Thr Lys Pro Glu Pro
        275                 280                 285

aca cta gca gag gac ata ggg ctg gaa gag ctt tat aag agg gca gaa      912
Thr Leu Ala Glu Asp Ile Gly Leu Glu Glu Leu Tyr Lys Arg Ala Glu
    290                 295                 300

gag gat gga att ttt gtt gga aga caa cat gta aga gat gca aca gct      960
Glu Asp Gly Ile Phe Val Gly Arg Gln His Val Arg Asp Ala Thr Ala
305                 310                 315                 320

ttg ttg gca cta ctt ctt aag aaa acc ctt aaa aaa gaa gaa tgt ata     1008
Leu Leu Ala Leu Leu Leu Lys Lys Thr Leu Lys Lys Glu Glu Cys Ile
                325                 330                 335

aaa gcc ctt aaa aaa aac tgc gaa aac cct cat gaa cat gag gcc tta     1056
```

-continued

```
Lys Ala Leu Lys Lys Asn Cys Glu Asn Pro His Glu His Glu Ala Leu
            340                 345                 350

gaa aat cta tgt aag gaa aat aaa cca agt agt gat gga acg aaa aaa      1104
Glu Asn Leu Cys Lys Glu Asn Lys Pro Ser Ser Asp Gly Thr Lys Lys
        355                 360                 365

tgt gat gaa cta gaa aaa gat gtt aac aaa act tgt aca agt ctt aca      1152
Cys Asp Glu Leu Glu Lys Asp Val Asn Lys Thr Cys Thr Ser Leu Thr
    370                 375                 380

tca aca att ctt aaa aac cgt ctt tac att tca cct gat gga att gcg      1200
Ser Thr Ile Leu Lys Asn Arg Leu Tyr Ile Ser Pro Asp Gly Ile Ala
385                 390                 395                 400

gaa tgg gga aaa tta ccg aca ttt ctt agt gat gaa gat tgt gca aaa      1248
Glu Trp Gly Lys Leu Pro Thr Phe Leu Ser Asp Glu Asp Cys Ala Lys
                405                 410                 415

cta gaa tct tat tgc ttt tat tat aaa gaa act tgt cca gat gtc aaa      1296
Leu Glu Ser Tyr Cys Phe Tyr Tyr Lys Glu Thr Cys Pro Asp Val Lys
            420                 425                 430

gaa gct tgt atg aat gtg agg gca gcg tgt tac aag aga ggg ctt gat      1344
Glu Ala Cys Met Asn Val Arg Ala Ala Cys Tyr Lys Arg Gly Leu Asp
        435                 440                 445

gca cgg gca aac agt gtg ttg caa aaa aat atg cgt ggg tta tta cgt      1392
Ala Arg Ala Asn Ser Val Leu Gln Lys Asn Met Arg Gly Leu Leu Arg
    450                 455                 460

ggt tca aat caa agt tgg ctt aag gag ttt caa caa aga tta gta aaa      1440
Gly Ser Asn Gln Ser Trp Leu Lys Glu Phe Gln Gln Arg Leu Val Lys
465                 470                 475                 480

gta tgt aag gag cta aaa gaa aat aaa gga agt ttc cca aac gat gaa      1488
Val Cys Lys Glu Leu Lys Glu Asn Lys Gly Ser Phe Pro Asn Asp Glu
                485                 490                 495

ata ttt gtt ctg tgt gta cag cca gca aaa gct gca cga tta ctt aca      1536
Ile Phe Val Leu Cys Val Gln Pro Ala Lys Ala Ala Arg Leu Leu Thr
            500                 505                 510

cac gat cat caa atg agg gtt acc ttt tta cga caa caa ttg gat caa      1584
His Asp His Gln Met Arg Val Thr Phe Leu Arg Gln Gln Leu Asp Gln
        515                 520                 525

aag aga gat ttt ccg aca gat aaa gac tgc aag gaa cta ggg aaa aaa      1632
Lys Arg Asp Phe Pro Thr Asp Lys Asp Cys Lys Glu Leu Gly Lys Lys
    530                 535                 540

tgc caa gat tta gga aag gat tca aaa gaa att aca tgg cca tgt cat      1680
Cys Gln Asp Leu Gly Lys Asp Ser Lys Glu Ile Thr Trp Pro Cys His
545                 550                 555                 560

aca ctg gag cag caa tgc aat cgc ttg ggg act aca gaa att tta aag      1728
Thr Leu Glu Gln Gln Cys Asn Arg Leu Gly Thr Thr Glu Ile Leu Lys
                565                 570                 575

cag gtt tta ttg gat gaa cac aaa gat act ttg aaa gac caa gaa agt      1776
Gln Val Leu Leu Asp Glu His Lys Asp Thr Leu Lys Asp Gln Glu Ser
            580                 585                 590

tgt gta aaa tac cta aaa gaa aag tgt aat aaa tgg tct aga aga gga      1824
Cys Val Lys Tyr Leu Lys Glu Lys Cys Asn Lys Trp Ser Arg Arg Gly
        595                 600                 605

gat gac cgt ttc tct ttt gta tgt gtt ttc caa aac gct acg tgt gag      1872
Asp Asp Arg Phe Ser Phe Val Cys Val Phe Gln Asn Ala Thr Cys Glu
    610                 615                 620

ctg atg gta aaa gac gtg aaa gac agg tgt gaa gta ttc aaa aaa aat      1920
Leu Met Val Lys Asp Val Lys Asp Arg Cys Glu Val Phe Lys Lys Asn
625                 630                 635                 640

ata aaa gct tca tat att att gaa ttt ctt gaa aat aat aca aat aaa      1968
Ile Lys Ala Ser Tyr Ile Ile Glu Phe Leu Glu Asn Asn Thr Asn Lys
                645                 650                 655
```

-continued ata aca aca ctg gaa aga aat tgt ccc tct tgg cat acg tat tgc aat 2016
Ile Thr Thr Leu Glu Arg Asn Cys Pro Ser Trp His Thr Tyr Cys Asn
660 665 670 aga ttt tca cct aat tgt cca ggc ctt acg aaa gag aat agt tgt aca 2064
Arg Phe Ser Pro Asn Cys Pro Gly Leu Thr Lys Glu Asn Ser Cys Thr
675 680 685 aaa atc aag aag cat tgt gag ccg ttc tat aaa aga aag gcc ttg gaa 2112
Lys Ile Lys Lys His Cys Glu Pro Phe Tyr Lys Arg Lys Ala Leu Glu
690 695 700 gat gct ctc aaa gta gag ctt caa gga aaa ttg act gat aaa tct aaa 2160
Asp Ala Leu Lys Val Glu Leu Gln Gly Lys Leu Thr Asp Lys Ser Lys
705 710 715 720 tgt gaa cct gca ttg aac aga tat tgt aca gta gcg gga aac gta aat 2208
Cys Glu Pro Ala Leu Asn Arg Tyr Cys Thr Val Ala Gly Asn Val Asn
725 730 735 aat gcg tca atc agt ggc tta tgc aaa gct aac acc aag gat aac tct 2256
Asn Ala Ser Ile Ser Gly Leu Cys Lys Ala Asn Thr Lys Asp Asn Ser
740 745 750 gga aag agt gat gag gat gct aga aag gaa ctc tgt gag aaa tca gtg 2304
Gly Lys Ser Asp Glu Asp Ala Arg Lys Glu Leu Cys Glu Lys Ser Val
755 760 765 aaa gaa gtg gaa gaa cag tgc aaa gca tta cca aca gaa tta gga caa 2352
Lys Glu Val Glu Glu Gln Cys Lys Ala Leu Pro Thr Glu Leu Gly Gln
770 775 780 ccg gca gct gat cta aaa aaa gat tat aag aca tat gag gaa ctt aag 2400
Pro Ala Ala Asp Leu Lys Lys Asp Tyr Lys Thr Tyr Glu Glu Leu Lys
785 790 795 800 aaa cgt gca gag gaa gca atg aac aag tcc agt ctt gtt ttg tca ctc 2448
Lys Arg Ala Glu Glu Ala Met Asn Lys Ser Ser Leu Val Leu Ser Leu
805 810 815 att aag aaa aac gaa agt aat gta tca aaa agt aat agc aaa aac aag 2496
Ile Lys Lys Asn Glu Ser Asn Val Ser Lys Ser Asn Ser Lys Asn Lys
820 825 830 gat aag aat gcc gtt tca aac gga ctt caa gat acc aca aaa cat gtg 2544
Asp Lys Asn Ala Val Ser Asn Gly Leu Gln Asp Thr Thr Lys His Val
835 840 845 aaa ata cta cgg aga gga gtt aag gat gta tcc gta aca gaa tta gaa 2592
Lys Ile Leu Arg Arg Gly Val Lys Asp Val Ser Val Thr Glu Leu Glu
850 855 860 gct aaa gca ttt gat ttg gca gca gaa gta ttt gga aga tat gta gat 2640
Ala Lys Ala Phe Asp Leu Ala Ala Glu Val Phe Gly Arg Tyr Val Asp
865 870 875 880 ttg aag gaa aga tgt aat aaa ttg gaa tca gat tgc aga att aag gag 2688
Leu Lys Glu Arg Cys Asn Lys Leu Glu Ser Asp Cys Arg Ile Lys Glu
885 890 895 gat tgc aaa gac tta gaa gaa gta tgc aaa aag att aat aag gct tgt 2736
Asp Cys Lys Asp Leu Glu Glu Val Cys Lys Lys Ile Asn Lys Ala Cys
900 905 910 cgc aat ctg aag cct ctg gag gtg aag ccg cac gaa aca gtg aca gaa 2784
Arg Asn Leu Lys Pro Leu Glu Val Lys Pro His Glu Thr Val Thr Glu
915 920 925 ggt aca acg aca act aca aca aca aca aca acc gtt gcc gat ccg aag 2832
Gly Thr Thr Thr Thr Thr Thr Thr Thr Thr Thr Val Ala Asp Pro Lys
930 935 940 gca acg gaa tgc aaa tcc tta cag aca aca gac aca tgg gtt aca cag 2880
Ala Thr Glu Cys Lys Ser Leu Gln Thr Thr Asp Thr Trp Val Thr Gln
945 950 955 960 aca tcg aca cac aca agc acg tct act atc aca tct acc atc aca tca 2928
Thr Ser Thr His Thr Ser Thr Ser Thr Ile Thr Ser Thr Ile Thr Ser
965 970 975

-continued

```
aaa ata aca ttg aca tca acg agg cga tgc aaa cca acc aag tgt acg     2976
Lys Ile Thr Leu Thr Ser Thr Arg Arg Cys Lys Pro Thr Lys Cys Thr
            980                 985                 990

aca ggg gat gat gca gaa gac gtg aag cca agt gaa ggc ttg agg gtg     3024
Thr Gly Asp Asp Ala Glu Asp Val Lys Pro Ser Glu Gly Leu Arg Val
        995                1000                1005

agc ggg tgg aat gtg atg agg ggg gtg ata gta gca atg gtt att tcg     3072
Ser Gly Trp Asn Val Met Arg Gly Val Ile Val Ala Met Val Ile Ser
   1010                1015                1020

ttc atg att tag                                                     3084
Phe Met Ile
1025
```

<210> SEQ ID NO 8
<211> LENGTH: 1027
<212> TYPE: PRT
<213> ORGANISM: Pneumocystis carinii sp. f. hominis

<400> SEQUENCE: 8

```
Met Ala Arg Ala Val Lys Arg Gln Ala Lys Gly Ala Gln Asn Ser Ile
  1               5                  10                  15

Asp Glu Glu His Val Leu Ala Leu Ile Leu Lys Lys Asn Gly Leu Glu
             20                  25                  30

Asp Thr Lys Cys Lys Thr Lys Leu Glu Glu Tyr Cys Lys Thr Leu Thr
        35                  40                  45

Asn Ala Gly Leu Asn Pro Glu Lys Val His Glu Lys Leu Lys Asp Phe
    50                  55                  60

Cys Asp Asn Gly Lys Arg Asn Glu Lys Cys Gln Asp Leu Lys Asn Lys
 65                  70                  75                  80

Val Asn Gln Lys Cys Ile Lys Phe Gln Gly Lys Leu Gln Thr Ala Ala
                 85                  90                  95

Arg Lys Lys Ile Ser Glu Leu Thr Asp Glu Asp Cys Lys Lys Asn Glu
            100                 105                 110

Gln Gln Cys Leu Phe Leu Glu Gly Ala Cys Pro Thr Glu Leu Lys Asp
        115                 120                 125

Asp Cys Asn Lys Leu Arg Asn Asn Cys Tyr Gln Lys Glu Arg Asn Asn
    130                 135                 140

Val Ala Glu Glu Val Leu Leu Arg Ala Leu Arg Gly Asp Leu Asn Glu
145                 150                 155                 160

Thr Lys Thr Cys Glu Lys Lys Leu Lys Glu Val Cys Pro Lys Leu Glu
                165                 170                 175

Arg Glu Ser Asp Glu Leu Thr Glu Leu Cys Leu Tyr Gln Lys Thr Thr
            180                 185                 190

Cys Val Ser Leu Val Thr Lys Gly Lys Ser Lys Cys Asp Thr Leu Glu
        195                 200                 205

Lys Glu Val Glu Glu Ala Leu Lys Lys Asn Glu Leu Arg Glu Lys Cys
    210                 215                 220

Leu Leu Leu Leu Glu Gln Cys Tyr Phe His Arg Gly Asn Cys Glu Gly
225                 230                 235                 240

Asp Lys Ser Lys Cys Asn Lys Pro Asn Asn Lys Asp Cys Lys Glu Tyr
                245                 250                 255

Val Pro Glu Cys Asp Glu Leu Ala Glu Lys Cys Gly Lys Glu Asn Ile
            260                 265                 270

Val Tyr Met His Pro Gly Ser Asp Phe Asp Pro Thr Lys Pro Glu Pro
        275                 280                 285
```

-continued

```
Thr Leu Ala Glu Asp Ile Gly Leu Glu Glu Leu Tyr Lys Arg Ala Glu
    290                 295                 300

Glu Asp Gly Ile Phe Val Gly Arg Gln His Val Arg Asp Ala Thr Ala
305                 310                 315                 320

Leu Leu Ala Leu Leu Leu Lys Lys Thr Leu Lys Lys Glu Glu Cys Ile
                325                 330                 335

Lys Ala Leu Lys Lys Asn Cys Glu Asn Pro His Glu His Glu Ala Leu
            340                 345                 350

Glu Asn Leu Cys Lys Glu Asn Lys Pro Ser Ser Asp Gly Thr Lys Lys
        355                 360                 365

Cys Asp Glu Leu Glu Lys Asp Val Asn Lys Thr Cys Thr Ser Leu Thr
    370                 375                 380

Ser Thr Ile Leu Lys Asn Arg Leu Tyr Ile Ser Pro Asp Gly Ile Ala
385                 390                 395                 400

Glu Trp Gly Lys Leu Pro Thr Phe Leu Ser Asp Glu Asp Cys Ala Lys
                405                 410                 415

Leu Glu Ser Tyr Cys Phe Tyr Tyr Lys Glu Thr Cys Pro Asp Val Lys
            420                 425                 430

Glu Ala Cys Met Asn Val Arg Ala Ala Cys Tyr Lys Arg Gly Leu Asp
        435                 440                 445

Ala Arg Ala Asn Ser Val Leu Gln Lys Asn Met Arg Gly Leu Leu Arg
    450                 455                 460

Gly Ser Asn Gln Ser Trp Leu Lys Glu Phe Gln Gln Arg Leu Val Lys
465                 470                 475                 480

Val Cys Lys Glu Leu Lys Glu Asn Lys Gly Ser Phe Pro Asn Asp Glu
                485                 490                 495

Ile Phe Val Leu Cys Val Gln Pro Ala Lys Ala Ala Arg Leu Leu Thr
            500                 505                 510

His Asp His Gln Met Arg Val Thr Phe Leu Arg Gln Gln Leu Asp Gln
        515                 520                 525

Lys Arg Asp Phe Pro Thr Asp Lys Asp Cys Lys Glu Leu Gly Lys Lys
    530                 535                 540

Cys Gln Asp Leu Gly Lys Asp Ser Lys Glu Ile Thr Trp Pro Cys His
545                 550                 555                 560

Thr Leu Glu Gln Gln Cys Asn Arg Leu Gly Thr Thr Glu Ile Leu Lys
                565                 570                 575

Gln Val Leu Leu Asp Glu His Lys Asp Thr Leu Lys Asp Gln Glu Ser
            580                 585                 590

Cys Val Lys Tyr Leu Lys Glu Lys Cys Asn Lys Trp Ser Arg Arg Gly
        595                 600                 605

Asp Asp Arg Phe Ser Phe Val Cys Val Phe Gln Asn Ala Thr Cys Glu
    610                 615                 620

Leu Met Val Lys Asp Val Lys Asp Arg Cys Glu Val Phe Lys Lys Asn
625                 630                 635                 640

Ile Lys Ala Ser Tyr Ile Ile Glu Phe Leu Glu Asn Asn Thr Asn Lys
                645                 650                 655

Ile Thr Thr Leu Glu Arg Asn Cys Pro Ser Trp His Thr Tyr Cys Asn
            660                 665                 670

Arg Phe Ser Pro Asn Cys Pro Gly Leu Thr Lys Glu Asn Ser Cys Thr
        675                 680                 685

Lys Ile Lys Lys His Cys Glu Pro Phe Tyr Lys Arg Lys Ala Leu Glu
    690                 695                 700

Asp Ala Leu Lys Val Glu Leu Gln Gly Lys Leu Thr Asp Lys Ser Lys
```

-continued

```
705                 710                 715                 720

Cys Glu Pro Ala Leu Asn Arg Tyr Cys Thr Val Ala Gly Asn Val Asn
                725                 730                 735

Asn Ala Ser Ile Ser Gly Leu Cys Lys Ala Asn Thr Lys Asp Asn Ser
            740                 745                 750

Gly Lys Ser Asp Glu Asp Ala Arg Lys Glu Leu Cys Glu Lys Ser Val
        755                 760                 765

Lys Glu Val Glu Glu Gln Cys Lys Ala Leu Pro Thr Glu Leu Gly Gln
    770                 775                 780

Pro Ala Ala Asp Leu Lys Lys Asp Tyr Lys Thr Tyr Glu Glu Leu Lys
785                 790                 795                 800

Lys Arg Ala Glu Glu Ala Met Asn Lys Ser Ser Leu Val Leu Ser Leu
                805                 810                 815

Ile Lys Lys Asn Glu Ser Asn Val Ser Lys Ser Asn Ser Lys Asn Lys
            820                 825                 830

Asp Lys Asn Ala Val Ser Asn Gly Leu Gln Asp Thr Thr Lys His Val
        835                 840                 845

Lys Ile Leu Arg Arg Gly Val Lys Asp Val Ser Val Thr Glu Leu Glu
    850                 855                 860

Ala Lys Ala Phe Asp Leu Ala Ala Glu Val Phe Gly Arg Tyr Val Asp
865                 870                 875                 880

Leu Lys Glu Arg Cys Asn Lys Leu Glu Ser Asp Cys Arg Ile Lys Glu
                885                 890                 895

Asp Cys Lys Asp Leu Glu Glu Val Cys Lys Lys Ile Asn Lys Ala Cys
            900                 905                 910

Arg Asn Leu Lys Pro Leu Glu Val Lys Pro His Glu Thr Val Thr Glu
        915                 920                 925

Gly Thr Thr Thr Thr Thr Thr Thr Thr Thr Thr Val Ala Asp Pro Lys
    930                 935                 940

Ala Thr Glu Cys Lys Ser Leu Gln Thr Thr Asp Thr Trp Val Thr Gln
945                 950                 955                 960

Thr Ser Thr His Thr Ser Thr Ser Thr Ile Thr Ser Thr Ile Thr Ser
                965                 970                 975

Lys Ile Thr Leu Thr Ser Thr Arg Arg Cys Lys Pro Thr Lys Cys Thr
            980                 985                 990

Thr Gly Asp Asp Ala Glu Asp Val Lys Pro Ser Glu Gly Leu Arg Val
        995                 1000                1005

Ser Gly Trp Asn Val Met Arg Gly Val Ile Val Ala Met Val Ile Ser
   1010                1015                1020

Phe Met Ile
1025


<210> SEQ ID NO 9
<211> LENGTH: 3081
<212> TYPE: DNA
<213> ORGANISM: Pneumocystis carinii sp. f. hominis
<220> FEATURE:
<221> NAME/KEY: CDS
<222> LOCATION: (1)..(3030)

<400> SEQUENCE: 9

atg gcg cgg gcg gtc aag cgg cag gct gca aaa gca tca ggg gct agt       48
Met Ala Arg Ala Val Lys Arg Gln Ala Ala Lys Ala Ser Gly Ala Ser
  1               5                  10                  15

gta tat gat ggt gaa gaa att ctt ttg gct tta att gca gga aaa aaa       96
Val Tyr Asp Gly Glu Glu Ile Leu Leu Ala Leu Ile Ala Gly Lys Lys
```

-continued

```
                20                  25                  30

tat aat gat aat gaa tgc aaa aaa gaa tta gaa aaa tat tgt aag aca      144
Tyr Asn Asp Asn Glu Cys Lys Lys Glu Leu Glu Lys Tyr Cys Lys Thr
            35                  40                  45

tta acg gat gca gaa tta aaa cca gaa aaa gtt cac aaa aaa ctt aag      192
Leu Thr Asp Ala Glu Leu Lys Pro Glu Lys Val His Lys Lys Leu Lys
        50                  55                  60

gag ttt tgt gaa aat aaa aaa gca gat tca aaa tgc aaa gaa ctg aaa      240
Glu Phe Cys Glu Asn Lys Lys Ala Asp Ser Lys Cys Lys Glu Leu Lys
 65                  70                  75                  80

gaa aaa ctc act caa aaa tgt act gca atc aaa gga aaa ctt aca gaa      288
Glu Lys Leu Thr Gln Lys Cys Thr Ala Ile Lys Gly Lys Leu Thr Glu
                85                  90                  95

gca atc aaa aaa aaa aat tca gat tta acg gat gaa gat tgc aaa gag      336
Ala Ile Lys Lys Lys Asn Ser Asp Leu Thr Asp Glu Asp Cys Lys Glu
            100                 105                 110

aat gaa caa caa tgc cta ttt ttg gag gga gca tgt cca gcg gaa ctt      384
Asn Glu Gln Gln Cys Leu Phe Leu Glu Gly Ala Cys Pro Ala Glu Leu
        115                 120                 125

aaa gat gat tgc aat act ttg aga aat aag tgc tat caa aag aag cgt      432
Lys Asp Asp Cys Asn Thr Leu Arg Asn Lys Cys Tyr Gln Lys Lys Arg
    130                 135                 140

gat aaa gtg gcg gaa gaa gct ctt tta aga gca gtt cgt gga ggt cta      480
Asp Lys Val Ala Glu Glu Ala Leu Leu Arg Ala Val Arg Gly Gly Leu
145                 150                 155                 160

atc aat gaa act aca tgt gaa gga aag ctc aaa gag gtt tgc ata gag      528
Ile Asn Glu Thr Thr Cys Glu Gly Lys Leu Lys Glu Val Cys Ile Glu
                165                 170                 175

ttg agt caa gaa agt gat gag tta acg aag ctt tgt ctt tat caa aaa      576
Leu Ser Gln Glu Ser Asp Glu Leu Thr Lys Leu Cys Leu Tyr Gln Lys
            180                 185                 190

atg acg tgc aaa aca ttt gta tta gaa aaa caa aaa aaa tgt aat gct      624
Met Thr Cys Lys Thr Phe Val Leu Glu Lys Gln Lys Lys Cys Asn Ala
        195                 200                 205

ctt aaa cag gat gtt aac gca gca ctt gag aag aaa gat gag tta cga      672
Leu Lys Gln Asp Val Asn Ala Ala Leu Glu Lys Lys Asp Glu Leu Arg
    210                 215                 220

gga aaa tgt tta cca ctg ctt gaa cga tgc tat ttt tat aga ggg aat      720
Gly Lys Cys Leu Pro Leu Leu Glu Arg Cys Tyr Phe Tyr Arg Gly Asn
225                 230                 235                 240

tgt gaa gat ata tca aaa tgt aat aaa tca tcc gaa gac tgt tat gaa      768
Cys Glu Asp Ile Ser Lys Cys Asn Lys Ser Ser Glu Asp Cys Tyr Glu
                245                 250                 255

tat ttg cca gtg tgt gat aca ttg gca gtg aaa tgt gaa gaa aat aag      816
Tyr Leu Pro Val Cys Asp Thr Leu Ala Val Lys Cys Glu Glu Asn Lys
            260                 265                 270

att att tat aca cat ccg gga tcc gat ttc aat cca act aag tca aag      864
Ile Ile Tyr Thr His Pro Gly Ser Asp Phe Asn Pro Thr Lys Ser Lys
        275                 280                 285

cct act gta gca gaa gac ata gga ctg gaa gag ctt tat aaa aag gcc      912
Pro Thr Val Ala Glu Asp Ile Gly Leu Glu Glu Leu Tyr Lys Lys Ala
    290                 295                 300

gca gaa gaa ggt gtt cat att gga aag cct cct gta aga gat gca act      960
Ala Glu Glu Gly Val His Ile Gly Lys Pro Pro Val Arg Asp Ala Thr
305                 310                 315                 320

gct cta ctg gcg ctt ttg att caa aat cta gat cct aag agt caa gtg     1008
Ala Leu Leu Ala Leu Leu Ile Gln Asn Leu Asp Pro Lys Ser Gln Val
                325                 330                 335

ggt aaa gaa tgc gaa aaa gtt ctt aaa gat aac tgt aaa gag tta aaa     1056
```

-continued

```
Gly Lys Glu Cys Glu Lys Val Leu Lys Asp Asn Cys Lys Glu Leu Lys
            340                 345                 350

agt cat gaa att ttg gga gat ttt tgt aat caa aat gta gct ggt caa      1104
Ser His Glu Ile Leu Gly Asp Phe Cys Asn Gln Asn Val Ala Gly Gln
        355                 360                 365

aat gaa att gaa aag tgt aaa gag tta gag aag gag tta gca aac agt      1152
Asn Glu Ile Glu Lys Cys Lys Glu Leu Glu Lys Glu Leu Ala Asn Ser
    370                 375                 380

act aaa att ctt ttt gaa aaa ata aag aat aaa cac ctc tct gga tcc      1200
Thr Lys Ile Leu Phe Glu Lys Ile Lys Asn Lys His Leu Ser Gly Ser
385                 390                 395                 400

gga gaa gtc att cca tgg tat aag ttg acg aca ttt ctt agt gac aat      1248
Gly Glu Val Ile Pro Trp Tyr Lys Leu Thr Thr Phe Leu Ser Asp Asn
                405                 410                 415

gac tgc aca agg tta gag tca gac tgt ttt tat tta aaa agt caa gca      1296
Asp Cys Thr Arg Leu Glu Ser Asp Cys Phe Tyr Leu Lys Ser Gln Ala
            420                 425                 430

cct ctt gac aaa gaa tgt aat aat ctg aag gca gca tgt tat aag aga      1344
Pro Leu Asp Lys Glu Cys Asn Asn Leu Lys Ala Ala Cys Tyr Lys Arg
        435                 440                 445

ggg ctt gaa gca caa gct aat gaa gca ttg cag aaa aag atg tac gga      1392
Gly Leu Glu Ala Gln Ala Asn Glu Ala Leu Gln Lys Lys Met Tyr Gly
    450                 455                 460

ctg ttc tat ggt tca ggc aaa gaa tgg ttt aag aaa cta cta gaa aaa      1440
Leu Phe Tyr Gly Ser Gly Lys Glu Trp Phe Lys Lys Leu Leu Glu Lys
465                 470                 475                 480

ata atg gaa gaa tgt tcg gaa ctt aaa aca aca agc gat gag ttg ttt      1488
Ile Met Glu Glu Cys Ser Glu Leu Lys Thr Thr Ser Asp Glu Leu Phe
                485                 490                 495

ttg cta tgt att gat cca ctt aaa gca gtc aga ata ctt gca gct gat      1536
Leu Leu Cys Ile Asp Pro Leu Lys Ala Val Arg Ile Leu Ala Ala Asp
            500                 505                 510

atc caa gca aga gca gtc ttt ttg cgg aaa caa ttg gat caa aag cga      1584
Ile Gln Ala Arg Ala Val Phe Leu Arg Lys Gln Leu Asp Gln Lys Arg
        515                 520                 525

gac ttt cca aca gac aaa gat tgc aag gaa tta gga aga aag tgt gaa      1632
Asp Phe Pro Thr Asp Lys Asp Cys Lys Glu Leu Gly Arg Lys Cys Glu
    530                 535                 540

gct tta ggg aag gat tca aat cag att aag tgg cca tgt cat acg cta      1680
Ala Leu Gly Lys Asp Ser Asn Gln Ile Lys Trp Pro Cys His Thr Leu
545                 550                 555                 560

aaa caa cag tgt gat cgc ttg ggg act aca gaa atc ttg aaa cag gtt      1728
Lys Gln Gln Cys Asp Arg Leu Gly Thr Thr Glu Ile Leu Lys Gln Val
                565                 570                 575

tta cta gat gaa cac aag gat act tta aga act cat gaa aac tgt acg      1776
Leu Leu Asp Glu His Lys Asp Thr Leu Arg Thr His Glu Asn Cys Thr
            580                 585                 590

aaa tat tta aag aga aaa tgt cat aaa tgg tct aga agg ggt gat gat      1824
Lys Tyr Leu Lys Arg Lys Cys His Lys Trp Ser Arg Arg Gly Asp Asp
        595                 600                 605

cgt ttc tct ttt gta tgt gtt tac caa aac gct acg tgt aag ctg ata      1872
Arg Phe Ser Phe Val Cys Val Tyr Gln Asn Ala Thr Cys Lys Leu Ile
    610                 615                 620

gta gat gat gtg aaa gac agg tgt gaa gta ttt gaa aaa aat atg caa      1920
Val Asp Asp Val Lys Asp Arg Cys Glu Val Phe Glu Lys Asn Met Gln
625                 630                 635                 640

gcg tca gat att aat aat tct ctt aaa aat aaa caa ata aaa aca gaa      1968
Ala Ser Asp Ile Asn Asn Ser Leu Lys Asn Lys Gln Ile Lys Thr Glu
                645                 650                 655
```

-continued

```
tca gca gca aat att tgt ccc tca tgg cac cca tac tgc gat aga ttt      2016
Ser Ala Ala Asn Ile Cys Pro Ser Trp His Pro Tyr Cys Asp Arg Phe
            660                 665                 670

tta ccc aat tgt cct gat ctt aag aaa gga aaa act ttc tgt caa aat      2064
Leu Pro Asn Cys Pro Asp Leu Lys Lys Gly Lys Thr Phe Cys Gln Asn
        675                 680                 685

ctt aaa aaa tat tgc gaa cca ttc tac aaa agg aag gtt tta gaa gat      2112
Leu Lys Lys Tyr Cys Glu Pro Phe Tyr Lys Arg Lys Val Leu Glu Asp
    690                 695                 700

gct ctt aaa gta gag ctt caa ggg aat tta agt aat aga aat aaa tgt      2160
Ala Leu Lys Val Glu Leu Gln Gly Asn Leu Ser Asn Arg Asn Lys Cys
705                 710                 715                 720

gaa tct gca tta gaa aga tat tgc aca ata ttg aaa aat gta agt gat      2208
Glu Ser Ala Leu Glu Arg Tyr Cys Thr Ile Leu Lys Asn Val Ser Asp
                725                 730                 735

tca tca atc aac agt tta tgt aaa gat aat acc gaa agt aaa act aaa      2256
Ser Ser Ile Asn Ser Leu Cys Lys Asp Asn Thr Glu Ser Lys Thr Lys
            740                 745                 750

aag acc gat aat gaa gtt aga aag aag ctt tgt cta aaa tta gtg gaa      2304
Lys Thr Asp Asn Glu Val Arg Lys Lys Leu Cys Leu Lys Leu Val Glu
        755                 760                 765

gag gtg gaa cag caa tgt aaa atg tta cca gca gaa ttg gag cat gag      2352
Glu Val Glu Gln Gln Cys Lys Met Leu Pro Ala Glu Leu Glu His Glu
    770                 775                 780

gaa aaa gac cta aaa gat gat ttt gaa aca ttt gaa aaa ctt aaa aaa      2400
Glu Lys Asp Leu Lys Asp Asp Phe Glu Thr Phe Glu Lys Leu Lys Lys
785                 790                 795                 800

cag gca gag aaa aca atg aat aaa tcc aat ctt gtt tta tca ttc gtt      2448
Gln Ala Glu Lys Thr Met Asn Lys Ser Asn Leu Val Leu Ser Phe Val
                805                 810                 815

aag aaa gat gaa aat aat aca tcg aaa aat agt agc aaa gac aag gat      2496
Lys Lys Asp Glu Asn Asn Thr Ser Lys Asn Ser Ser Lys Asp Lys Asp
            820                 825                 830

aag aat acc gtt tca aac gga ctt caa gat acc aca gaa cat atg aaa      2544
Lys Asn Thr Val Ser Asn Gly Leu Gln Asp Thr Thr Glu His Met Lys
        835                 840                 845

ata cta cgg aga gga gtt aag gat gta tcc gta aca gaa tct gaa gct      2592
Ile Leu Arg Arg Gly Val Lys Asp Val Ser Val Thr Glu Ser Glu Ala
    850                 855                 860

aag gca ttt gat ttg gta gca gaa gta ttt gga aga tat cta gac ttg      2640
Lys Ala Phe Asp Leu Val Ala Glu Val Phe Gly Arg Tyr Leu Asp Leu
865                 870                 875                 880

aaa gaa aga tgt aat aaa ttg gaa tca gat tgc aga gtt aag gag gat      2688
Lys Glu Arg Cys Asn Lys Leu Glu Ser Asp Cys Arg Val Lys Glu Asp
                885                 890                 895

tgc aag gat tta gaa gga gta tgt gga aag ata caa gga gta tgt tcg      2736
Cys Lys Asp Leu Glu Gly Val Cys Gly Lys Ile Gln Gly Val Cys Ser
            900                 905                 910

aaa tta aaa cca ctg aaa gtg aag ccg cac gaa aca gtg aca gaa agc      2784
Lys Leu Lys Pro Leu Lys Val Lys Pro His Glu Thr Val Thr Glu Ser
        915                 920                 925

aca acg acg acc acg acg aca aca acg acc gtt act gat ccg aag gca      2832
Thr Thr Thr Thr Thr Thr Thr Thr Thr Thr Val Thr Asp Pro Lys Ala
    930                 935                 940

aca gaa tgc aaa tct tta cag aca aca gat aca tgg att aca cag act      2880
Thr Glu Cys Lys Ser Leu Gln Thr Thr Asp Thr Trp Ile Thr Gln Thr
945                 950                 955                 960

tcg aca cat acc agc acg tct acc atc aca tct aca atc aca tca aaa      2928
Ser Thr His Thr Ser Thr Ser Thr Ile Thr Ser Thr Ile Thr Ser Lys
                965                 970                 975
```

-continued

```
ata aca ctc aca tca aca agg cgt tgc aaa cca acc aag tgt acg aca     2976
Ile Thr Leu Thr Ser Thr Arg Arg Cys Lys Pro Thr Lys Cys Thr Thr
            980                 985                 990

ggg gat gat gca gag gac gtg aag ccg agt gag gga ttg aag atg agt     3024
Gly Asp Asp Ala Glu Asp Val Lys Pro Ser Glu Gly Leu Lys Met Ser
        995                1000                1005

ggg tga aacgtgatga gggggtgat agtagcaatg gttatttcgt tcatgattta g    3081
Gly
   1010


<210> SEQ ID NO 10
<211> LENGTH: 1009
<212> TYPE: PRT
<213> ORGANISM: Pneumocystis carinii sp. f. hominis

<400> SEQUENCE: 10

Met Ala Arg Ala Val Lys Arg Gln Ala Ala Lys Ala Ser Gly Ala Ser
  1               5                  10                  15

Val Tyr Asp Gly Glu Glu Ile Leu Leu Ala Leu Ile Ala Gly Lys Lys
             20                  25                  30

Tyr Asn Asp Asn Glu Cys Lys Lys Glu Leu Glu Lys Tyr Cys Lys Thr
         35                  40                  45

Leu Thr Asp Ala Glu Leu Lys Pro Glu Lys Val His Lys Lys Leu Lys
     50                  55                  60

Glu Phe Cys Glu Asn Lys Lys Ala Asp Ser Lys Cys Lys Glu Leu Lys
 65                  70                  75                  80

Glu Lys Leu Thr Gln Lys Cys Thr Ala Ile Lys Gly Lys Leu Thr Glu
                 85                  90                  95

Ala Ile Lys Lys Lys Asn Ser Asp Leu Thr Asp Glu Asp Cys Lys Glu
            100                 105                 110

Asn Glu Gln Gln Cys Leu Phe Leu Glu Gly Ala Cys Pro Ala Glu Leu
        115                 120                 125

Lys Asp Asp Cys Asn Thr Leu Arg Asn Lys Cys Tyr Gln Lys Lys Arg
    130                 135                 140

Asp Lys Val Ala Glu Glu Ala Leu Leu Arg Ala Val Arg Gly Gly Leu
145                 150                 155                 160

Ile Asn Glu Thr Thr Cys Glu Gly Lys Leu Lys Glu Val Cys Ile Glu
                165                 170                 175

Leu Ser Gln Glu Ser Asp Glu Leu Thr Lys Leu Cys Leu Tyr Gln Lys
            180                 185                 190

Met Thr Cys Lys Thr Phe Val Leu Glu Lys Gln Lys Lys Cys Asn Ala
        195                 200                 205

Leu Lys Gln Asp Val Asn Ala Ala Leu Glu Lys Lys Asp Glu Leu Arg
    210                 215                 220

Gly Lys Cys Leu Pro Leu Leu Glu Arg Cys Tyr Phe Tyr Arg Gly Asn
225                 230                 235                 240

Cys Glu Asp Ile Ser Lys Cys Asn Lys Ser Ser Glu Asp Cys Tyr Glu
                245                 250                 255

Tyr Leu Pro Val Cys Asp Thr Leu Ala Val Lys Cys Glu Glu Asn Lys
            260                 265                 270

Ile Ile Tyr Thr His Pro Gly Ser Asp Phe Asn Pro Thr Lys Ser Lys
        275                 280                 285

Pro Thr Val Ala Glu Asp Ile Gly Leu Glu Glu Leu Tyr Lys Lys Ala
    290                 295                 300

Ala Glu Glu Gly Val His Ile Gly Lys Pro Pro Val Arg Asp Ala Thr
```

-continued

```
305                 310                 315                 320

Ala Leu Leu Ala Leu Leu Ile Gln Asn Leu Asp Pro Lys Ser Gln Val
                325                 330                 335

Gly Lys Glu Cys Glu Lys Val Leu Lys Asp Asn Cys Lys Glu Leu Lys
            340                 345                 350

Ser His Glu Ile Leu Gly Asp Phe Cys Asn Gln Asn Val Ala Gly Gln
        355                 360                 365

Asn Glu Ile Glu Lys Cys Lys Glu Leu Glu Lys Glu Leu Ala Asn Ser
    370                 375                 380

Thr Lys Ile Leu Phe Glu Lys Ile Lys Asn Lys His Leu Ser Gly Ser
385                 390                 395                 400

Gly Glu Val Ile Pro Trp Tyr Lys Leu Thr Thr Phe Leu Ser Asp Asn
                405                 410                 415

Asp Cys Thr Arg Leu Glu Ser Asp Cys Phe Tyr Leu Lys Ser Gln Ala
            420                 425                 430

Pro Leu Asp Lys Glu Cys Asn Asn Leu Lys Ala Ala Cys Tyr Lys Arg
        435                 440                 445

Gly Leu Glu Ala Gln Ala Asn Glu Ala Leu Gln Lys Lys Met Tyr Gly
    450                 455                 460

Leu Phe Tyr Gly Ser Gly Lys Glu Trp Phe Lys Lys Leu Leu Glu Lys
465                 470                 475                 480

Ile Met Glu Glu Cys Ser Glu Leu Lys Thr Thr Ser Asp Glu Leu Phe
                485                 490                 495

Leu Leu Cys Ile Asp Pro Leu Lys Ala Val Arg Ile Leu Ala Ala Asp
            500                 505                 510

Ile Gln Ala Arg Ala Val Phe Leu Arg Lys Gln Leu Asp Gln Lys Arg
        515                 520                 525

Asp Phe Pro Thr Asp Lys Asp Cys Lys Glu Leu Gly Arg Lys Cys Glu
    530                 535                 540

Ala Leu Gly Lys Asp Ser Asn Gln Ile Lys Trp Pro Cys His Thr Leu
545                 550                 555                 560

Lys Gln Gln Cys Asp Arg Leu Gly Thr Thr Glu Ile Leu Lys Gln Val
                565                 570                 575

Leu Leu Asp Glu His Lys Asp Thr Leu Arg Thr His Glu Asn Cys Thr
            580                 585                 590

Lys Tyr Leu Lys Arg Lys Cys His Lys Trp Ser Arg Arg Gly Asp Asp
        595                 600                 605

Arg Phe Ser Phe Val Cys Val Tyr Gln Asn Ala Thr Cys Lys Leu Ile
    610                 615                 620

Val Asp Asp Val Lys Asp Arg Cys Glu Val Phe Glu Lys Asn Met Gln
625                 630                 635                 640

Ala Ser Asp Ile Asn Asn Ser Leu Lys Asn Lys Gln Ile Lys Thr Glu
                645                 650                 655

Ser Ala Ala Asn Ile Cys Pro Ser Trp His Pro Tyr Cys Asp Arg Phe
            660                 665                 670

Leu Pro Asn Cys Pro Asp Leu Lys Lys Gly Lys Thr Phe Cys Gln Asn
        675                 680                 685

Leu Lys Lys Tyr Cys Glu Pro Phe Tyr Lys Arg Lys Val Leu Glu Asp
    690                 695                 700

Ala Leu Lys Val Glu Leu Gln Gly Asn Leu Ser Asn Arg Asn Lys Cys
705                 710                 715                 720

Glu Ser Ala Leu Glu Arg Tyr Cys Thr Ile Leu Lys Asn Val Ser Asp
                725                 730                 735
```

-continued

```
Ser Ser Ile Asn Ser Leu Cys Lys Asp Asn Thr Glu Ser Lys Thr Lys
            740                 745                 750

Lys Thr Asp Asn Glu Val Arg Lys Lys Leu Cys Leu Lys Leu Val Glu
        755                 760                 765

Glu Val Glu Gln Gln Cys Lys Met Leu Pro Ala Glu Leu Glu His Glu
    770                 775                 780

Glu Lys Asp Leu Lys Asp Asp Phe Glu Thr Phe Glu Lys Leu Lys Lys
785                 790                 795                 800

Gln Ala Glu Lys Thr Met Asn Lys Ser Asn Leu Val Leu Ser Phe Val
                805                 810                 815

Lys Lys Asp Glu Asn Asn Thr Ser Lys Asn Ser Ser Lys Asp Lys Asp
            820                 825                 830

Lys Asn Thr Val Ser Asn Gly Leu Gln Asp Thr Thr Glu His Met Lys
        835                 840                 845

Ile Leu Arg Arg Gly Val Lys Asp Val Ser Val Thr Glu Ser Glu Ala
    850                 855                 860

Lys Ala Phe Asp Leu Val Ala Glu Val Phe Gly Arg Tyr Leu Asp Leu
865                 870                 875                 880

Lys Glu Arg Cys Asn Lys Leu Glu Ser Asp Cys Arg Val Lys Glu Asp
                885                 890                 895

Cys Lys Asp Leu Glu Gly Val Cys Gly Lys Ile Gln Gly Val Cys Ser
            900                 905                 910

Lys Leu Lys Pro Leu Lys Val Lys Pro His Glu Thr Val Thr Glu Ser
        915                 920                 925

Thr Thr Thr Thr Thr Thr Thr Thr Thr Thr Val Thr Asp Pro Lys Ala
    930                 935                 940

Thr Glu Cys Lys Ser Leu Gln Thr Thr Asp Thr Trp Ile Thr Gln Thr
945                 950                 955                 960

Ser Thr His Thr Ser Thr Ser Thr Ile Thr Ser Thr Ile Thr Ser Lys
                965                 970                 975

Ile Thr Leu Thr Ser Thr Arg Arg Cys Lys Pro Thr Lys Cys Thr Thr
            980                 985                 990

Gly Asp Asp Ala Glu Asp Val Lys Pro Ser Glu Gly Leu Lys Met Ser
        995                 1000                1005

Gly


<210> SEQ ID NO 11
<211> LENGTH: 3054
<212> TYPE: DNA
<213> ORGANISM: Pneumocystis carinii sp. f. hominis
<220> FEATURE:
<221> NAME/KEY: CDS
<222> LOCATION: (1)..(3054)

<400> SEQUENCE: 11

gcg cgg gcg gtc aag cgg cag gta aca gga gca tca ggg caa tat gat       48
Ala Arg Ala Val Lys Arg Gln Val Thr Gly Ala Ser Gly Gln Tyr Asp
  1               5                  10                  15

gat gaa gtg aat att ttg gcg ttg att cta caa gaa gat gca atg gaa       96
Asp Glu Val Asn Ile Leu Ala Leu Ile Leu Gln Glu Asp Ala Met Glu
             20                  25                  30

gat aca aaa tgc aaa aaa agt tta gaa aaa tac tgc gaa gag ttg aaa      144
Asp Thr Lys Cys Lys Lys Ser Leu Glu Lys Tyr Cys Glu Glu Leu Lys
         35                  40                  45

aaa gca tca cta gac atg gaa aaa gta cat aaa atg ctt aaa gat ttc      192
Lys Ala Ser Leu Asp Met Glu Lys Val His Lys Met Leu Lys Asp Phe
```

-continued

```
     50                  55                  60

tgt gga aat ggg aaa gca agt aaa gca aat aca aaa tgt caa ggt cta      240
Cys Gly Asn Gly Lys Ala Ser Lys Ala Asn Thr Lys Cys Gln Gly Leu
 65                  70                  75                  80

caa gcc aaa gtt acg ggg aaa tgt aca aat ttt aaa aca caa aag cta      288
Gln Ala Lys Val Thr Gly Lys Cys Thr Asn Phe Lys Thr Gln Lys Leu
                 85                  90                  95

gga cca gcg tta aca aat cca tca gat gat aat tgc aaa gag agt gaa      336
Gly Pro Ala Leu Thr Asn Pro Ser Asp Asp Asn Cys Lys Glu Ser Glu
            100                 105                 110

cga caa tgc cta ttt ttg gag gga gca tgc cat aat ctt gta gaa gat      384
Arg Gln Cys Leu Phe Leu Glu Gly Ala Cys His Asn Leu Val Glu Asp
        115                 120                 125

tgt aac aaa cta agg aat cta tgt tac cag aaa aaa cgt gac gga gta      432
Cys Asn Lys Leu Arg Asn Leu Cys Tyr Gln Lys Lys Arg Asp Gly Val
    130                 135                 140

gca gaa gaa gtc ctt ttg agg gca ctt cgt agt gat ctc aat aaa aca      480
Ala Glu Glu Val Leu Leu Arg Ala Leu Arg Ser Asp Leu Asn Lys Thr
145                 150                 155                 160

gaa aca cat gaa aaa aaa ctg aaa gag att tgc cca gtc ttg cag agg      528
Glu Thr His Glu Lys Lys Leu Lys Glu Ile Cys Pro Val Leu Gln Arg
                165                 170                 175

gaa agt aat gaa tta acg gac ttg tgt ttg aac cag aaa aag acg tgc      576
Glu Ser Asn Glu Leu Thr Asp Leu Cys Leu Asn Gln Lys Lys Thr Cys
            180                 185                 190

gag aat att ata aaa gaa aaa gat aaa aaa tgc act act ctt aaa gca      624
Glu Asn Ile Ile Lys Glu Lys Asp Lys Lys Cys Thr Thr Leu Lys Ala
        195                 200                 205

aat gtt gca aca gca ctt gga agt ttt aaa aaa gaa ata tgc ctt gaa      672
Asn Val Ala Thr Ala Leu Gly Ser Phe Lys Lys Glu Ile Cys Leu Glu
    210                 215                 220

tta ctt gaa caa tgc tat ttt tac att gga aat tgc gga gac gac gat      720
Leu Leu Glu Gln Cys Tyr Phe Tyr Ile Gly Asn Cys Gly Asp Asp Asp
225                 230                 235                 240

ata att aaa tgt att gaa ttg gga ggg aaa tgc caa gaa caa aac att      768
Ile Ile Lys Cys Ile Glu Leu Gly Gly Lys Cys Gln Glu Gln Asn Ile
                245                 250                 255

gtt tat ata cca cca gga ccc gat ttt gat cca act aga cca gag gct      816
Val Tyr Ile Pro Pro Gly Pro Asp Phe Asp Pro Thr Arg Pro Glu Ala
            260                 265                 270

aca cta gca gag gac ata gac ctg gat gag ctt tat aaa aag gca gaa      864
Thr Leu Ala Glu Asp Ile Asp Leu Asp Glu Leu Tyr Lys Lys Ala Glu
        275                 280                 285

gag gat ggt gtt ttt att gga aaa cat cat tta aga gat gcg aca gct      912
Glu Asp Gly Val Phe Ile Gly Lys His His Leu Arg Asp Ala Thr Ala
    290                 295                 300

tta ttg acg ttg ttg gtt aag aaa gat gat aca gga aaa aat aat aat      960
Leu Leu Thr Leu Leu Val Lys Lys Asp Asp Thr Gly Lys Asn Asn Asn
305                 310                 315                 320

atc gga gaa aaa tgc aat aag att ctc gaa gat aaa tgc aaa aac tct     1008
Ile Gly Glu Lys Cys Asn Lys Ile Leu Glu Asp Lys Cys Lys Asn Ser
                325                 330                 335

caa cag cat gaa gct cta aaa aat tta tgt aat aat aat agt cct aat     1056
Gln Gln His Glu Ala Leu Lys Asn Leu Cys Asn Asn Asn Ser Pro Asn
            340                 345                 350

gca tat gga aaa gaa aaa tgc aaa gaa tta gaa gaa gat att aaa aaa     1104
Ala Tyr Gly Lys Glu Lys Cys Lys Glu Leu Glu Glu Asp Ile Lys Lys
        355                 360                 365

aca tgc aca aac ctc aaa cca acg att ctt aaa aac cat ctt tat gat     1152
```

-continued

```
Thr Cys Thr Asn Leu Lys Pro Thr Ile Leu Lys Asn His Leu Tyr Asp
    370                 375                 380

cca aat gat aaa att gtt gag tgg aga aaa ctg cca aca ttt ctt act     1200
Pro Asn Asp Lys Ile Val Glu Trp Arg Lys Leu Pro Thr Phe Leu Thr
385                 390                 395                 400

aat gaa gac tgt gca aga ttg gaa tct tat tgt ttt tac tac gaa aaa     1248
Asn Glu Asp Cys Ala Arg Leu Glu Ser Tyr Cys Phe Tyr Tyr Glu Lys
                405                 410                 415

gct tgt cca aat gcc aaa gaa gag tgt atg aat ttg agg gca gcg tgt     1296
Ala Cys Pro Asn Ala Lys Glu Glu Cys Met Asn Leu Arg Ala Ala Cys
            420                 425                 430

tat aag aga ggg ctt gat gga cgg gca aat aaa gtg ctg caa gaa aat     1344
Tyr Lys Arg Gly Leu Asp Gly Arg Ala Asn Lys Val Leu Gln Glu Asn
        435                 440                 445

atg cgt ggg tta tta cgt ggt tca aat caa agt tgg ctt aag gag ttt     1392
Met Arg Gly Leu Leu Arg Gly Ser Asn Gln Ser Trp Leu Lys Glu Phe
    450                 455                 460

caa caa aga tta gta aaa gta tgt aag gag cta aaa gaa aat aaa gga     1440
Gln Gln Arg Leu Val Lys Val Cys Lys Glu Leu Lys Glu Asn Lys Gly
465                 470                 475                 480

agt ttc cca aac gat gaa ata ttt gtt ctg tgt gta cag cca gca aaa     1488
Ser Phe Pro Asn Asp Glu Ile Phe Val Leu Cys Val Gln Pro Ala Lys
                485                 490                 495

gct gca cga tta ctt aca cac gat cat caa atg agg gtt atc ttt tta     1536
Ala Ala Arg Leu Leu Thr His Asp His Gln Met Arg Val Ile Phe Leu
            500                 505                 510

cga caa caa ttg gat caa aag aga gat ttt ccg aca gat aaa gac tgc     1584
Arg Gln Gln Leu Asp Gln Lys Arg Asp Phe Pro Thr Asp Lys Asp Cys
        515                 520                 525

aag gaa tta ggg aaa aaa tgc caa gat tta gga aag gat tca aaa gaa     1632
Lys Glu Leu Gly Lys Lys Cys Gln Asp Leu Gly Lys Asp Ser Lys Glu
    530                 535                 540

att aca tgg cca tgt cat acg ctg gag cag caa tgc aat cgc ttg ggg     1680
Ile Thr Trp Pro Cys His Thr Leu Glu Gln Gln Cys Asn Arg Leu Gly
545                 550                 555                 560

act aca gaa att tta aag cag gtt tta ttg gat gaa cac aaa gat act     1728
Thr Thr Glu Ile Leu Lys Gln Val Leu Leu Asp Glu His Lys Asp Thr
                565                 570                 575

ttg aaa gac caa gaa agt tgt gta aaa tac cta aaa gaa aag tgt aat     1776
Leu Lys Asp Gln Glu Ser Cys Val Lys Tyr Leu Lys Glu Lys Cys Asn
            580                 585                 590

aaa tgg tct aga aga gga gat gac cgt ttc tct ttt gta tgt gtc ttc     1824
Lys Trp Ser Arg Arg Gly Asp Asp Arg Phe Ser Phe Val Cys Val Phe
        595                 600                 605

caa aac gct acg tgt gag ctg atg gta aaa gac gtg aaa gac agg tgt     1872
Gln Asn Ala Thr Cys Glu Leu Met Val Lys Asp Val Lys Asp Arg Cys
    610                 615                 620

gaa gta ttc aaa aaa aat ata aaa gct tca tat att att gaa ttt ctt     1920
Glu Val Phe Lys Lys Asn Ile Lys Ala Ser Tyr Ile Ile Glu Phe Leu
625                 630                 635                 640

gaa aat aat aca aat aaa ata aca aca ctg gaa aga aat tgt ccc tct     1968
Glu Asn Asn Thr Asn Lys Ile Thr Thr Leu Glu Arg Asn Cys Pro Ser
                645                 650                 655

tgg cat acg tat tgc aat aga ttt tca cct aat tgt cca ggt ctt acg     2016
Trp His Thr Tyr Cys Asn Arg Phe Ser Pro Asn Cys Pro Gly Leu Thr
            660                 665                 670

aaa gag aat agt tgt aca aaa atc aag aag cat tgt gag ccg ttc tat     2064
Lys Glu Asn Ser Cys Thr Lys Ile Lys Lys His Cys Glu Pro Phe Tyr
        675                 680                 685
```

-continued

```
aaa aga aag gcc ttg gaa gat gct ctc aaa gta gag ctt caa gga aaa     2112
Lys Arg Lys Ala Leu Glu Asp Ala Leu Lys Val Glu Leu Gln Gly Lys
    690                 695                 700

ttg act gat aaa tct aaa tgt gaa cct gca ttg aaa aga tat tgt aca     2160
Leu Thr Asp Lys Ser Lys Cys Glu Pro Ala Leu Lys Arg Tyr Cys Thr
705                 710                 715                 720

gta gcg gga aac gta aat aat gcg tca atc agt ggc tta tgc aaa gct     2208
Val Ala Gly Asn Val Asn Asn Ala Ser Ile Ser Gly Leu Cys Lys Ala
                725                 730                 735

aac acc aag gat aac tct gga aag agt gat gag gat gct aga aag gaa     2256
Asn Thr Lys Asp Asn Ser Gly Lys Ser Asp Glu Asp Ala Arg Lys Glu
            740                 745                 750

ctc tgt gag aaa tta gtg aaa gaa gtg gaa gaa cag tgc aaa gca tta     2304
Leu Cys Glu Lys Leu Val Lys Glu Val Glu Glu Gln Cys Lys Ala Leu
        755                 760                 765

cca aca gaa tta gga caa ccg gca gct gat tta aaa aaa gat tat aag     2352
Pro Thr Glu Leu Gly Gln Pro Ala Ala Asp Leu Lys Lys Asp Tyr Lys
    770                 775                 780

aca tat gag gaa ctt aag aaa cgt gca gag gaa gca atg aac aag tcc     2400
Thr Tyr Glu Glu Leu Lys Lys Arg Ala Glu Glu Ala Met Asn Lys Ser
785                 790                 795                 800

agt ctt gtt ttg tca ctc att aag aaa aac gaa agt aat gta tca aaa     2448
Ser Leu Val Leu Ser Leu Ile Lys Lys Asn Glu Ser Asn Val Ser Lys
                805                 810                 815

agt aat agc aaa aac aag gat aag aat gcc gtt tca aac gga ctt caa     2496
Ser Asn Ser Lys Asn Lys Asp Lys Asn Ala Val Ser Asn Gly Leu Gln
            820                 825                 830

gat acc aca aaa cat gtg aaa ata cta cgg aga gga gtt aag gat gta     2544
Asp Thr Thr Lys His Val Lys Ile Leu Arg Arg Gly Val Lys Asp Val
        835                 840                 845

tcc gta aca gaa tta gaa gct aaa gca ttt gat ttg gca gca gaa gta     2592
Ser Val Thr Glu Leu Glu Ala Lys Ala Phe Asp Leu Ala Ala Glu Val
    850                 855                 860

ttt gga aga tat gta gat ttg aag gaa aga tgt aat aaa ttg gaa tca     2640
Phe Gly Arg Tyr Val Asp Leu Lys Glu Arg Cys Asn Lys Leu Glu Ser
865                 870                 875                 880

gat tgc aga att aag gag gat tgc aaa gac tta gaa gaa gta tgc aaa     2688
Asp Cys Arg Ile Lys Glu Asp Cys Lys Asp Leu Glu Glu Val Cys Lys
                885                 890                 895

aag att aat aag gct tgt cgc aat ctg aag cct ctg gag gtg aag ccg     2736
Lys Ile Asn Lys Ala Cys Arg Asn Leu Lys Pro Leu Glu Val Lys Pro
            900                 905                 910

cac gaa aca gtg aca gaa agt aca acg aca act aca aca aca aca aca     2784
His Glu Thr Val Thr Glu Ser Thr Thr Thr Thr Thr Thr Thr Thr Thr
        915                 920                 925

acc gtt gcc gat ccg aag gca acg gaa tgc aaa tcc tta cag aca aca     2832
Thr Val Ala Asp Pro Lys Ala Thr Glu Cys Lys Ser Leu Gln Thr Thr
    930                 935                 940

gac aca tgg gtt aca cag aca tcg aca cac aca agc acg tct act atc     2880
Asp Thr Trp Val Thr Gln Thr Ser Thr His Thr Ser Thr Ser Thr Ile
945                 950                 955                 960

aca tct acc atc aca tca aaa ata aca ttg aca tca acg agg cga tgc     2928
Thr Ser Thr Ile Thr Ser Lys Ile Thr Leu Thr Ser Thr Arg Arg Cys
                965                 970                 975

aaa cca acc aag tgt acg aca ggg gat gat gca gaa gac gtg aag cca     2976
Lys Pro Thr Lys Cys Thr Thr Gly Asp Asp Ala Glu Asp Val Lys Pro
            980                 985                 990

agt gaa ggc ttg agg gtg agc ggg tgg aat gtg atg agg ggg gtg ata     3024
Ser Glu Gly Leu Arg Val Ser Gly Trp Asn Val Met Arg Gly Val Ile
        995                1000                1005
```

-continued

```
gta gca atg gtt att tcg ttc atg att tag                            3054
Val Ala Met Val Ile Ser Phe Met Ile
   1010                1015


<210> SEQ ID NO 12
<211> LENGTH: 1017
<212> TYPE: PRT
<213> ORGANISM: Pneumocystis carinii sp. f. hominis

<400> SEQUENCE: 12

Ala Arg Ala Val Lys Arg Gln Val Thr Gly Ala Ser Gly Gln Tyr Asp
  1               5                  10                  15

Asp Glu Val Asn Ile Leu Ala Leu Ile Leu Gln Glu Asp Ala Met Glu
             20                  25                  30

Asp Thr Lys Cys Lys Lys Ser Leu Glu Lys Tyr Cys Glu Glu Leu Lys
        35                  40                  45

Lys Ala Ser Leu Asp Met Glu Lys Val His Lys Met Leu Lys Asp Phe
     50                  55                  60

Cys Gly Asn Gly Lys Ala Ser Lys Ala Asn Thr Lys Cys Gln Gly Leu
 65                  70                  75                  80

Gln Ala Lys Val Thr Gly Lys Cys Thr Asn Phe Lys Thr Gln Lys Leu
                 85                  90                  95

Gly Pro Ala Leu Thr Asn Pro Ser Asp Asp Asn Cys Lys Glu Ser Glu
            100                 105                 110

Arg Gln Cys Leu Phe Leu Glu Gly Ala Cys His Asn Leu Val Glu Asp
        115                 120                 125

Cys Asn Lys Leu Arg Asn Leu Cys Tyr Gln Lys Lys Arg Asp Gly Val
    130                 135                 140

Ala Glu Glu Val Leu Leu Arg Ala Leu Arg Ser Asp Leu Asn Lys Thr
145                 150                 155                 160

Glu Thr His Glu Lys Lys Leu Lys Glu Ile Cys Pro Val Leu Gln Arg
                165                 170                 175

Glu Ser Asn Glu Leu Thr Asp Leu Cys Leu Asn Gln Lys Lys Thr Cys
            180                 185                 190

Glu Asn Ile Ile Lys Glu Lys Asp Lys Lys Cys Thr Thr Leu Lys Ala
        195                 200                 205

Asn Val Ala Thr Ala Leu Gly Ser Phe Lys Lys Glu Ile Cys Leu Glu
    210                 215                 220

Leu Leu Glu Gln Cys Tyr Phe Tyr Ile Gly Asn Cys Gly Asp Asp Asp
225                 230                 235                 240

Ile Ile Lys Cys Ile Glu Leu Gly Gly Lys Cys Gln Glu Gln Asn Ile
                245                 250                 255

Val Tyr Ile Pro Pro Gly Pro Asp Phe Asp Pro Thr Arg Pro Glu Ala
            260                 265                 270

Thr Leu Ala Glu Asp Ile Asp Leu Asp Glu Leu Tyr Lys Lys Ala Glu
        275                 280                 285

Glu Asp Gly Val Phe Ile Gly Lys His His Leu Arg Asp Ala Thr Ala
    290                 295                 300

Leu Leu Thr Leu Leu Val Lys Lys Asp Asp Thr Gly Lys Asn Asn Asn
305                 310                 315                 320

Ile Gly Glu Lys Cys Asn Lys Ile Leu Glu Asp Lys Cys Lys Asn Ser
                325                 330                 335

Gln Gln His Glu Ala Leu Lys Asn Leu Cys Asn Asn Asn Ser Pro Asn
            340                 345                 350
```

-continued

```
Ala Tyr Gly Lys Glu Lys Cys Lys Glu Leu Glu Glu Asp Ile Lys Lys
        355                 360                 365

Thr Cys Thr Asn Leu Lys Pro Thr Ile Leu Lys Asn His Leu Tyr Asp
    370                 375                 380

Pro Asn Asp Lys Ile Val Glu Trp Arg Lys Leu Pro Thr Phe Leu Thr
385                 390                 395                 400

Asn Glu Asp Cys Ala Arg Leu Glu Ser Tyr Cys Phe Tyr Tyr Glu Lys
                405                 410                 415

Ala Cys Pro Asn Ala Lys Glu Glu Cys Met Asn Leu Arg Ala Ala Cys
            420                 425                 430

Tyr Lys Arg Gly Leu Asp Gly Arg Ala Asn Lys Val Leu Gln Glu Asn
        435                 440                 445

Met Arg Gly Leu Leu Arg Gly Ser Asn Gln Ser Trp Leu Lys Glu Phe
    450                 455                 460

Gln Gln Arg Leu Val Lys Val Cys Lys Glu Leu Lys Glu Asn Lys Gly
465                 470                 475                 480

Ser Phe Pro Asn Asp Glu Ile Phe Val Leu Cys Val Gln Pro Ala Lys
                485                 490                 495

Ala Ala Arg Leu Leu Thr His Asp His Gln Met Arg Val Ile Phe Leu
            500                 505                 510

Arg Gln Gln Leu Asp Gln Lys Arg Asp Phe Pro Thr Asp Lys Asp Cys
        515                 520                 525

Lys Glu Leu Gly Lys Lys Cys Gln Asp Leu Gly Lys Asp Ser Lys Glu
    530                 535                 540

Ile Thr Trp Pro Cys His Thr Leu Glu Gln Gln Cys Asn Arg Leu Gly
545                 550                 555                 560

Thr Thr Glu Ile Leu Lys Gln Val Leu Leu Asp Glu His Lys Asp Thr
                565                 570                 575

Leu Lys Asp Gln Glu Ser Cys Val Lys Tyr Leu Lys Glu Lys Cys Asn
            580                 585                 590

Lys Trp Ser Arg Arg Gly Asp Asp Arg Phe Ser Phe Val Cys Val Phe
        595                 600                 605

Gln Asn Ala Thr Cys Glu Leu Met Val Lys Asp Val Lys Asp Arg Cys
    610                 615                 620

Glu Val Phe Lys Lys Asn Ile Lys Ala Ser Tyr Ile Ile Glu Phe Leu
625                 630                 635                 640

Glu Asn Asn Thr Asn Lys Ile Thr Thr Leu Glu Arg Asn Cys Pro Ser
                645                 650                 655

Trp His Thr Tyr Cys Asn Arg Phe Ser Pro Asn Cys Pro Gly Leu Thr
            660                 665                 670

Lys Glu Asn Ser Cys Thr Lys Ile Lys Lys His Cys Glu Pro Phe Tyr
        675                 680                 685

Lys Arg Lys Ala Leu Glu Asp Ala Leu Lys Val Glu Leu Gln Gly Lys
    690                 695                 700

Leu Thr Asp Lys Ser Lys Cys Glu Pro Ala Leu Lys Arg Tyr Cys Thr
705                 710                 715                 720

Val Ala Gly Asn Val Asn Asn Ala Ser Ile Ser Gly Leu Cys Lys Ala
                725                 730                 735

Asn Thr Lys Asp Asn Ser Gly Lys Ser Asp Glu Asp Ala Arg Lys Glu
            740                 745                 750

Leu Cys Glu Lys Leu Val Lys Glu Val Glu Glu Gln Cys Lys Ala Leu
        755                 760                 765

Pro Thr Glu Leu Gly Gln Pro Ala Ala Asp Leu Lys Lys Asp Tyr Lys
```

-continued

```
    770                 775                 780

Thr Tyr Glu Glu Leu Lys Lys Arg Ala Glu Glu Ala Met Asn Lys Ser
785                 790                 795                 800

Ser Leu Val Leu Ser Leu Ile Lys Lys Asn Glu Ser Asn Val Ser Lys
                805                 810                 815

Ser Asn Ser Lys Asn Lys Asp Lys Asn Ala Val Ser Asn Gly Leu Gln
            820                 825                 830

Asp Thr Thr Lys His Val Lys Ile Leu Arg Arg Gly Val Lys Asp Val
        835                 840                 845

Ser Val Thr Glu Leu Glu Ala Lys Ala Phe Asp Leu Ala Ala Glu Val
    850                 855                 860

Phe Gly Arg Tyr Val Asp Leu Lys Glu Arg Cys Asn Lys Leu Glu Ser
865                 870                 875                 880

Asp Cys Arg Ile Lys Glu Asp Cys Lys Asp Leu Glu Glu Val Cys Lys
                885                 890                 895

Lys Ile Asn Lys Ala Cys Arg Asn Leu Lys Pro Leu Glu Val Lys Pro
            900                 905                 910

His Glu Thr Val Thr Glu Ser Thr Thr Thr Thr Thr Thr Thr Thr Thr
        915                 920                 925

Thr Val Ala Asp Pro Lys Ala Thr Glu Cys Lys Ser Leu Gln Thr Thr
    930                 935                 940

Asp Thr Trp Val Thr Gln Thr Ser Thr His Thr Ser Thr Ser Thr Ile
945                 950                 955                 960

Thr Ser Thr Ile Thr Ser Lys Ile Thr Leu Thr Ser Thr Arg Arg Cys
                965                 970                 975

Lys Pro Thr Lys Cys Thr Thr Gly Asp Asp Ala Glu Asp Val Lys Pro
            980                 985                 990

Ser Glu Gly Leu Arg Val Ser Gly Trp Asn Val Met Arg Gly Val Ile
        995                1000                1005

Val Ala Met Val Ile Ser Phe Met Ile
   1010                1015


<210> SEQ ID NO 13
<211> LENGTH: 3072
<212> TYPE: DNA
<213> ORGANISM: Pneumocystis carinii sp. f. hominis
<220> FEATURE:
<221> NAME/KEY: CDS
<222> LOCATION: (1)..(3072)

<400> SEQUENCE: 13

atg gcg cgg gcg gtc aag cgg cag gca gca ggg aca cag aat agc att       48
Met Ala Arg Ala Val Lys Arg Gln Ala Ala Gly Thr Gln Asn Ser Ile
  1               5                  10                  15

gat gag gaa cat gtt tta gct tta att cta aag gaa gat gga cta agt       96
Asp Glu Glu His Val Leu Ala Leu Ile Leu Lys Glu Asp Gly Leu Ser
                 20                  25                  30

gag cag gaa tgc aaa aaa aaa cta aaa aaa tat tgc caa gaa ttg act      144
Glu Gln Glu Cys Lys Lys Lys Leu Lys Lys Tyr Cys Gln Glu Leu Thr
         35                  40                  45

gaa gca aaa cta aat ata gaa caa gta cac aga aaa ctt aaa ggt ttt      192
Glu Ala Lys Leu Asn Ile Glu Gln Val His Arg Lys Leu Lys Gly Phe
     50                  55                  60

tgc gaa gat gga aaa gca gat aca aaa tgc aaa gaa ctg aaa gcc aat      240
Cys Glu Asp Gly Lys Ala Asp Thr Lys Cys Lys Glu Leu Lys Ala Asn
 65                  70                  75                  80

att gag aaa aaa tgt act aca atc aaa gga aaa ctt aaa gaa gca att      288
```

-continued

```
Ile Glu Lys Lys Cys Thr Thr Ile Lys Gly Lys Leu Lys Glu Ala Ile
                85                  90                  95

aaa aaa aaa att cag att ata acg gat aag gat tgc aaa gag aat gaa      336
Lys Lys Lys Ile Gln Ile Ile Thr Asp Lys Asp Cys Lys Glu Asn Glu
            100                 105                 110

caa caa tgc cta ttt ttg gag gga gta tgt tca aaa gaa ctt aaa gat      384
Gln Gln Cys Leu Phe Leu Glu Gly Val Cys Ser Lys Glu Leu Lys Asp
        115                 120                 125

gat tgc aat act ttg aga aat aag tgc tat caa aag aaa cgt gat aaa      432
Asp Cys Asn Thr Leu Arg Asn Lys Cys Tyr Gln Lys Lys Arg Asp Lys
    130                 135                 140

gtt gcg gaa gaa gtt ctt tta aga gca ctt cgt agc gat ctt aat gga      480
Val Ala Glu Glu Val Leu Leu Arg Ala Leu Arg Ser Asp Leu Asn Gly
145                 150                 155                 160

tca gtc ata tgt gaa aaa aaa ctt aaa gag att tgc cct gtc atg ggg      528
Ser Val Ile Cys Glu Lys Lys Leu Lys Glu Ile Cys Pro Val Met Gly
                165                 170                 175

agg gaa agt gat gag tta aca aac ttg tgt ctg aac cag aaa gag aca      576
Arg Glu Ser Asp Glu Leu Thr Asn Leu Cys Leu Asn Gln Lys Glu Thr
            180                 185                 190

tgt aag aat att tta att gaa aaa gat aag aag tgc ggt act ctt aaa      624
Cys Lys Asn Ile Leu Ile Glu Lys Asp Lys Lys Cys Gly Thr Leu Lys
        195                 200                 205

aca gat gtt tca gca gca cta gga agt ttt aaa aaa gaa aca tgt ctt      672
Thr Asp Val Ser Ala Ala Leu Gly Ser Phe Lys Lys Glu Thr Cys Leu
    210                 215                 220

gaa tta ctc gaa caa tgc tat ttt tac att gga aat tgc gga gac gac      720
Glu Leu Leu Glu Gln Cys Tyr Phe Tyr Ile Gly Asn Cys Gly Asp Asp
225                 230                 235                 240

gat ata att aaa tgt att gaa ttg gga gga aaa tgc caa gaa caa aat      768
Asp Ile Ile Lys Cys Ile Glu Leu Gly Gly Lys Cys Gln Glu Gln Asn
                245                 250                 255

att gct tat atg cca cca gga ccc gat ttt gat cca act agg cca gag      816
Ile Ala Tyr Met Pro Pro Gly Pro Asp Phe Asp Pro Thr Arg Pro Glu
            260                 265                 270

gct aca ata gca gag gat ata ggg ctg gaa gag ttt tat aag aag gta      864
Ala Thr Ile Ala Glu Asp Ile Gly Leu Glu Glu Phe Tyr Lys Lys Val
        275                 280                 285

gag gag gat gga gtt ttt att gga aag aat cat cta aga gat gcg aca      912
Glu Glu Asp Gly Val Phe Ile Gly Lys Asn His Leu Arg Asp Ala Thr
    290                 295                 300

gct ttg ttg gca ttg ttg atc caa gat tct agt ctt aaa aaa aaa gac      960
Ala Leu Leu Ala Leu Leu Ile Gln Asp Ser Ser Leu Lys Lys Lys Asp
305                 310                 315                 320

gac aaa gag aaa tgc gaa gaa gcc ctt caa aaa agc tgc aaa aat cct     1008
Asp Lys Glu Lys Cys Glu Glu Ala Leu Gln Lys Ser Cys Lys Asn Pro
                325                 330                 335

cat gaa cat gag gct tta gaa agt tta tgt aag aaa aat ggt tta agt     1056
His Glu His Glu Ala Leu Glu Ser Leu Cys Lys Lys Asn Gly Leu Ser
            340                 345                 350

aat gat gga acg aaa aaa tgt gaa gaa ttg caa aat gat att aac aaa     1104
Asn Asp Gly Thr Lys Lys Cys Glu Glu Leu Gln Asn Asp Ile Asn Lys
        355                 360                 365

act tgc aaa att ttc act tca aaa gtc act aat aat cgt ctt ttt gat     1152
Thr Cys Lys Ile Phe Thr Ser Lys Val Thr Asn Asn Arg Leu Phe Asp
    370                 375                 380

cca aca aaa gga aat aat gaa att gtt gga tgg gaa ggg ttg cca aca     1200
Pro Thr Lys Gly Asn Asn Glu Ile Val Gly Trp Glu Gly Leu Pro Thr
385                 390                 395                 400
```

-continued

```
ttt ctt agc aac gaa gat tgt gcg aaa ttg gag tcc tat tgt ttc tat      1248
Phe Leu Ser Asn Glu Asp Cys Ala Lys Leu Glu Ser Tyr Cys Phe Tyr
                405                 410                 415

ttt gaa aaa aaa tgt cca gat gga gaa aat gca tgt aaa aat ata aga      1296
Phe Glu Lys Lys Cys Pro Asp Gly Glu Asn Ala Cys Lys Asn Ile Arg
            420                 425                 430

gca aca tgt tac aaa aga gga ctt gat gca cgg gca aat aaa gtg ctg      1344
Ala Thr Cys Tyr Lys Arg Gly Leu Asp Ala Arg Ala Asn Lys Val Leu
        435                 440                 445

caa gaa aat atg cga gga atg tta cat ggt tca aac aaa agc tgg ctt      1392
Gln Glu Asn Met Arg Gly Met Leu His Gly Ser Asn Lys Ser Trp Leu
    450                 455                 460

gaa aag ttt caa caa gaa tta gta aaa gta tgt gag aaa ctg aaa aaa      1440
Glu Lys Phe Gln Gln Glu Leu Val Lys Val Cys Glu Lys Leu Lys Lys
465                 470                 475                 480

gaa aac aaa gga agt ttc tca aac gat gaa tta ttt att ctg tgt gta      1488
Glu Asn Lys Gly Ser Phe Ser Asn Asp Glu Leu Phe Ile Leu Cys Val
                485                 490                 495

cag cca gca aaa gca gcc cgg ttg ctt aca cat gat ctt cga atg aaa      1536
Gln Pro Ala Lys Ala Ala Arg Leu Leu Thr His Asp Leu Arg Met Lys
            500                 505                 510

act atc ttt tta cga caa caa ctg gat caa aag cga gat ttc ccg aca      1584
Thr Ile Phe Leu Arg Gln Gln Leu Asp Gln Lys Arg Asp Phe Pro Thr
        515                 520                 525

gat aaa aat tgc aag gaa ttg ggg aga aag tgc caa gat tta gga gag      1632
Asp Lys Asn Cys Lys Glu Leu Gly Arg Lys Cys Gln Asp Leu Gly Glu
    530                 535                 540

gat tca aaa gaa att aca tgg cca tgt cat aca ctg gag cag caa tgc      1680
Asp Ser Lys Glu Ile Thr Trp Pro Cys His Thr Leu Glu Gln Gln Cys
545                 550                 555                 560

aat cgc ttg ggg act aca gaa att tta aag cag gtt tta ttg gat gaa      1728
Asn Arg Leu Gly Thr Thr Glu Ile Leu Lys Gln Val Leu Leu Asp Glu
                565                 570                 575

cac aaa gat act ttg aaa gac caa gaa agt tgt gta aaa tac cta aaa      1776
His Lys Asp Thr Leu Lys Asp Gln Glu Ser Cys Val Lys Tyr Leu Lys
            580                 585                 590

gaa aag tgt aat aaa tgg tct aga aga gga gat gac cgt ttc tct ttt      1824
Glu Lys Cys Asn Lys Trp Ser Arg Arg Gly Asp Asp Arg Phe Ser Phe
        595                 600                 605

gta tgt gtc ttc caa aac gct acg tgt gag ctg atg gta aaa gac gtg      1872
Val Cys Val Phe Gln Asn Ala Thr Cys Glu Leu Met Val Lys Asp Val
    610                 615                 620

aaa gac agg tgt gaa gta ttc aaa aaa aat ata aaa gct tca tat att      1920
Lys Asp Arg Cys Glu Val Phe Lys Lys Asn Ile Lys Ala Ser Tyr Ile
625                 630                 635                 640

att gaa ttt ctt gaa aat aat aca aat aaa ata aca aca ctg gaa aga      1968
Ile Glu Phe Leu Glu Asn Asn Thr Asn Lys Ile Thr Thr Leu Glu Arg
                645                 650                 655

aat tgt ccc tct tgg cat acg tat tgc aat aga ttt tca cct aat tgt      2016
Asn Cys Pro Ser Trp His Thr Tyr Cys Asn Arg Phe Ser Pro Asn Cys
            660                 665                 670

cca ggt ctt acg aaa gag aat agt tgt aca aaa atc aag aag cat cgt      2064
Pro Gly Leu Thr Lys Glu Asn Ser Cys Thr Lys Ile Lys Lys His Arg
        675                 680                 685

gag ccg ttc tat aaa aga aag gcc ttg gaa gat gct ctc aaa gta gag      2112
Glu Pro Phe Tyr Lys Arg Lys Ala Leu Glu Asp Ala Leu Lys Val Glu
    690                 695                 700

ctt caa gga aaa ttg act gat aaa tct aaa tgt gaa cct gca ttg aaa      2160
Leu Gln Gly Lys Leu Thr Asp Lys Ser Lys Cys Glu Pro Ala Leu Lys
705                 710                 715                 720
```

-continued

```
aga tat tgt aca gta gcg gga aac gta aat aat gcg tca atc agt ggc     2208
Arg Tyr Cys Thr Val Ala Gly Asn Val Asn Asn Ala Ser Ile Ser Gly
                725                 730                 735

tta tgc aaa gct aac acc aag gat aac tct gga aag agt gat gag gat     2256
Leu Cys Lys Ala Asn Thr Lys Asp Asn Ser Gly Lys Ser Asp Glu Asp
            740                 745                 750

gct aga aag gaa ctc tgt gag aaa tta gtg aaa gaa gtg gaa gaa cag     2304
Ala Arg Lys Glu Leu Cys Glu Lys Leu Val Lys Glu Val Glu Glu Gln
        755                 760                 765

tgc aaa gca tta cca aca gaa tta gga caa ccg gca gct gat cta aaa     2352
Cys Lys Ala Leu Pro Thr Glu Leu Gly Gln Pro Ala Ala Asp Leu Lys
    770                 775                 780

aaa gat tat aag aca tat gag gaa ctt aag aaa cgt gca gag gaa gca     2400
Lys Asp Tyr Lys Thr Tyr Glu Glu Leu Lys Lys Arg Ala Glu Glu Ala
785                 790                 795                 800

atg aac aag tcc agt ctt gtt ttg tca ctc att aag aaa aac gaa agt     2448
Met Asn Lys Ser Ser Leu Val Leu Ser Leu Ile Lys Lys Asn Glu Ser
                805                 810                 815

aat gta tca aaa agt aat agc aaa aac aag gat aag aat gcc gtt tca     2496
Asn Val Ser Lys Ser Asn Ser Lys Asn Lys Asp Lys Asn Ala Val Ser
            820                 825                 830

aac gga ctt caa gat acc aca aaa cat gtg aaa ata cta cgg agg gga     2544
Asn Gly Leu Gln Asp Thr Thr Lys His Val Lys Ile Leu Arg Arg Gly
        835                 840                 845

gtt aag gat gta tcc gta aca gaa tta gaa gct aaa gca ttt gat ttg     2592
Val Lys Asp Val Ser Val Thr Glu Leu Glu Ala Lys Ala Phe Asp Leu
    850                 855                 860

gca gca gaa gta ttt gga aga tat gta gat ttg aag gaa aga tgt aat     2640
Ala Ala Glu Val Phe Gly Arg Tyr Val Asp Leu Lys Glu Arg Cys Asn
865                 870                 875                 880

aaa ttg gaa tca gat tgc aga att aag gag gat tgc aaa gac tta gaa     2688
Lys Leu Glu Ser Asp Cys Arg Ile Lys Glu Asp Cys Lys Asp Leu Glu
                885                 890                 895

gaa gta tgc aaa aag att aat aag gct tgt cgc aat ctg aag cct ctg     2736
Glu Val Cys Lys Lys Ile Asn Lys Ala Cys Arg Asn Leu Lys Pro Leu
            900                 905                 910

gag gtg aag ccg cac gaa aca gtg aca gaa agt aca acg aca act aca     2784
Glu Val Lys Pro His Glu Thr Val Thr Glu Ser Thr Thr Thr Thr Thr
        915                 920                 925

aca aca aca aca acc gtt gcc gat ccg aag gca acg gaa tgc aaa tcc     2832
Thr Thr Thr Thr Thr Val Ala Asp Pro Lys Ala Thr Glu Cys Lys Ser
    930                 935                 940

tta cag aca aca gac aca tgg gtt aca cag aca tcg aca cac aca agc     2880
Leu Gln Thr Thr Asp Thr Trp Val Thr Gln Thr Ser Thr His Thr Ser
945                 950                 955                 960

acg tct act atc aca tct acc atc aca tca aaa ata aca ttg aca tca     2928
Thr Ser Thr Ile Thr Ser Thr Ile Thr Ser Lys Ile Thr Leu Thr Ser
                965                 970                 975

acg agg cga tgc aaa cca acc aag tgt acg aca gga gag gaa gat gat     2976
Thr Arg Arg Cys Lys Pro Thr Lys Cys Thr Thr Gly Glu Glu Asp Asp
            980                 985                 990

gca gga gac gtg aaa ccg agt gag ggg ctg agg atg agt ggg tgg aat     3024
Ala Gly Asp Val Lys Pro Ser Glu Gly Leu Arg Met Ser Gly Trp Asn
        995                1000                1005

gtg atg agg ggg gtg ata gta gca atg gtt att tcg ttc atg att tag     3072
Val Met Arg Gly Val Ile Val Ala Met Val Ile Ser Phe Met Ile
   1010                1015                1020
```

<210> SEQ ID NO 14

-continued

<211> LENGTH: 1023
<212> TYPE: PRT
<213> ORGANISM: Pneumocystis carinii sp. f. hominis

<400> SEQUENCE: 14

```
Met Ala Arg Ala Val Lys Arg Gln Ala Ala Gly Thr Gln Asn Ser Ile
  1               5                  10                  15

Asp Glu Glu His Val Leu Ala Leu Ile Leu Lys Glu Asp Gly Leu Ser
             20                  25                  30

Glu Gln Glu Cys Lys Lys Lys Leu Lys Lys Tyr Cys Gln Glu Leu Thr
         35                  40                  45

Glu Ala Lys Leu Asn Ile Glu Gln Val His Arg Lys Leu Lys Gly Phe
     50                  55                  60

Cys Glu Asp Gly Lys Ala Asp Thr Lys Cys Lys Glu Leu Lys Ala Asn
 65                  70                  75                  80

Ile Glu Lys Lys Cys Thr Thr Ile Lys Gly Lys Leu Lys Glu Ala Ile
                 85                  90                  95

Lys Lys Lys Ile Gln Ile Ile Thr Asp Lys Asp Cys Lys Glu Asn Glu
            100                 105                 110

Gln Gln Cys Leu Phe Leu Glu Gly Val Cys Ser Lys Glu Leu Lys Asp
        115                 120                 125

Asp Cys Asn Thr Leu Arg Asn Lys Cys Tyr Gln Lys Lys Arg Asp Lys
    130                 135                 140

Val Ala Glu Glu Val Leu Leu Arg Ala Leu Arg Ser Asp Leu Asn Gly
145                 150                 155                 160

Ser Val Ile Cys Glu Lys Lys Leu Lys Glu Ile Cys Pro Val Met Gly
                165                 170                 175

Arg Glu Ser Asp Glu Leu Thr Asn Leu Cys Leu Asn Gln Lys Glu Thr
            180                 185                 190

Cys Lys Asn Ile Leu Ile Glu Lys Asp Lys Lys Cys Gly Thr Leu Lys
        195                 200                 205

Thr Asp Val Ser Ala Ala Leu Gly Ser Phe Lys Lys Glu Thr Cys Leu
    210                 215                 220

Glu Leu Leu Glu Gln Cys Tyr Phe Tyr Ile Gly Asn Cys Gly Asp Asp
225                 230                 235                 240

Asp Ile Ile Lys Cys Ile Glu Leu Gly Gly Lys Cys Gln Glu Gln Asn
                245                 250                 255

Ile Ala Tyr Met Pro Pro Gly Pro Asp Phe Asp Pro Thr Arg Pro Glu
            260                 265                 270

Ala Thr Ile Ala Glu Asp Ile Gly Leu Glu Glu Phe Tyr Lys Lys Val
        275                 280                 285

Glu Glu Asp Gly Val Phe Ile Gly Lys Asn His Leu Arg Asp Ala Thr
    290                 295                 300

Ala Leu Leu Ala Leu Leu Ile Gln Asp Ser Ser Leu Lys Lys Lys Asp
305                 310                 315                 320

Asp Lys Glu Lys Cys Glu Glu Ala Leu Gln Lys Ser Cys Lys Asn Pro
                325                 330                 335

His Glu His Glu Ala Leu Glu Ser Leu Cys Lys Lys Asn Gly Leu Ser
            340                 345                 350

Asn Asp Gly Thr Lys Lys Cys Glu Glu Leu Gln Asn Asp Ile Asn Lys
        355                 360                 365

Thr Cys Lys Ile Phe Thr Ser Lys Val Thr Asn Asn Arg Leu Phe Asp
    370                 375                 380

Pro Thr Lys Gly Asn Asn Glu Ile Val Gly Trp Glu Gly Leu Pro Thr
```

-continued

```
385                 390                 395                 400

Phe Leu Ser Asn Glu Asp Cys Ala Lys Leu Glu Ser Tyr Cys Phe Tyr
                405                 410                 415

Phe Glu Lys Lys Cys Pro Asp Gly Glu Asn Ala Cys Lys Asn Ile Arg
            420                 425                 430

Ala Thr Cys Tyr Lys Arg Gly Leu Asp Ala Arg Ala Asn Lys Val Leu
        435                 440                 445

Gln Glu Asn Met Arg Gly Met Leu His Gly Ser Asn Lys Ser Trp Leu
    450                 455                 460

Glu Lys Phe Gln Gln Glu Leu Val Lys Val Cys Glu Lys Leu Lys Lys
465                 470                 475                 480

Glu Asn Lys Gly Ser Phe Ser Asn Asp Glu Leu Phe Ile Leu Cys Val
                485                 490                 495

Gln Pro Ala Lys Ala Ala Arg Leu Leu Thr His Asp Leu Arg Met Lys
            500                 505                 510

Thr Ile Phe Leu Arg Gln Gln Leu Asp Gln Lys Arg Asp Phe Pro Thr
        515                 520                 525

Asp Lys Asn Cys Lys Glu Leu Gly Arg Lys Cys Gln Asp Leu Gly Glu
    530                 535                 540

Asp Ser Lys Glu Ile Thr Trp Pro Cys His Thr Leu Glu Gln Gln Cys
545                 550                 555                 560

Asn Arg Leu Gly Thr Thr Glu Ile Leu Lys Gln Val Leu Leu Asp Glu
                565                 570                 575

His Lys Asp Thr Leu Lys Asp Gln Glu Ser Cys Val Lys Tyr Leu Lys
            580                 585                 590

Glu Lys Cys Asn Lys Trp Ser Arg Arg Gly Asp Asp Arg Phe Ser Phe
        595                 600                 605

Val Cys Val Phe Gln Asn Ala Thr Cys Glu Leu Met Val Lys Asp Val
    610                 615                 620

Lys Asp Arg Cys Glu Val Phe Lys Lys Asn Ile Lys Ala Ser Tyr Ile
625                 630                 635                 640

Ile Glu Phe Leu Glu Asn Asn Thr Asn Lys Ile Thr Thr Leu Glu Arg
                645                 650                 655

Asn Cys Pro Ser Trp His Thr Tyr Cys Asn Arg Phe Ser Pro Asn Cys
            660                 665                 670

Pro Gly Leu Thr Lys Glu Asn Ser Cys Thr Lys Ile Lys Lys His Arg
        675                 680                 685

Glu Pro Phe Tyr Lys Arg Lys Ala Leu Glu Asp Ala Leu Lys Val Glu
    690                 695                 700

Leu Gln Gly Lys Leu Thr Asp Lys Ser Lys Cys Glu Pro Ala Leu Lys
705                 710                 715                 720

Arg Tyr Cys Thr Val Ala Gly Asn Val Asn Asn Ala Ser Ile Ser Gly
                725                 730                 735

Leu Cys Lys Ala Asn Thr Lys Asp Asn Ser Gly Lys Ser Asp Glu Asp
            740                 745                 750

Ala Arg Lys Glu Leu Cys Glu Lys Leu Val Lys Glu Val Glu Glu Gln
        755                 760                 765

Cys Lys Ala Leu Pro Thr Glu Leu Gly Gln Pro Ala Ala Asp Leu Lys
    770                 775                 780

Lys Asp Tyr Lys Thr Tyr Glu Glu Leu Lys Lys Arg Ala Glu Glu Ala
785                 790                 795                 800

Met Asn Lys Ser Ser Leu Val Leu Ser Leu Ile Lys Lys Asn Glu Ser
                805                 810                 815
```

-continued

```
Asn Val Ser Lys Ser Asn Ser Lys Asn Lys Asp Lys Asn Ala Val Ser
            820                 825                 830

Asn Gly Leu Gln Asp Thr Thr Lys His Val Lys Ile Leu Arg Arg Gly
        835                 840                 845

Val Lys Asp Val Ser Val Thr Glu Leu Glu Ala Lys Ala Phe Asp Leu
    850                 855                 860

Ala Ala Glu Val Phe Gly Arg Tyr Val Asp Leu Lys Glu Arg Cys Asn
865                 870                 875                 880

Lys Leu Glu Ser Asp Cys Arg Ile Lys Glu Asp Cys Lys Asp Leu Glu
                885                 890                 895

Glu Val Cys Lys Lys Ile Asn Lys Ala Cys Arg Asn Leu Lys Pro Leu
            900                 905                 910

Glu Val Lys Pro His Glu Thr Val Thr Glu Ser Thr Thr Thr Thr Thr
        915                 920                 925

Thr Thr Thr Thr Thr Val Ala Asp Pro Lys Ala Thr Glu Cys Lys Ser
    930                 935                 940

Leu Gln Thr Thr Asp Thr Trp Val Thr Gln Thr Ser Thr His Thr Ser
945                 950                 955                 960

Thr Ser Thr Ile Thr Ser Thr Ile Thr Ser Lys Ile Thr Leu Thr Ser
                965                 970                 975

Thr Arg Arg Cys Lys Pro Thr Lys Cys Thr Thr Gly Glu Glu Asp Asp
            980                 985                 990

Ala Gly Asp Val Lys Pro Ser Glu Gly Leu Arg Met Ser Gly Trp Asn
        995                 1000                1005

Val Met Arg Gly Val Ile Val Ala Met Val Ile Ser Phe Met Ile
   1010                1015                1020


<210> SEQ ID NO 15
<211> LENGTH: 249
<212> TYPE: DNA
<213> ORGANISM: Pneumocystis carinii sp. f. hominis
<220> FEATURE:
<221> NAME/KEY: CDS
<222> LOCATION: (1)..(249)

<400> SEQUENCE: 15

gag tgc caa tct ctg cag acg aca gac acg tgg gtc aca aag acg tcg       48
Glu Cys Gln Ser Leu Gln Thr Thr Asp Thr Trp Val Thr Lys Thr Ser
  1               5                  10                  15

acc cat act agc act tct acg act acg tcc aca gtc aca tcg aga ata       96
Thr His Thr Ser Thr Ser Thr Thr Thr Ser Thr Val Thr Ser Arg Ile
             20                  25                  30

aca ctc acc tca acg agg cgg tgt aag cct acg aag tgt acg aca gga      144
Thr Leu Thr Ser Thr Arg Arg Cys Lys Pro Thr Lys Cys Thr Thr Gly
         35                  40                  45

gag gaa gat gat gca gga gag gtg aag ccg agt gaa ggg ctg agg atg      192
Glu Glu Asp Asp Ala Gly Glu Val Lys Pro Ser Glu Gly Leu Arg Met
     50                  55                  60

agt ggg tgg agt gtg atg agg ggg gtg tta tta gca atg atg att tca      240
Ser Gly Trp Ser Val Met Arg Gly Val Leu Leu Ala Met Met Ile Ser
 65                  70                  75                  80

ttc atg att                                                          249
Phe Met Ile


<210> SEQ ID NO 16
<211> LENGTH: 83
<212> TYPE: PRT
<213> ORGANISM: Pneumocystis carinii sp. f. hominis
```

-continued

<400> SEQUENCE: 16

```
Glu Cys Gln Ser Leu Gln Thr Thr Asp Thr Trp Val Thr Lys Thr Ser
  1               5                  10                  15

Thr His Thr Ser Thr Ser Thr Thr Thr Ser Thr Val Thr Ser Arg Ile
             20                  25                  30

Thr Leu Thr Ser Thr Arg Arg Cys Lys Pro Thr Lys Cys Thr Thr Gly
         35                  40                  45

Glu Glu Asp Asp Ala Gly Glu Val Lys Pro Ser Glu Gly Leu Arg Met
     50                  55                  60

Ser Gly Trp Ser Val Met Arg Gly Val Leu Leu Ala Met Met Ile Ser
 65                  70                  75                  80

Phe Met Ile
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 17
gaatgcaaat ccttacagac aacag 25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 18
gaatgcaaat ctttacagac aacag 25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 19
tgcaaaccaa ccaagtgtac gacagg 26

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 20
aaatcatgaa cgaaataacc attgc 25

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: synthetic -continued oligonucleotide

<400> SEQUENCE: 21
tttcatatgg cgcgggcggt caagcggcag 30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 22
ctaaatcatg aacgaaataa ccattgctac 30

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 23
gaattcgatc tgaagcctct ggag 24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 24
ttctagaaac ccactcatct tcaa 24

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: synthetic
peptide

<400> SEQUENCE: 25

```
Lys Met Tyr Gly Leu Phe Tyr Gly Ser Gly Lys Glu Trp Phe Lys Lys
  1               5                  10                  15

Leu Leu Glu Lys Ile Met
             20
```

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: synthetic
peptide

<400> SEQUENCE: 26

```
Thr Ile Thr Ser Thr Ile Thr Ser Lys Ile Thr Leu Thr Ser Thr
  1               5                  10                  15
```